(12) United States Patent
Lee et al.

(10) Patent No.: US 7,202,056 B2
(45) Date of Patent: Apr. 10, 2007

(54) POLYNUCLEOTIDES ENCODING A HUMAN CELL SURFACE PROTEIN WITH IMMUNOGLOBULIN FOLDS, BGS-19

(75) Inventors: Liana M. Lee, Somerset, NJ (US); John N. Feder, Belle Mead, NJ (US); Shujian Wu, Langhorne, PA (US); Jian Chen, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 355 days.

(21) Appl. No.: 10/403,938

(22) Filed: Mar. 28, 2003

(65) Prior Publication Data

US 2004/0025195 A1 Feb. 5, 2004

Related U.S. Application Data

(60) Provisional application No. 60/368,422, filed on Mar. 28, 2002.

(51) Int. Cl.
| | |
|---|---|
| C12P 21/06 | (2006.01) |
| C12N 15/87 | (2006.01) |
| C12N 1/20 | (2006.01) |
| C12N 15/74 | (2006.01) |
| C07H 21/04 | (2006.01) |

(52) U.S. Cl. ................. 435/69.1; 435/455; 435/252.3; 435/320.1; 536/23.5

(58) Field of Classification Search ............... 435/69.1, 435/455, 252.3, 320.1; 536/23.5
See application file for complete search history.

(56) References Cited

FOREIGN PATENT DOCUMENTS

| WO | WO1999/046281 A2 | 9/1999 |
|---|---|---|
| WO | WO 00/59942 | 10/2000 |
| WO | WO 01/75067 A2 | 10/2001 |
| WO | WO 02/50105 | 6/2002 |
| WO | WO 02/096452 | 12/2002 |
| WO | WO 03/054152 A2 | 7/2003 |
| WO | WO 03/056027 A1 | 7/2003 |
| WO | WO2004/060270 A2 | 7/2004 |

OTHER PUBLICATIONS

Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Adams, M. et al., "Rapid cDNA sequencing (expressed sequence tags) from a directionally cloned human infant brain cDNA library". Nature genetics, vol. 4, pp. 373-380 (1993).
Adriaansen, H.J. et al., "Expression of the myeloid differentiation antigen CD33 depends on the presence of human chromosome 19 in human-mouse hybrids", Ann Hum Genet, vol. 54, pp. 115-119 (1990).
Altschul, Stephen, et al., "Gapped BLAST and PSI-BLAST: a new generation of protein database search programs", Nucleic Acids Research, vol. 25, No. 17, pp. 3389-3402 (1997).
Avril, T. et al., "Siglec-5 (CD170) Can Mediate Inhibitory Signaling in the Absence of Immunoreceptor Tyrosine-based inhibitory Motif Phosphorylation", The Journal of Biological Chemistry, vol. 280, No. 20, pp. 19843-19851 (2005).
Balaian L. et al., "Anti-CD33 monoclonal antibodies enhance the cytotoxic effects of cytosine arabinoside and idarubicin on acute myeloid leukemia cells through similarities in their signaling pathways", Experimental Hematology, vol. 33, pp. 199-211 (2005).
Clark, H.F. et al., "The secreted Protein discovery Initiative (SPDI), a large-scale effort to Identify Novel Human Secreted and Transmembrane Proteins: A Bioinformatics Assessment", Genome Research, vol. 13, pp. 2265-2270 (2003).
Comish, A.L. et al., "Characterization of Siglec-3, a Novel Glycoprotein Expressed on Myeloid Cells Related to CD33", Blood, vol. 92, No. 6, pp. 2123-2132 (1998).
Dideberg, O. et al., "Tubulin tyrosine ligase: a shared fold with the glutathione synthetase ADP-forming family", TIBS, vol. 23, pp. 57-58 (1998).
Egner, W. et al., "Identification of Potent Mixed Leukocyte Reaction-Stimulatory Cells in Human Bone Marrow", The Journal of Immunology, vol. 150, No. 7, pp. 3043-3053 (1993).
Erickson-Miller, C. et al., "Characterization of Siglec-5 (CD170) expression and functional activity of anti-Siglec-5 antibodies on human phagocytes", Experimental Hematology, vol. 31, pp. 382-388 (2003).
Falco, M. et al., "Identification and Molecular Cloning of p75/AIRM1, A Novel member of the Sialoadhesin Family that Functions as an Inhibitory Receptor in Human Natural Killer Cells", J. Exp. Med, vol. 190, No. 6, pp. 793-801 (1999).

(Continued)

*Primary Examiner*—Maher M. Haddad
(74) *Attorney, Agent, or Firm*—Stephen C. D'Amico

(57) ABSTRACT

The present invention provides novel polynucleotides encoding BGS-19 polypeptides, fragments and homologues thereof. Also provided are vectors, host cells, antibodies, and recombinant and synthetic methods for producing said polypeptides. The invention further relates to diagnostic and therapeutic methods for applying the novel BGS-19 polypeptides to the diagnosis, treatment, and/or prevention of various diseases and/or disorders related to these polypeptides. The invention further relates to screening methods for identifying agonists and antagonists of the polynucleotides and polypeptides of the present invention.

12 Claims, 14 Drawing Sheets

OTHER PUBLICATIONS

Freeman, S.D. et al., "Characterization of CD33 as a New member of the Sialoadhesin Family of Cellular Interaction Molecules", Blood, vol. 85, No. 8, pp. 2005-2012 (1995).
Garnache-Ottou, F. et al., "Expression of the myeloid-associated marker CD33 is not an exclusive factor for leukemic plasmacytoid dendritic cells", Blood, vol. 105, No. 3, pp. 1256-1264 (2005).
Grobe, K. et al., "Role of protein kinase C in the phosphorylation of CD33 (Siglec-3) and its effect on lectin activity", Blood, vol. 99, No. 9, pp. 3188-3196 (2002).
Handgretinger, R. et al., "Expression of an early myelopoietic antigen (CD33) on a subset of human umbilical cord blood-derived natural killer cells." Immunology Letters, vol. 37, pp. 223-228 (1993).
Kim, H.S. "Assignment[1] of the human OB binding protein-2 gene (CD33L2) to chromosome 19q13.3 by radiation hybrid mapping", Cytogenet Cell Genet, vol. 84, pp. 96 (1999).
Liu, H. et al., "Myeloid-lymphoid initiating cells (ML-IC) are highly enriched in the rhodamine-c-kit$^+$CD33$^+$CD38fraction of umbilical cord CD34$^+$ cells", Experimental Hematology, vol. 30, pp. 582-589 (2002).
Mingari, M.C. et al;, "Regulation of myeloid cell proliferation and survival by p75/AIRM1 and CD33 surface receptors", Progress in Basic and Clinical Immunology, Kluwer Academic/Plenum Publishers pp. 55-61 (2001).
Patel, N. et al., "OB-BP1/Siglec-6", The Journal of Biological Chemistry, vol. 274, No. 32, pp. 22729-22738 (1999).
Sgroi, D. et al., "A single N-linked Glycosylation Site is Implicated in the Regulation of Ligand Recognition by the I-type Lectins CD22 and CD33", The Journal of Biological Chemistry, vol. 271, No. 31, pp. 18803-18809 (1996).
Simmons, D. et al., "Isolation of a cDNA encoding CD33, A Differentiation antigen of myeloid progenitor cells[1]", The Journal of Immunology, vol. 141, No. 8, pp. 2797-2800 (1988).
Takei, Y. et al., "Molecular cloning of a novel gene similar to myeloid antigen CD33 and its specific expression in placenta", Cytogenetics Cell Genetics, vol. 78, pp. 295-300 (1997).
Taylor, V. et al., "The Myeloid-specific Sialic Acid-binding Receptor, CD33, Associates with the Protein-tyrosine Phosphatases, SHP-1 and SHP-2", The Journal of Biological Chemistry, vol. 274, No. 17, pp. 11505-11512 (1999).
Vitale, C. et al., "Engagement of p75/AIRM1 or CD33 inhibits the proliferation of normal or leukemic myeloid cells", PNAS, vol. 96, No. 26, pp. 15091-15096 (1999).
Walter, R. et al., "Influence of CD33 expression levels and ITIM-dependent internalization on gemtuzumab ozogamicin-induced cytotoxicity", Blood, vol. 105, No. 3, pp. 1295-1302 (2005).
Wellhausen, S.R. et al., "CD33:Biochemical and biological characterization and evaluation of clinical relevance", J Biol Regul Homeost Agents, vol. 16, pp. 139-143 (2002).
Whitney, G. et al., "A new siglec family member, siglec-10, is expressed in cells of the immune system and has signaling properties similar to CD33", Eur. J. Biochem. vol. 268, pp. 6083-6096 (2001).
Williams, A. et al., "The Immunoglobulin superfamily-Domains for cell surface recognition [1,2]", Ann. Rev. Immunol. vol. 6, pp. 381-405 (1988).
Yousef, G. et al., "Genomic organization of the siglec gene locus on chromosome 19q13.4 and cloning of two new siglec pseudogenes", Gene, vol. 286, pp. 259-270 (2002).
NCBI Entrez Accession No. AA341128 (gi:1993613) Adams, M.D. et al., Apr. 21, 1997.
NCBI Entrez Accession No. AAH39008 (gi:24658685) Strausberg, R. Nov. 6, 2002.
NCBI Entrez Accession No. AAQ88502 (gi:37181376) Clark, H.F. et al. Oct. 3, 2003.
NCBI Entrez Accession No. AC011452 (gi:9885999) DOE Joint Genome Institute and Stanford Human Genome Center. Aug. 23, 2000.
NCBI Entrez Accession No. AY358135 (gi:3718375) Clark, H.F. et al. Oct. 3, 2003.
NCBI Entrez Accession No. BF205116 (gi:11098702) NIH-MGC hhtp://mgc.nci.nih.gov/. Nov. 6, 2000.
NCBI Entrez Accession No. BF308356 (gi:11255555) NIH-MGC hhtp://mgc.nci.nih.gov/. Nov. 21, 2000.
NCBI Entrez Accession No. BF969219 (gi:12336434) NIH-MGC hhtp://mgc.nci.nih.gov/. Jan. 22, 2001.
NCBI Entrez Accession No. BG826221 (gi:14173808) NIH-MGC hhtp://mgc.nci.nih.gov/. May 22, 2001.
NCBI Entrez Accession No. BI518708 (gi:15343500) NIH-MGC hhtp://mgc.nci.nih.gov/. Aug. 29, 2001.
NCBI Entrez Accession No. NP_001763 (gi:50727000) Walter, R.B. et al., Sep. 24, 2005.
NCBI Entrez Accession No. NP_003821 (gi:4502659) Avril, T. et al. Sep. 23, 2005.
NCBI Entrez Accession No. NP_443116 (gi:16418393) Clark, H.F. et al. Sep. 24, 2005.
NCBI Entrez Accession No. XM_375634 (gi:42661670) Documentation of NCBI's Annotation Process, Feb. 19, 2004.
NCBI Entrez Accession No. XM_375634 (gi:51474763) Documentation of NCBI's Annotation Process, Aug. 20, 2004.
NCBI Entrez Accession No. XP_053106 (gi:15303482) NCBI Annotation Project, May 13, 2002.
NCBI Entrez Accession No. XP_053107 (gi:15303486) NCBI Annotation Project. May 13, 2002.
NCBI Entrez Accession No. XP_351209 (gi:37551984) Documentation of NCBI's Annotation Process. Oct. 17, 2003.
NCBI Entrez Accession No. 375634 (gi:5147464) Documentation of NCBI's Annotation Process. Aug. 20, 2004.
NCBI Entrez Accession No. gi|14718451, Angata, T. et al., Jul. 1, 2002.
NCBI Entrez Accession No. gi|16418393, Angata, T. et al., Oct. 5, 2003.
NCBI Entrez Accession No. gi|19716086, Seno, M. et al., Mar. 26, 2002.
NCBI Entrez Accession No. gi|25009265, Angata, T. et al., Mar. 15, 2004.
Swiss-Prot Accession No. Q96RL6, Release 41, Feb. 2003.
Angata, T. et al., "Cloning and Characterization of Human Siglec-11", The Journal of Biological Chemistry, vol. 277, No. 27, pp. 24466-24474 (2002).
Clark, H.F. et al., "The Secreted Protein Discovery Initiative (SPDI), a Large-Scale Effort to Identify Novel Human Secreted and Transmembrane Proteins: A Bioinformatics Assessment", Genome Research, vol. 13, pp. 2265-2270 (2003).
Crocker, et al., "New I-type lectins of the CD33-related siglec subgroup identified through genomics", Biochem. Soc. Symp., vol. 69, pp. 83-96 (2002).
Crocker, P.R., Genomic analysis of n ovel Siglecs (sialic acid binding Ig-type lectins), Biochem. Society Transactions, vol. 30, Part 1, pp. A3 (2001).
NCBI Entrez Accession No. AF337818 (gi:14718450), Angata, et al., Jul. 1, 2002.

* cited by examiner

FIG. 1A

```
  1  CGGACGCGTGGGCGAGGCTCCTCCTCTGTGGATGGTCACTGCCCCTCCACCAGGCTTCCT    60

61  GCTGGAGGAGTTTCCTTCCCAGCCAGGCCGGCCCAGAAGCCAGATGGTCCCGGGACAGGC   120

121  CCAGCCCCAGAGCCCAGAGATGCTGCTGCTGCCCCTGCTGCTGCCCGTGCTGGGGGCGGG   180
  1                        M  L  L  L  P  L  L  L  P  V  L  G  A  G    14

181  GTCCCTGAACAAGGATCCCAGTTACAGTCTTCAAGTGCAGAGGCAGGTGCCGGTGCCGGA   240
 15   S  L  N  K  D  P  S  Y  S  L  Q  V  Q  R  Q  V  P  V  P  E    34

241  GGGCCTGTGTGTCATCGTGTCTTGCAACCTCTCCTACCCCCGGGATGGCTGGGACGAGTC   300
 35   G  L  C  V  I  V  S  C  N  L  S  Y  P  R  D  G  W  D  E  S    54

301  TACTGCTGCTTATGGCTACTGGTTCAAAGGACGGACCAGCCCAAAGACGGGTGCTCCTGT   360
 55   T  A  A  Y  G  Y  W  F  K  G  R  T  S  P  K  T  G  A  P  V    74

361  GGCCACTAACAACCAGAGTCGAGAGGTGGAAATGAGCACCCGGGACCGATTCCAGCTCAC   420
 75   A  T  N  N  Q  S  R  E  V  E  M  S  T  R  D  R  F  Q  L  T    94

421  TGGGGATCCCGGCAAAGGGAGCTGCTCCTTGGTGATCAGAGACGCGCAGAGGGAGGATGA   480
 95   G  D  P  G  K  G  S  C  S  L  V  I  R  D  A  Q  R  E  D  E   114

481  GGCATGGTACTTCTTTCGGGTGGAGAGAGGAAGCCGTGTGAGACATAGTTTCCTGAGCAA   540
115   A  W  Y  F  F  R  V  E  R  G  S  R  V  R  H  S  F  L  S  N   134

541  TGCGTTCTTTCTAAAAGTAACAGCCCTGACTAAGAAGCCTGATGTCTACATCCCCGAGAC   600
135   A  F  F  L  K  V  T  A  L  T  K  K  P  D  V  Y  I  P  E  T   154

601  CCTGGAGCCCGGGCAGCCGGTGACGGTCATCTGTGTGTTTAACTGGGCTTTCAAGAAATG   660
155   L  E  P  G  Q  P  V  T  V  I  C  V  F  N  W  A  F  K  K  C   174

661  TCCAGCCCCTTCTTTCTCCTGGACGGGGGCTGCCCTCTCCCCTAGAAGAACCAGACCAAG   720
175   P  A  P  S  F  S  W  T  G  A  A  L  S  P  R  R  T  R  P  S   194

721  CACCTCCCAGCCCTCAGACCCCGGGGTCCTGGAGCTGCCACCCATTCAAATGGAGCACGA   780
195   T  S  Q  P  S  D  P  G  V  L  E  L  P  P  I  Q  M  E  H  E   214

781  AGGAGAGTTCACCTGCCACGCTCAGCACCCTCTGGGCTCCCAGCACGTCTCTCTCAGCCT   840
215   G  E  F  T  C  H  A  Q  H  P  L  G  S  Q  H  V  S  L  S  L   234
```

FIG. 1B

```
841  CTCCGTGCACTGGAAGCTGGAGCATGGGGGAGGACTTGGCCTGGGGGCTGCCCTGGGAGC  900
235   S   V   H   W   K   L   E   H   G   G   G   L   G   L   G   A   A   L   G   A   254

901  TGGCGTCGCTGCCCTGCTCGCTTTCTGTTCCTGCCTTGTCGTCTTCAGGGTGAAGATCTG  960
255   G   V   A   A   L   L   A   F   C   S   C   L   V   V   F   R   V   K   I   C   274

961  CAGGAAGGAAGCTCGCAAGAGGGCAGCAGCTGAGCAGGACGTGCCCTCCACCCTGGGACC  1020
275   R   K   E   A   R   K   R   A   A   A   E   Q   D   V   P   S   T   L   G   P   294

1021 CATCTCCCAGGGTCACCAGCATGAATGCTCGGCAGGCAGCTCCCAAGACCACCCGCCCCC  1080
295   I   S   Q   G   H   Q   H   E   C   S   A   G   S   S   Q   D   H   P   P   P   314

1081 AGGTGCAGCCACCTACACCCCGGGGAAGGGGGAAGAGCAGGAGCTCCACTATGCCTCCCT  1140
315   G   A   A   T   Y   T   P   G   K   G   E   E   Q   E   L   H   Y   A   S   L   334

1141 CAGCTTCCAGGGCCTGAGGCTCTGGGAGCCTGCGGACCAGGAGGCCCCCAGCACCACCGA  1200
335   S   F   Q   G   L   R   L   W   E   P   A   D   Q   E   A   P   S   T   T   E   354

1201 GTACTCGGAGATCAAGATCCACACAGGACAGCCCCTGAGGGGCCCAGGCTTTGGGCTTCA  1260
355   Y   S   E   I   K   I   H   T   G   Q   P   L   R   G   P   G   F   G   L   Q   374

1261 ATTGGAGAGGGAGATGTCAGGGATGGTTCCAAAGTGAAGAGGTCTCCATGGCAACAGGAC  1320
375   L   E   R   E   M   S   G   M   V   P   K                                       385

1321 ACCAGCAAGTGTGTGGGAGTCGCACTGGTGTGACGGCCAGAACTGGACTCAGATTTCAGC  1380

1381 CCCATCCCCAATGAAGAGCTTGAGTTTGAAGATTATACTTTTTTTGAGACAGGGTCTGAC  1440

1441 TCTGTCCTCCAGGCCGGAGTCCAGTGGTGCAATCTCGGCTCACTGTAGCCTCAACCTGCC  1500

1501 GGGTTGAAGTGAGCCTCCCATTTCAGCCTCCCAAGTAGCTGGGACTACAATTGTGAGCCA  1560

1561 CCATGCCAGGCTCATTGTTGTATTTTTGGTAGAGACGGGGTTTTGCCATGTTTCCCTGGC  1620

1621 TGGTCTCAGACTCCTGGGCTCAAGCAATCTGCCCGCCTCTGCCTCCCAGGGTGCTGGGAT  1680

1681 TGCAGACGTGAGCCACCACAGCTGGCTGAAGATTATACTTTCAATTCAGAGCGAGTTTGA  1740

1741 AGATGACACTTTGAGGCATCGTGTCTATGGTTCATTACTACAGAAGCTTCTCTGGATGTG  1800
```

FIG. 1C

```
1801  TAAAGCACAGGAAACCAGGCAGAGGAGGCACAGGGTGCTCTCCAGAACGAGAAGCCAGCT  1860

1861  CCTGGAGTTGTTTGCTGCAACTGCCATTCCCCGTTGATGACCATGCTCTTCCTTCAGAAG  1920

1921  AGGGAGAGTGAGAGGACCAAGTCCAAGTGGTTCCCATTTGAACATTTAAAAAAAAAAAAA  1980

1981  AAAAG  1985
```

FIG. 2A

```
  1  GGGTCCCTGAACAAGGATCCCAGTTACAGTCTTCAAGTGCAGAGGCAGGTGCCGGTGCCG   60
  1   G  S  L  N  K  D  P  S  Y  S  L  Q  V  Q  R  Q  V  P  V  P   20

61  GAGGGCCTGTGTGTCATCGTGTCTTGCAACCTCTCCTACCCCCGGGATGGCTGGGACGAG  120
 21   E  G  L  C  V  I  V  S  C  N  L  S  Y  P  R  D  G  W  D  E   40

121  TCTACTGCTGCTTATGGCTACTGGTTCAAAGGACGGACCAGCCCAAAGACGGGTGCTCCT  180
 41   S  T  A  A  Y  G  Y  W  F  K  G  R  T  S  P  K  T  G  A  P   60

181  GTGGCCACTAACAACCAGAGTCGAGAGGTGGAAATGAGCACCCGGGACCGATTCCAGCTC  240
 61   V  A  T  N  N  Q  S  R  E  V  E  M  S  T  R  D  R  F  Q  L   80

241  ACTGGGGATCCCGGCAAAGGGAGCTGCTCCTTGGTGATCAGAGACGCGCAGAGGGAGGAT  300
 81   T  G  D  P  G  K  G  S  C  S  L  V  I  R  D  A  Q  R  E  D  100

301  GAGGCATGGTACTTCTTTCGGGTGGAGAGAGGAAGCCGTGTGAGACATAGTTTCCTGAGC  360
101   E  A  W  Y  F  F  R  V  E  R  G  S  R  V  R  H  S  F  L  S  120

361  AATGCGTTCTTTCTAAAAGTAACAGCCCTGACTAAGAAGCCTGATGTCTACATCCCCGAG  420
121   N  A  F  F  L  K  V  T  A  L  T  K  K  P  D  V  Y  I  P  E  140

421  ACCCTGGAGCCCGGGCAGCCGGTGACGGTCATCTGTGTGTTTAACTGGGCTTTCAAGAAA  480
141   T  L  E  P  G  Q  P  V  T  V  I  C  V  F  N  W  A  F  K  K  160

481  TGTCCAGCCCCTTCTTTCTCCTGGACGGGGGCTGCCCTCTCCCCTAGAAGAACCAGACCA  540
161   C  P  A  P  S  F  S  W  T  G  A  A  L  S  P  R  R  T  R  P  180

541  AGCACCTCCCACTTCTCAGTGCTCAGCTTCACGCCCAGCCCCCAGGACCACGACACCGAC  600
181   S  T  S  H  F  S  V  L  S  F  T  P  S  P  Q  D  H  D  T  D  200

601  CTCACCTGCCATGTGGACTTCTCCAGAAAGGGTGTGAGCGCACAGAGGACCGTCCGACTC  660
201   L  T  C  H  V  D  F  S  R  K  G  V  S  A  Q  R  T  V  R  L  220

661  CGTGTGGCCTCCCTGAGCTGCACGTCGATTCTGCCTCTTCCTTCCCTAGTCCTGGAAAAC  720
221   R  V  A  S  L  S  C  T  S  I  L  P  L  P  S  L  V  L  E  N  240

721  CTCGGGAACGGCACATCCCTCCCGGTCCTGGAGGGCCAAAGCCTGCGCCTGGTCTGTGTC  780
241   L  G  N  G  T  S  L  P  V  L  E  G  Q  S  L  R  L  V  C  V  260

781  ACCCACAGCAGCCCCCCAGCCAGGCTGAGCTGGACCCGGTGGGGACAGACCGTGGGCCCC  840
261   T  H  S  S  P  P  A  R  L  S  W  T  R  W  G  Q  T  V  G  P  280
```

FIG. 2B

```
 841  TCCCAGCCCTCAGACCCCGGGGTCCTGGAGCTGCCACCCATTCAAATGGAGCACGAAGGA   900
 281   S   Q   P   S   D   P   G   V   L   E   L   P   P   I   Q   M   E   H   E   G    300

901  GAGTTCACCTGCCACGCTCAGCACCCTCTGGGCTCCCAGCACGTCTCTCTCAGCCTCTCC   960
 301   E   F   T   C   H   A   Q   H   P   L   G   S   Q   H   V   S   L   S   L   S    320

961  GTGCACTACCCTCCACAGCTGCTGGGCCCCTCCTGCTCCTGGGAGGCTGAGGGTCTGCAC  1020
 321   V   H   Y   P   P   Q   L   L   G   P   S   C   S   W   E   A   E   G   L   H    340

1021  TGCAGCTGCTCCTCCCAGGCCAGCCCGGCCCCCTCTCTGCGCTGGTGGCTTGGGGAGGAG  1080
 341   C   S   C   S   S   Q   A   S   P   A   P   S   L   R   W   W   L   G   E   E    360

1081  CTGCTGGAGGGGAACAGCAGTCAGGGCTCCTTCGAGGTCACCCCCAGCTCAGCCGGGCCC  1140
 361   L   L   E   G   N   S   S   Q   G   S   F   E   V   T   P   S   S   A   G   P    380

1141  TGGGCCAACAGCTCCCTGAGCCTCCATGGAGGGCTCAGCTCCGGCCTCAGGCTCCGCTGT  1200
 381   W   A   N   S   S   L   S   L   H   G   G   L   S   S   G   L   R   L   R   C    400

1201  AAGGCCTGGAACGTCCACGGGGCCCAGAGTGGCTCTGTCTTCCAGCTGCTACCAGGGAAG  1260
 401   K   A   W   N   V   H   G   A   Q   S   G   S   V   F   Q   L   L   P   G   K    420

1261  CTGGAGCATGGGGGAGGACTTGGCCTGGGGGCTGCCCTGGGAGCTGGCGTCGCTGCCCTG  1320
 421   L   E   H   G   G   G   L   G   L   G   A   A   L   G   A   G   V   A   A   L    440

1321  CTCGCTTTCTGTTCCTGCCTTGTCGTCTTCAGGAAATACTCAATTTCCAGATCCTCTTGT  1380
 441   L   A   F   C   S   C   L   V   V   F   R   K   Y   S   I   S   R   S   S   C    460

1381  GCATCCTCCTTGCTCTCGCTTAGCCCCCATGACCCTAATTTGACCCCCTTTCTCCCCTGC  1440
 461   A   S   S   L   L   S   L   S   P   H   D   P   N   L   T   P   F   L   P   C    480

1441  ATTCAGGGTCACCAGCATGAATGCTCGGCAGGCAGCTCCCAAGACCACCCGCCCCCAGGT  1500
 481   I   Q   G   H   Q   H   E   C   S   A   G   S   S   Q   D   H   P   P   P   G    500

1501  GCAGCCACCTACACCCCGGGGAAGGGGGAAGAGCAGGAGCTCCACTATGCCTCCCTCAGC  1560
 501   A   A   T   Y   T   P   G   K   G   E   E   Q   E   L   H   Y   A   S   L   S    520

1561  TTCCAGGGCCTGAGGCTCTGGGAGCCTGCGGACCAGGAGGCCCCCAGCACCACCGAGTAC  1620
 521   F   Q   G   L   R   L   W   E   P   A   D   Q   E   A   P   S   T   T   E   Y    540

1621  TCGGAGATCAAG  1632
 541   S   E   I   K    544
```

FIG. 4A

```
                                                                              50
BGS-19    (1)  MLILPVLGA-----GSNKDPSYSLQVQRQVPEGCVIVSCNLS
siglec-6  (1)  -MPLLLLPILWA-----GALAMDPNFWLQVCESVTVQEGLCVLVPCTFF
siglec-7  (1)  -MLLLLLPLLWGREVEGQKSNRKDYSLTMQSSVTVQEGMCVHVRCSFS
siglec-10 (1)  -MLLPLLLSSLLG-----GSQAMDGRFWIRVQESVMVPEGLCISVPCSFS
                       Signal peptide            Ig-like domain 1
                                                                              100
BGS-19   (46)  YPRDGWDESTAAYGYWFKGRTSPKTGAPVATNNQSREVEMSTRDRFQLTG
siglec-6 (45)  HEIPYYDKNSPVHGYWFREGAIISGDSPVATNKLDQEVQEETQGRFRLLG
siglec-7 (50)  YPVDSQTDSDPVHGYWFRAGNDISWKAPVATNNPAWAVQEETRDRFHLIG
siglec-10(45)  YPRQDWTGSTPAYGYWFKAVTETTKGAPVATNHQSREVEMSTRGRFQLTG
                                                                              150
BGS-19   (96)  DPGKGSCSLVIRDAQREDEAWYFFRVERGSR------VRHSFLSNA
siglec-6 (95)  DSRNNCSLSIVDARRRDNGSYFFRMERGS--------TKYSYKSPQ
siglec-7(100)  DPQTKNCTLSIRDARMSDAGRYFFRMEKGNIKWNYKYDQLSVNVTDPPQN
siglec-10(95)  DPAKGNCSLVIRDAQMQDESQYFFRVERGSY------VRYNFMNDG
```

FIG. 4B

```
              151                                                   200
BGS-19   (136) FELKVTALTKKPDVYIPETLEPGQPVTVICVENWAEKKCPAPSFSWTGAA
siglec-6 (134) LSVHVTDLTHRPKILIPGTLEPGHSKNLTCSVSWACEQGTPPIESWLSAA
siglec-7 (150) LTVTVFQGEGTASTALGNSSSLVLEGQSLRLVCAVDSNPPARLSWTWRS
siglec-10(135) FELKVTALTQKPDVYIPETLEPGQPVTVICVENWAFECPPPSFSWTGAA
                              ─────── Ig-like domain 2 ───────
              201                                                   250
BGS-19   (186) LSPRRTRPSTSQPSDPGVLELPPIQMEHEGEFTCHAQHPLGSQHVSLSLS
siglec-6 (184) PTSLGPRTTHS-------SVLIITPRPQDHGTNLTCQVKFAGAGVTTERTIQ
siglec-7 (200) LTLYPSQPSNP-------LVLELQVHLGDEGEFTCRAQNSLGSQHVSLNLS
siglec-10(185) LSSQGTKPTTS-------HFSVLSFTPRPQDHNTDLTCHVDESRKGVSVQRTVR
              251                                                   300
BGS-19   (236) VHWKLEHGG-------------------------------------------
siglec-6 (229) LNVTYVPQNPT-----------------------------------------
siglec-7 (244) LQQEYTGKMRPV----------------------------------------
siglec-10(232) LRVAYAPRDLVISISRDNTPALEPQPQGNVPYLEAQKGQFLRLLCAADSQ
```

FIG. 4C

```
BGS-19    (245)                                                  350
siglec-6  (240)  ----------------------------------------------------
siglec-7  (256)  ----------------------------------------------------
siglec-10 (282)  PPATLSWVLQNRVLSSSHPWGPRPLGLELPGVKAGDSGRYTCRAENRLGS BGS-19    (245)                                                  400
siglec-6  (240)  ----------------------------------------------------
siglec-7  (256)  ----------------------------------------------------
siglec-10 (332)  QQRALDLSVQYPPENLRVMVSQANRTVLENLGNGTSLPVLEGQSLCLVCV BGS-19    (245)                                                  450
siglec-6  (240)  ----------------------------------------------------
siglec-7  (256)  ----------------------------------------------------
siglec-10 (382)  THSSPPARLSWTQRGQVLSPSQPSDPGVLELPRVQVEHEGEFTCHARHPL
```

FIG. 4D

```
                                                                        500
BGS-19    (245)  ------------------------------------------------------
siglec-6  (240)  ------------------------------------------------------
siglec-7  (256)  ------------------------------------------------------
siglec-10 (432)  GSQHVSLSLSVHYSPKLLGPSCSWEAEGLHCSCSSQASPAPSLRWWLGEE 550
BGS-19    (245)  ------------------------------------------------------
siglec-6  (240)  ------------------------------------------------------
siglec-7  (256)  -----------------------------------------------------T
siglec-10 (482)  LLEGNSSQDSFEVTPSSAGPWANSSLSHGGLSSGLRLRCEAWNVHGAQS 600
BGS-19    (245)  -------------GLGIGAALGAGVAALLAFCSCLVVHRVKIGRKEAR
siglec-6  (241)  GIFPGDGSGKQETRAGLVHGAGVTALLADCLIEIVKTHRRKAA
siglec-7  (256)  ---------SGVLLGAVGGAGATALVFLSFCVIEIVVRSCRKKSA
siglec-10 (532)  GSILQLPDKKGLISTAFSNGAFLGIGITALIFLCIALIIMKILPKRRTQT
                              ────────────────────────────────
                              Transmembrane domain
```

FIG. 4E

```
              601
BGS-19   (280) KRAAAEQDVPSTL------------GPISQG-HQHECSAGSSQDHPPPGAAT
siglec-6 (291) RTAVGSNDTHPTT------------GSASPK-HQKNSKLHGPTETSSCSGAA
siglec-7 (292) RPAADVGDIGMKD------------ANTIRGSAS----QGNLTESWADDNPRHHGLA
siglec-10(582) ETPRPRFSRHSTILDYINVVPTAGPLAQKRNQKATPNSPRTPLPPGAPSP
                                                          650

651                                                700
BGS-19   (319) YTPGKG-------------------EEQ-ELHYASLSQQGLRLWEPA
siglec-6 (330) PTV----------------------EMDEELHYASLNHGMNPSKDT
siglec-7 (333) AHSS---------------------GEEREIQYAPLSEHKGEPQDLS
siglec-10(632) ESKKNQKKQYQLPSFPEPKSSTQAPESQEELHYATLNFPGVRPRPEA
                                             ITIM domain 701                              739
BGS-19   (346) DQEAPSTTEYSEIKIHTGQPLRGPGFGLQLEREMSGMVP
siglec-6 (355) STEYSEVRTQ-----------------------------
siglec-7 (359) GQEATNNEYSEIKIPK-----------------------
siglec-10(682) RMPKGTQADYAEVKFQ-----------------------
```

POLYNUCLEOTIDES ENCODING A HUMAN CELL SURFACE PROTEIN WITH IMMUNOGLOBULIN FOLDS, BGS-19

This application claims benefit to provisional application U.S. Ser. No. 60/368,422 filed Mar. 28, 2002, under 35 U.S.C. 119(e). The entire teachings of the referenced application are incorporated herein by reference.

FIELD OF THE INVENTION

The present invention relates to BGS-19, a novel human cell surface receptor in the immunoglobulin superfamily ("IgSF"). In particular, the invention relates to BGS-19 polynucleotides, polypeptides, agonists, antagonists, and variants thereof. The invention also relates to pharmaceutical compositions comprising BGS-19 polynucleotides, polypeptides, agonists or antagonists.

The invention also relates to methods for detecting, identifying and measuring compounds that bind, inhibit and/or activate BGS-19 polynucleotides and polypeptides. The invention also relates to methods for measuring the amount or degree of such binding. The invention also relates to methods of synthesizing the compositions of the invention.

The invention also relates to methods for preventing or treating disorders related to BGS-19 (e.g., cancer, immune-related disorders, developmental disorders), comprising administering to a patient in need of such treatment a composition of the invention. The invention also relates to methods for diagnosing disorders related to BGS-19. The invention also relates to methods for monitoring the progression of disorders, and methods for assessing treatment efficacy.

BACKGROUND

Many identified cell-surface antigens and receptors are members of the immunoglobulin superfamily ("IgSF"). IgSF proteins are characterized by one or more disulfide-linked loops formed between a highly conserved and properly spaced pair of cysteine residues, which organizes two β sheets composed of seven or nine antiparallel β-strands. These loops, which are referred to as immunoglobulin-like domains, are classified as variable or constant immunoglobulin-type domains. The variable (or V-type domains) polynucleotiderally possess disulfide loops with cysteine residues spaced by 65–75 amino acids and thus accommodate nine antiparallel β-strands whereas the constant (or C-type) domains typically exhibit intercysteine distances of 35–55 residues, and thus accommodate only seven antiparallel β-strands. Although some IgSF members contain multiple domains of a single type (e.g., NCAM which has five C2-type domains), most members possess either a single immunoglobulin-type domain or a mixture of both V-type and C-type domains (Williams and Barclay, 1988 "The immunoglobulin superfamily—domains for cell surface recognition", Annu Rev Immunol. 6:381–405).

IgSF proteins are known to function as antigen receptors, cytokine receptors, receptors for cell-surface molecules (e.g., other IgSF proteins, adhesion molecules), and as counter-receptors.

SUMMARY OF THE INVENTION

The present invention relates to BGS-19 polynucleotides, polypeptides, antagonists, agonists, and variants thereof, and optionally, a pharmaceutically acceptable carrier. Accordingly, the present invention provides compositions comprising agonists or antagonists of a BGS-19 polynucleotide, BGS-19 polypeptide, or of complexes comprising a BGS-19 polynucleotide or BGS-19 polypeptide. Compositions comprising activators and inhibitors of such agonists and antagonists are also encompassed by the present invention.

The present invention also relates to vectors, recombinant cells, and transgenic animals expressing a BGS-19 polynucleotide, polypeptide, antagonist, agonist, or a variant thereof. In particular embodiments, the vectors comprise a polynucleotide sequence of the invention. In other embodiments, the polynucleotidetically engineered host cells comprise a polynucleotide sequence of the invention. In other embodiments, the transgenic animals comprise a polynucleotide sequence of the invention. In further embodiments of the above, the polynucleotide sequence is operatively associated with a regulatory element that directs the expression of the polynucleotide sequence. In a specific embodiment, the regulatory element is a tissue-specific promoter, inducible promoter, non-inducible promoter, enhancer or operator.

The present invention also relates to screening assays particularly useful in drug discovery efforts. Thus, the invention provides methods for screening for compounds that bind and/or modulate a BGS-19 polynucleotide or polypeptide. Accordingly, in one embodiment, the invention provides a method for detecting an analyte that binds a BGS-19 polypeptide comprising the steps of contacting the BGS-19 polypeptide, or a variant thereof, with an analyte under conditions that allow the BGS-19 polypeptide to be bound by the analyte, and detecting binding of the BGS-19 polypeptide to the analyte, wherein detection of binding indicates presence of an analyte that binds the BGS-19 polypeptide. In particular embodiments, such methods can be used to detect and identify compounds that bind or affect the pharmacokinetics (e.g., catalytic activity) of a polypeptide of the invention.

In particular embodiments, the analyte is a protein. Accordingly, in one embodiments, the present invention provides a method for identifying a BGS-19-binding protein comprising the steps of contacting a BGS-19 polypeptide, or a variant thereof, with an array comprising a plurality of proteins, and detecting binding of the BGS-19 polypeptide to a protein on the array, wherein detection of binding indicates presence of a BGS-19-binding protein.

The present invention also relates to methods for detecting an analyte that binds a BGS-19 polynucleotide comprising the steps of contacting the BGS-19 polynucleotide, or a variant thereof, with an analyte under conditions that allow the BGS-19 polynucleotide to be bound by the analyte, and detecting binding of the BGS-19 polynucleotide to the analyte, wherein detection of binding indicates presence of an analyte that binds the BGS-19 polynucleotide. In particular embodiments, such methods can be used to detect and identify compounds that modulate transcription or translation of a BGS-19 polynucleotide product.

In particular embodiments, the present invention provides methods for detecting and identifying proteins that bind BGS-19 DNA sequences, such proteins including, but not limited to, proteins that affect DNA conformation and proteins that modulate transcriptional activity (e.g., transcription factors, proteins that bind enhancers). In particular embodiments, the present invention provides methods for detecting and identifying factors that bind BGS-19 RNA sequences, such factors including, but not limited to, proteins, steroid hormones, or other small molecules. In further embodiments, the BGS-19 RNA-binding factors modulate translational efficacy and/or affect RNA stability.

The present invention also relates to methods for detecting and identifying BGS-19 agonists, antagonists, as well as activators and inhibitors thereof. In specific non-limiting embodiments, BGS-19 agonists, BGS-19 antagonists, inhibitors of BGS-19 agonists, activators of BGS-19 agonists, inhibitors of BGS-19 antagonists and activators of BGS-19 antagonists are small molecules (i.e., less than 500 daltons) that bind a BGS-19 polynucleotide or BGS-19 polypeptide of the invention.

The present invention also relates to methods for screening for proteins that bind specific domains of a BGS-19 polypeptide, wherein the domains exhibit a biological activity. In one embodiment, the invention provides a method for identifying a protein having a SH2 domain comprising the steps of contacting a SH2-binding domain of a BGS-19 polypeptide, or a variant thereof, with an analyte under conditions that allow the SH2-binding domain to be bound by the analyte, and detecting binding of the SH2-binding domain to the analyte, wherein detection of binding indicates the presence of a protein having a SH2 domain. In a further embodiment, the SH2-binding domain of the BGS-19 protein comprises an immunotyrosine-based inhibition motif ("ITIM").

The present invention also relates to methods for synthesizing a BGS-19 polynucleotide, polypeptide, antagonist, agonist, or a variant thereof, comprising the steps of culturing a recombinant cell comprising a BGS-19 polynucleotide, or a variant thereof, under conditions that allow the BGS-19 polynucleotide to be expressed by the cell, and optionally, isolating the expressed BGS-19 polynucleotide.

The present invention also relates to methods for preventing or treating a BGS-19-related disorder (e.g., cancer), comprising administering to a subject in need thereof an effective amount of a BGS-19 polynucleotide, polypeptide, antagonist, agonist, inhibitor of a BGS-19 agonist, activator of a BGS-19 agonist, inhibitor of a BGS-19 antagonist, activator of a BGS-19 antagonist, or a variant thereof, and optionally, a pharmaceutically acceptable carrier. In one embodiment, the method comprises administering an expression vector that expresses a BGS-19 polynucleotide, polypeptide, antagonist or agonist. In another embodiment, the method comprises administering a recombinant cell that expresses a BGS-19 polynucleotide, polypeptide, antagonist or agonist. In particular embodiments, the BGS-19-related disorder is cancer, an immune-related disorder, or a developmental disorder.

The present invention also relates to methods for diagnosing, staging, determining a prognosis of, or monitoring the progression of a BGS-19-related disorder, comprising determining a level of BGS-19 polynucleotide or BGS-19 polypeptide expression in a biological sample.

Accordingly, the present invention relates to methods for diagnosing a BGS-19-related disorder comprising detecting in a biological sample from a subject a BGS-19 polynucleotide or BGS-19 polypeptide. In one embodiment, the method comprises the steps of contacting a compound that binds a BGS-19 polypeptide with a patient sample, suspected of containing the BGS-19 polypeptide, under conditions that allow the BGS-19 polypeptide to be bound by the compound, and detecting or measuring binding of the compound to the BGS-19 polypeptide, wherein detection or measurement of binding indicates presence or amount, respectively, of the BGS-19 polypeptide, and wherein the BGS-19-related disorder is determined to be present when the presence or amount of detected BGS-19 polypeptide differs from a control value representing the amount of BGS-19 polypeptide present in an analogous sample from a subject not having the BGS-19-related disorder.

The present invention also relates to methods for establishing a prognosis for a BGS-19-related disorder comprising the steps of contacting a compound that binds a BGS-19 polypeptide with a patient sample, suspected of containing the BGS-19 polypeptide, under conditions that allow the BGS-19 polypeptide to be bound by the compound, and detecting or measuring binding of the compound to the BGS-19 polypeptide, wherein detection or measurement of binding indicates presence or amount, respectively, of the BGS-19 polypeptide, and wherein the stage of the BGS-19-related disorder is determined when the presence or amount of detected BGS-19 polypeptide is compared with the amount of BGS-19 polypeptide present in an analogous sample from a subject having a particular stage of the BGS-19-related disorder.

The present invention also relates to methods for inhibiting natural killer cell cytotoxic activity comprising the steps of contacting a BGS-19 polynucleotide or BGS-19 polypeptide with a natural killer cell, and measuring cytotoxic activity of the natural killer cell.

The invention further relates to a method for preventing, treating, or ameliorating a medical condition with the polypeptide provided as SEQ ID NO:2, in addition to, its encoding nucleic acid, or a modulator thereof, wherein the medical condition is ovarian cancer or related proliferative condition of the ovary.

The invention further relates to a method of diagnosing a pathological condition or a susceptibility to a pathological condition in a subject comprising the steps of (a) determining the presence or amount of expression of the polypeptide of of SEQ ID NO:2 in a biological sample; (b) and diagnosing a pathological condition or a susceptibility to a pathological condition based on the presence or amount of expression of the polypeptide relative to a control, wherein said condition is a member of the group consisting of ovarian cancer or related proliferative condition of the ovary.

The present invention also relates to drug delivery means and therapeutic regimens for the compositions of the invention. In particular embodiments, the compositions of the invention are administered to a subject by polynucleotide therapy. In other embodiments, the compositions are administered to a subject in a combination therapy regimen.

The present invention also relates to kits comprising a BGS-19 polynucleotide, polypeptide, antagonist, agonist, inhibitor of a BGS-19 agonist, and/or inhibitor of a BGS-19 antagonist, and optionally, detection means to detect and/or measure binding interactions of such compounds.

The present invention also relates to an isolated polynucleotide consisting of the nucleotide sequence of the human BGS-19 polynucleotide.

The present invention also relates to an isolated polynucleotide consisting of the coding region of the human BGS-19 polynucleotide.

The present invention also relates to an isolated polynucleotide consisting of a portion of the human BGS-19 polynucleotide consisting of at least 8 bases, specifically excluding Genbank Accession Nos. gi|BI518708, gi|BF308356, gi|BF205116, gi|BF969219, gi|BG826221, and/or gi|AA341128.

The present invention also relates to an isolated polynucleotide consisting of a nucleotide sequence complementary to a portion of the human BGS-19 polynucleotide.

The present invention also relates to an isolated polynucleotide consisting of a nucleotide sequence that hybridizes to a nucleotide sequence complementary to the coding region of the human BGS-19 polynucleotide.

The present invention also relates to an isolated polynucleotide consisting of a nucleotide sequence that hybridizes to the nucleotide sequence of a human BGS-19 mRNA.

The invention further relates to an isolated nucleic acid molecule of SEQ ID NO:1, wherein the nucleotide sequence comprises sequential nucleotide deletions from either the C-terminus or the N-terminus. Such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

The present invention also relates to an isolated polynucleotide consisting of a nucleotide sequence encoding a fragment of the human BGS-19 protein, wherein said fragment displays one or more functional activities specifically excluding Genbank Accession Nos. gi|BI518708, gi|BF308356, gi|BF205116, gi|BF969219, gi|BG826221, and/or gi|AA341128.

The present invention also relates to an isolated polynucleotide consisting of a nucleotide sequence encoding a domain of a human BGS-19 polypeptide, wherein said domain is selected from the group consisting of a signal sequence, transmembrane domain, extracellular domain, cytoplasmic domain, glycosylation site, phosphorylation site, ITIM domain, and immunoglobulin domain specifically excluding Genbank Accession Nos. gi|BI518708, gi|BF308356, gi|BF205116, gi|BF969219, gi|BG826221, and/or gi|AA341128.

The present invention also relates to an isolated polynucleotide consisting of a fragment of the human BGS-19 polynucleotide, wherein the polynucleotide sequence encodes a chimeric protein.

The present invention also relates to the polynucleotide of SEQ ID NO:1 and consisting of 10 to 50 bases specifically excluding Genbank Accession Nos. gi|BI518708, gi|BF308356, gi|BF205116, gi|BF969219, gi|BG826221, and/or gi|AA341128.

The present invention also relates to the polynucleotide of SEQ ID NO:1 and consisting of 15 to 100 bases specifically excluding Genbank Accession Nos. gi|BI518708, gi|BF308356, gi|BF205116, gi|BF969219, gi|BG826221, and/or gi|AA341128.

The present invention also relates to the polynucleotide of SEQ ID NO:1 and consisting of 100 to 1000 bases specifically excluding Genbank Accession Nos. gi|BI518708, gi|BF308356, gi|BF205116, gi|BF969219, gi|BG826221, and/or gi|AA341128.

The present invention also relates to an isolated RNA encoding a human BGS-19 polypeptide.

The present invention also relates to a purified human BGS-19 polypeptide.

The present invention also relates to a purified human BGS-19 polypeptide consisting of the amino acid sequence substantially as set forth in SEQ ID NO:2.

The present invention also relates to a purified fragment of a human BGS-19 polypeptide consisting of a domain of a human BGS-19 polypeptide, wherein said domain is selected from the group consisting of a signal sequence, transmembrane domain, extracellular domain, cytoplasmic domain, glycosylation site, phosphorylation site, IMAN domain, and immunoglobulin domain specifically excluding Genbank Accession Nos. gi|BI518708, gi|BF308356, gi|BF205116, gi|BF969219, gi|BG826221, and/or gi|AA341128.

The present invention also relates to a polypeptide consisting of an amino acid sequence that has at least 60% identity to a purified fragment of a human BGS-19 polypeptide consisting of a domain of a human BGS-19 polypeptide, wherein said domain is selected from the group consisting of a signal sequence, transmembrane domain, extracellular domain, cytoplasmic domain, glycosylation site, phosphorylation site, IMAN domain, and immunoglobulin domain, wherein the percent identity is determined over an amino acid sequence of identical size to the domain specifically excluding Genbank Accession Nos. gi|BI518708, gi|BF308356, gi|BF205116, gi|BF969219, gi|BG826221, and/or gi|AA341128.

The present invention also relates to a polypeptide consisting of an amino acid sequence that has at least 90% identity to a purified fragment of a human BGS-19 polypeptide consisting of a domain of a human BGS-19 polypeptide, wherein said domain is selected from the group consisting of a signal sequence, transmembrane domain, extracellular domain, cytoplasmic domain, glycosylation site, phosphorylation site, IMAN domain, and immunoglobulin domain, wherein the percent identity is determined over an amino acid sequence of identical size to the domain specifically excluding Genbank Accession Nos. gi|BI518708, gi|BF308356, gi|BF205116, gi|BF969219, gi|BG826221, and/or gi|AA341128.

The present invention also relates to a chimeric protein consisting of an amino acid sequence that has at least 90% identity to a purified fragment of a human BGS-19 polypeptide consisting of a domain of a human BGS-19 polypeptide, wherein said domain is selected from the group consisting of a signal sequence, transmembrane domain, extracellular domain, cytoplasmic domain, glycosylation site, phosphorylation site, IMAN domain, and immunoglobulin domain, wherein the percent identity is determined over an amino acid sequence of identical size to the domain specifically excluding Genbank Accession Nos. gi|BI518708, gi|BF308356, gi|BF205116, gi|BF969219, gi|BG826221, and/or gi|AA341128, and further consisting of a first polypeptide of at least six amino acids fused, via a covalent bond, to second polypeptide.

The present invention also relates to an antibody that immunospecifically binds to a human BGS-19 polypeptide.

The present invention also relates to a compound consisting of a fragment of an antibody that immunospecifically binds to a human BGS-19 polypeptide.

The present invention also relates to an expression vector containing of a BGS-19 polynucleotide.

The present invention also relates to a recombinant cell containing a recombinant BGS-19 polynucleotide.

The present invention also relates to a transgenic non-human animal, wherein a BGS-19 polynucleotide is expressed as a transpolynucleotide.

The present invention also relates to pharmaceutical composition comprising a therapeutically effective amount of a BGS-19 polynucleotide, and a pharmaceutically acceptable carrier.

The present invention also relates to a pharmaceutical composition comprising a therapeutically effective amount of a BGS-19 polypeptide, and a pharmaceutically acceptable carrier.

The present invention also relates to a pharmaceutical composition comprising a therapeutically effective amount of an antibody that immunospecifically binds to a BGS-19 polypeptide, and a pharmaceutically acceptable carrier.

The present invention also relates to a method for synthesizing a BGS-19 polypeptide comprising the steps of: (a) culturing a recombinant cell containing a BGS-19 polynucleotide under conditions that allow the BGS-19 polypeptide to be expressed by the cell; and (b) isolating the expressed BGS-19 polypeptide. The present invention also relates to the product produced by this process.

The present invention also relates to a method for preventing or treating a BGS-19-related disorder, the method comprising administering to a subject in need thereof an amount of the pharmaceutical composition of the present invention effective for preventing or treating the BGS-19-related disorder.

The present invention also relates to a method for preventing or treating a BGS-19-related disorder, the method comprising administering to a subject in need thereof an amount of the expression vector of the present invention effective for preventing or treating the BGS-19-related disorder.

The present invention also relates to a method for diagnosing a BGS-19-related disorder in a subject comprising the steps of: (a) contacting a BGS-19 antibody with a sample, suspected of containing a BGS-19 polypeptide, from the subject under conditions that allow the BGS-19 polypeptide to be bound by the BGS-19 antibody; and (b) detecting or measuring binding of the BGS-19 antibody to the BGS-19 polypeptide; wherein detection or measurement of binding indicates presence or amount, respectively, of the BGS-19 polypeptide; and wherein the BGS-19-related disorder is determined to be present when the presence or amount of detected BGS-19 polypeptide differs from a control value representing the amount of BGS-19 polypeptide present in an analogous sample from a subject not having the BGS-19-related disorder.

The present invention also relates to a method for staging a BGS-19-related disorder in a subject comprising the steps of: (a) contacting a BGS-19 antibody with a sample, suspected of containing a BGS-19 polypeptide, from the subject under conditions that allow the BGS-19 polypeptide to be bound by the BGS-19 antibody; and (b) detecting or measuring binding of the BGS-19 antibody to the BGS-19 polypeptide; wherein detection or measurement of binding indicates presence or amount, respectively, of the BGS-19 polypeptide; and wherein the stage of a BGS-19-related disorder in a subject is determined when the presence or amount of detected BGS-19 polypeptide is compared with the amount of BGS-19 polypeptide present in an analogous sample from a subject having a particular stage of a BGS-19-related disorder.

The present invention also relates to a method for identifying an analyte that binds a BGS-19 polypeptide comprising the steps of: (a) contacting the BGS-19 polypeptide with an analyte under conditions that allow the BGS-19 polypeptide to be bound by the analyte; and (b) detecting binding of the BGS-19 polypeptide to the analyte; wherein detection of binding indicates presence of an analyte that binds the BGS-19 polypeptide.

The present invention also relates to a method for identifying a protein that binds a BGS-19 polypeptide comprising the steps of: (a) contacting the BGS-19 polypeptide with a positionally addressable array comprising a plurality of proteins, with each protein being at a different position on a solid support; and (b) detecting binding of the BGS-19 polypeptide to a protein on the array; wherein detection of binding indicates presence of a protein that binds the BGS-19 polypeptide.

The present invention also relates to a method for identifying a polypeptide having a SH2 domain comprising the steps of: (a) contacting a SH2-binding domain of the BGS-19 protein with an analyte under conditions that allow the SH2-binding domain to be bound by the analyte; and (b) detecting binding of the SH2-binding domain to the analyte; wherein detection of binding indicates a polypeptide having a SH2 domain.

The present invention also relates to a method for identifying an inhibitor of natural killer cell cytotoxic activity comprising the steps of: (a) contacting a BGS-19 polypeptide with a natural killer cell; and (b) measuring cytotoxic activity of a natural killer cell, wherein inhibition of cytotoxic activity indicates the presence of an inhibitor of natural killer cell cytotoxic activity.

The present invention also relates to a kit comprising: (a) in a first container, a purified BGS-19 polypeptide; (b) in a second container, a first compound that binds the polypeptide; and (c) a solid support having a second, different compound attached thereto; wherein the second compound binds the polypeptide when the polypeptide is bound to the first compound. The present invention also relates to a kit further comprising a detection means to detect the first compound when bound to the polypeptide.

Definitions

As used herein, the phrase "BGS-19 polynucleotide", "BGS-19 nucleic acid", "polynucleotide of the invention", or "nucleic acid of the invention" refers to a polynucleotide derived from the nucleotide sequence of SEQ ID NO:1 and depicted in FIGS. 1A–C, a complementary sequence thereof, and variants thereof. BGS-19 polynucleotides include, but are not limited to, DNA molecules (e.g., cDNA, genomic DNA), RNA molecules (e.g., hnRNA, pre-mRNA, mRNA), and variants thereof. BGS-19 polynucleotides also encompass sense and antisense sequences, as well as single-stranded and double-stranded molecules. BGS-19 polynucleotides preferably are polynucleotides of at least fifteen nucleic acids in length.

As used herein, the phrase "BGS-19 polypeptide" or "polypeptide of the invention" refers to a polypeptide encoded by a BGS-19 polynucleotide, and variants thereof. BGS-19 polypeptides encompass proteins and peptides, and preferably are of at least six amino acids in length.

As used herein, a "naturally occurring" polynucleotide refers to an RNA or DNA molecule having a nucleotide sequence that occurs in nature (e.g., encodes a natural protein).

As used herein, the term "variant" or "variants" refers to, where appropriate, variations of the nucleic acid or amino acid sequence of BGS-19 molecules such as, but not limited to, homologs, analogs, derivatives, fragments, hybrids, mimetics, conpolynucleotiders, and nucleotide and amino acid substitutions, additions, deletions, or other chemical modifications.

As used herein, the term "fragment" or "fragments" as used herein refers to a polypeptide having an amino acid sequence of at least 10 contiguous amino acid residues, at least 15 contiguous amino acid residues, at least 20 contiguous amino acid residues, at least 25 contiguous amino acid residues, or at least 30 contiguous amino acid residues of the amino acid sequence of a BGS-19 polypeptide. Polypeptide fragments may also be at least 40 contiguous amino acid residues, at least 50 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 200 contiguous amino acid residues, at least 250 contiguous amino acid residues, or at least 300 contiguous amino acid residues, at least 350 contiguous amino acid residues. Preferably such fragments retain the biological activity of the native full-length polypeptide.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

As used herein, the phrase "isolated polynucleotide" refers to a polynucleotide which is separated from other polynucleotides which are present in the natural source of the polynucleotide. Preferably, an isolated polynucleotide is free of sequences (preferably protein encoding sequences) which naturally flank the polynucleotide (i.e., sequences located at the 5' and 3' ends of the polynucleotide) in the genomic DNA of the organism from which the polynucleotide is derived. In other embodiments, the isolated polynucleotide is free of intron sequences. For example, in various embodiments, the isolated polynucleotide can contain less than about 5 kB, 4 kB, 3 kB, 2 kB, 1 kB, 0.5 kB or 0.1 kB of nucleotide sequences which naturally flank the polynucleotide in genomic DNA of the cell from which the polynucleotide is derived. Moreover, an isolated polynucleotide, such as a cDNA molecule, can be substantially free of other cellular material, or culture medium when produced by recombinant techniques, or substantially free of chemical precursors or other chemicals when chemically synthesized. In one embodiment, the polynucleotides of the invention comprise a contiguous open reading frame encoding a polypeptide of the invention. As used herein, an isolated polynucleotide does not include an isolated chromosome, and does not include the poly(A) tail of an mRNA, if present.

As used herein, the phrase "isolated polypeptide" refers to a polypeptide that is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the polypeptide, or fragment thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest. In preferred embodiments, purified or isolated preparations will lack any contaminating proteins from the same animal from which the protein is normally produced, as can be accomplished by recombinant expression of, for example, a human protein in a non-human cell.

As will be appreciated by the skilled practitioner, should the amino acid fragment comprise an antigenic epitope, for example, biological function per se need not be maintained. The terms BGS-19 polypeptide and BGS-19 protein are used interchangeably herein to refer to the encoded product of the BGS-19 nucleic acid sequence according to the present invention.

It is another aspect of the present invention to provide modulators of the BGS-19 protein and BGS-19 peptide targets which can affect the function or activity of BGS-19 in a cell in which BGS-19 function or activity is to be modulated or affected. In addition, modulators of BGS-19 can affect downstream systems and molecules that are regulated by, or which interact with, BGS-19 in the cell. Modulators of BGS-19 include compounds, materials, agents, drugs, and the like, that antagonize, inhibit, reduce, block, suppress, diminish, decrease, or eliminate BGS-19 function and/or activity. Such compounds, materials, agents, drugs and the like can be collectively termed "antagonists". Alternatively, modulators of BGS-19 include compounds, materials, agents, drugs, and the like, that agonize, enhance, increase, augment, or amplify BGS-19 function in a cell. Such compounds, materials, agents, drugs and the like can be collectively termed "agonists".

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

As used herein, the term "vector" refers to a polynucleotide capable of transporting another polynucleotide to which it has been linked. One type of vector is a "plasmid", which refers to a circular double stranded DNA loop into which additional DNA segments can be ligated. Another type of vector is a viral vector, wherein additional DNA segments can be ligated into the viral genome.

As used herein, the term "biological sample" refers to a cell, tissue, organ, multicellular organism, biological fluid (e.g., blood), or preparation (e.g., extract) thereof. A biological sample can be derived, for example, from cells or tissue cultures in vitro. A biological sample also can be derived from a living organism or from a population of single cell organisms.

As used herein, the phrase "BGS-19-related disorder" refers to a disease that involves regulation of the BGS-19 polynucleotide, (e.g., diseases involving cells expressing BGS-19 polynucleotide, particularly diseases involving above-normal or unregulated expression of BGS-19 polynucleotide). BGS-19-related disorders include, but are not limited to, cancer (e.g., adenocarcinoma, leukemia, lymphoma, melanoma, myeloma, sarcoma, teratocarcinoma, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus), immune-related disorders (e.g., acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency ("CVI"), DiGeorge's syndrome (thymic hypoplasia), thymic dysplasia, isolated IgA deficiency, severe combined immunodeficiency disease ("SCID"), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease), and developmental disorders (e.g., renal tubular acidosis, anemia, Cushing's syndrome, achondroplastic dwarfism, Duchenne and Becker muscular dystrophy, epilepsy, gonadal dyspolynucleotidesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss). BGS-19-related disorders also include, but are not limited to, any disorders associated with cell growth, disorders associated with cell differentiation, disorders associated with embryopolynucleotidesis, and disorders associated with morphopolynucleotidesis involving any tissue, organ, and/or system (e.g., the brain, adrenal gland, kidney, skeletal or reproductive system) of a subject.

As used herein, the phrase "hybridizes under stringent conditions" is intended to describe conditions for hybridization and washing under which nucleotide sequences at least 60% (65%, 70%, 75%, 80% or preferably 85% or more) identical to each other typically remain hybridized to each other. Such stringent conditions are known to those skilled in the art and can be found in *Current Protocols in Molecular Biology*, John Wiley & Sons, N.Y. (1989) pp. 6.3.1–6.3.6, which describes aqueous and non-aqueous methods, either of which can be used. Another preferred, non-limiting example of stringent hybridization conditions are hybridization in 6× sodium chloride/sodium citrate ("SSC") at about 45_C, followed by one or more washes in 2.0×SSC at 50° C. (low stringency) or 0.2×SSC, 0.1% SDS at 50–65_C (high stringency). Another preferred example of stringent hybridization conditions are hybridization in 6× sodium chloride/sodium citrate (SSC) at about 45° C., followed by one or more washes in 0.2× SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. In one embodiment, an isolated nucleic acid molecule of the invention that hybridizes under stringent conditions to the sequence of the BGS-19 nucleic acid, or a complement thereof, corresponds to a naturally-occurring nucleic acid molecule.

As used herein, the phrase "BGS-19 polynucleotide expression" refers to transcription of a BGS-19 polynucleotide that produces BGS-19 pre-mRNA, BGS-19 mRNA, and/or translation of BGS-19 mRNA to produce BGS-19 protein.

As used herein, the phrase "therapeutic" or "therapeutic agent" refers to a molecule or compound that assists in the treatment of a disease. As such, a cancer therapeutic is a molecule or compound that aids in the treatment of tumors or cancer. A treatment protocol includes, but is not limited to, administration of therapeutic agents, radiation therapy, dietary therapy, physical therapy, and psychological therapy. Cancer therapeutics also encompass a molecule or compound that aids in the prevention of tumors or cancer, prevents the recurrence of tumors or cancer, or prevents the spread or metastasis of tumors or cancer.

As used herein, the phrase "pharmaceutically acceptable" refers to an agent that does not interfere with the effectiveness of the biological activity of an active ingredient, and which may be approved by a regulatory agency of the Federal government or a state government, or is listed in the U.S. Pharmacopeia or other polynucleotiderally recognized pharmacopeia for use in animals, and more particularly for use in humans. Accordingly, suitable pharmaceutically acceptable carriers include agents that do not interfere with the effectiveness of a pharmaceutical composition.

As used herein, the term "carrier" refers to a diluent, adjuvant, excipient, or vehicle. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions.

BRIEF DESCRIPTION OF THE FIGURES

FIGS. 1A–C show the full-length polynucleotide sequence (SEQ ID NO:1) and deduced amino acid sequence (SEQ ID NO:2) of the novel human cell surface protein with immunoglobulin folds, BGS-19, of the present invention. The standard one-letter abbreviation for amino acids is used to illustrate the deduced amino acid sequence. The polynucleotide sequence contains a sequence of 1985 nucleotides (SEQ ID NO:1), encoding a polypeptide of 385 amino acids (SEQ ID NO:2). An analysis of the BGS-19 polypeptide determined that it comprised the following features: a putative signal sequence located from about amino acid 1 to about amino acid 15 of SEQ ID NO:2 represented by single underlining; a predicted transmembrane domain located from about amino acid 250 to about amino acid 275 (SEQ ID NO:8) of SEQ ID NO:2 represented by double underlining; two Ig-like domains located from about amino acid 16 to about amino acid 113 (Ig-like domain 1; SEQ ID NO:9) of SEQ ID NO:2, and located from about amino acid 140 to about amino acid 241 (Ig-like domain 2; SEQ ID NO:10) of SEQ ID NO:2 represented by light shading; and a predicted ITIM domain located from about amino acid 329 to about amino acid 334 of SEQ ID NO:2 represented by dark shading.

FIGS. 2A–B show the partial polynucleotide sequence (SEQ ID NO:3) and deduced amino acid sequence (SEQ ID NO:4) of the novel human cell surface protein with immunoglobulin folds, BGS-19, of the present invention. The standard one-letter abbreviation for amino acids is used to illustrate the deduced amino acid sequence. The polynucleotide sequence contains a sequence of 1632 nucleotides (SEQ ID NO:3), encoding a polypeptide of 544 amino acids (SEQ ID NO:4).

FIGS. 4A–E. Sequence alignment among BGS-19, Siglec-6 (SEQ ID NO:5), Siglec-7 (SEQ ID NO:6), and Siglec-10 (SEQ ID NO:7) amino acid sequences (Siglec-6 GenBank accession number: NP_001763, Siglec-10 GenBank accession number: NP_149121). Sequence homology between BGS-19 and Siglec-6 is 41.4% identity and 48.0% similarity. Sequence homology between BGS-19 and Siglec-7 is 44.7% identity and 50.8% similarity. Sequence homology between BGS-19 and Siglec-10 is 46.6% identity and 51.7% similarity. Signal peptide region, Ig-like domains, transmembrane domain, and ITIM motif are indicated by underscoring.

DETAILED DESCRIPTION OF THE INVENTION

Figure 3:
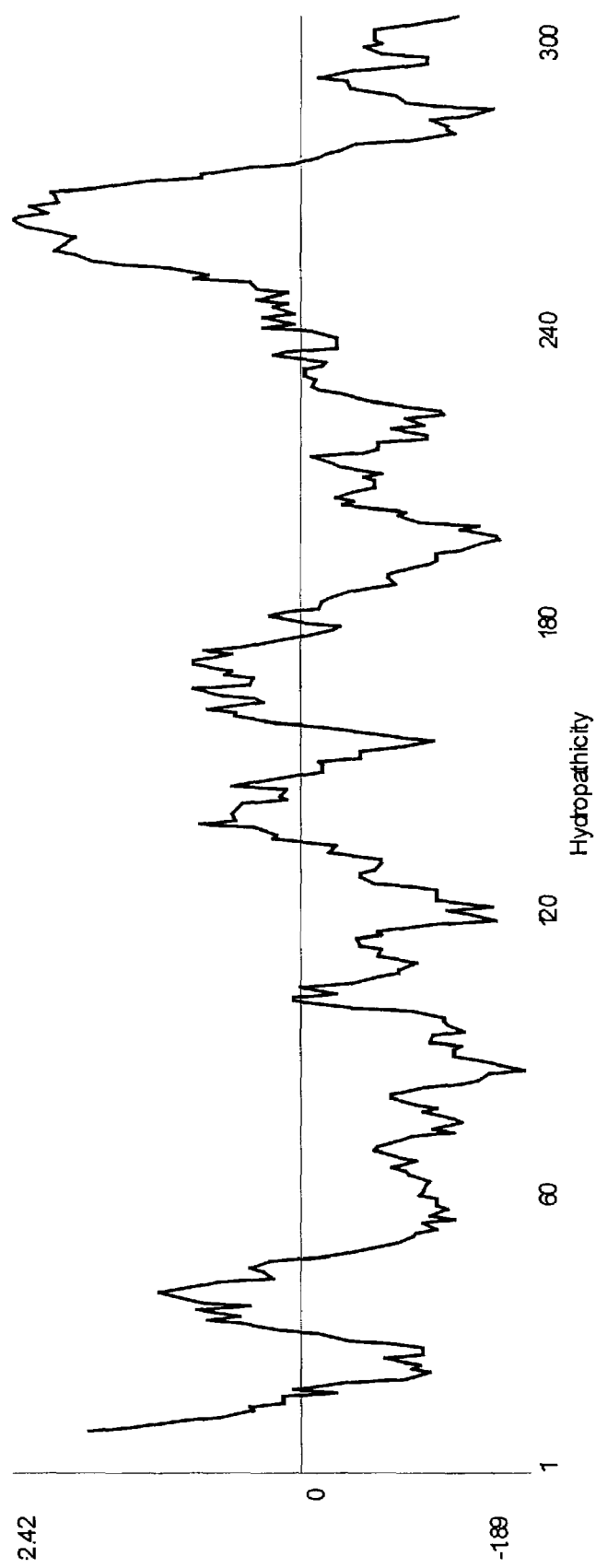
FIG. 3. Hydrophobicity plot of BGS-19 demonstrating a putative signal sequence at the amino terminus and a transmembrane domain (SEQ ID NO:8).
Figure 5:
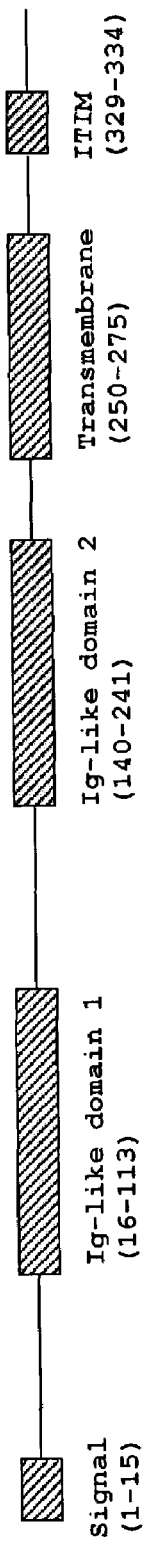
FIG. 5. Schematic drawing of the domain structure of BGS-19, indicating the amino acid boundaries of the signal peptide, Ig-like domain 1, Ig-like domain 2, transmembrane domain and ITIM motif.

The present invention is based, at least in part, on the discovery of a nucleic acid sequence encoding BGS-19, a novel human cell surface receptor of the immunoglobulin superfamily ("IgSF").

The present invention provides isolated nucleic acid molecules, that comprise, or alternatively consist of, a polynucleotide encoding the BGS-19 protein having the amino acid sequence shown in FIGS. 1A–C (SEQ ID NO:2) or the amino acid sequence encoded by the cDNA clone, BGS-19 deposited as ATCC Deposit Number PTA-3949 on Dec. 22, 2001. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 plasmid using the Not I and Sal I restriction sites.

Accordingly, the present invention relates to isolated BGS-19 polynucleotides derived from the BGS-19 polynucleotide and variants thereof. The invention also relates to polypeptides encoded by polynucleotides of the invention. The invention also relates to antibodies directed to polypeptides encoded by the polynucleotides of the invention. The invention also relates to agonists and antagonists of a BGS-19 polynucleotide, BGS-19 polypeptide or complexes comprising a BGS-19 polynucleotide or BGS-19 polypeptide.

The invention also relates to methods for detecting, identifying and characterizing agonists and antagonists of a BGS-19 polynucleotide or polypeptide, such as the nature and strength of binding to the BGS-19 polynucleotide or polypeptide.

The invention also relates to methods for synthesizing a BGS-19 polynucleotide, BGS-19 polypeptide, BGS-19 agonist, or BGS-19 antagonist, or variants thereof, including complexes among them or with other compounds.

The invention also relates to diagnosing a BGS-19-related disorder. The invention also relates to methods for monitoring the progression of a BGS-19-related disorder, and methods for assessing treatment efficacy.

The invention also relates to prevention or treatment of a BGS-19-related disorder comprising administering a BGS- 19 polynucleotide, BGS-19 polypeptide, BGS-19 agonist, and/or BGS-19 antagonist with or without additional therapeutic agents.

Isolated BGS-19 Polynucleotides

The present invention provides isolated polynucleotides encoding a BGS-19 polypeptide and variants thereof. Also encompassed by the present invention are specific portions of the BGS-19 polynucleotide and the polypeptide encoded by such portions. For example, individual subclones or subsequences used to assemble the full-length (or nearly full-length) BGS-19 cDNA or polynucleotide ("BGS-19 subsequences") are encompassed by the BGS-19 polynucleotides of the invention. Accordingly, any polypeptide encoded by such subclones or subsequences is encompassed by the BGS-19 polypeptides of the invention, which include, for example, the polynucleotides encoding the BGS-19 extracellular domain, BGS-19 intracellular domain, BGS-19 signal peptide, BGS-19 Ig-like domain 1 (SEQ ID NO:9), BGS-19 Ig-like domain 2 (SEQ ID NO:10), BGS-19 transmembrane domain, BGS-19 ITIM motif, and any subcellular localization signals.

Furthermore, partially assembled subsequences or hybrid molecules comprising BGS-19 subsequences or partially assembled subsequences are encompassed by the BGS-19 polynucleotides of the invention. Accordingly, any polypeptide encoded by such subclones or subsequences is encompassed by the BGS-19 polypeptides of the invention.

Similarly, the present invention encompasses specific portions of a BGS-19 polynucleotide or BGS-19 polypeptide that can be discerned as a domain or motif. Such domains and motifs include, but are not limited to, Ig domains, Ig-like domains, immunotyrosine-based inhibition motifs ("ITIMs"), signal sequences, transmembrane domains, phosphorylation sites, exons, introns, splice acceptor sites, splice donor sites, 5' and 3' regulatory regions of the mRNA, mRNA capping regions, promoter regions, transcriptional regulatory sites, enhancer sequences, extracellular ligand-binding sites, and derivatives thereof. In a specific embodiment, a BGS-19 polypeptide comprises an ITIM (Unkeless and Jin, 1997, "Inhibitory receptors, ITIM sequences and phosphatases", Curr Opin Immunol. 9:338–343).

Accordingly, a BGS-19 polynucleotide can comprise cDNA, genomic DNA, introns, exons, promoter regions, 5' and 3' regulatory regions of the polynucleotide, RNA, hnRNA, mRNA, regulatory regions within RNAs, and depolynucleotiderate variants thereof. Promoter sequences for BGS-19 can be determined by promoter-reporter polynucleotide assays and in vitro binding assays.

In preferred embodiments, the present invention encompasses a polynucleotide including the initiating start codon, in addition to, the resulting encoded polypeptide of BGS-19. Specifically, the present invention encompasses the polynucleotide corresponding to nucleotides 140 thru 1294 of SEQ ID NO:1, and the polypeptide corresponding to amino acids 1 thru 385 of SEQ ID NO:2. Also encompassed are recombinant vectors comprising said encoding sequence, and host cells comprising said vector.

In preferred embodiments, the present invention encompasses a polynucleotide lacking the initiating start codon, in addition to, the resulting encoded polypeptide of BGS-19. Specifically, the present invention encompasses the polynucleotide corresponding to nucleotides 143 thru 1294 of SEQ ID NO:1, and the polypeptide corresponding to amino acids 2 thru 385 of SEQ ID NO:2. Also encompassed are recombinant vectors comprising said encoding sequence, and host cells comprising said vector.

Using all, or a portion, of the polynucleotide sequence of BGS-19, as a hybridization probe, polynucleotides of the invention can be isolated using standard hybridization and cloning techniques (See, e.g., Sambrook et al., *Molecular Cloning: A Laboratory Manual*, 2nd ed., Cold Spring Harbor Laboratory, Cold Spring Harbor Laboratory Press, Cold Spring Harbor, N.Y., 1989).

An isolated polynucleotide that encodes a variant polypeptide can be created by introducing one or more nucleotide substitutions, additions or deletions into the nucleotide sequence of BGS-19. Such BGS-19 polynucleotide variants can result in one or more amino acid substitutions, additions or deletions in the encoded protein. Mutations can be introduced by standard techniques, such as site-directed mutapolynucleotidesis and PCR-mediated mutapolynucleotidesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid, asparagine, glutamine), uncharged polar side chains (e.g., glycine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutapolynucleotidesis, and the resultant mutants can be screened for biological activity to identify mutants that retain or antagonize activity. Following mutapolynucleotidesis, the encoded protein can be expressed recombinantly and the activity of the protein can be determined.

Nucleotide substitutions leading to amino acid substitutions at "non-essential" amino acid residues can also be introduced. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species can be non-essential for activity and thus would be likely targets for alteration. Such polypeptides would retain biological activity.

The present invention encompasses, in addition to the polynucleotides disclosed herein, 1) any polynucleotide that encodes a BGS-19 polypeptide of the invention; 2) any polynucleotide that hybridizes to the complement of the sequence depicted in FIGS. 2A–B or FIGS. 1A–C under highly stringent conditions, e.g., washing in 0.1×SSC/0.1% SDS at 68° C. (Ausubel et al., 1989, *Current Protocols in Molecular Biology*, Vol. I, Green Publishing Associates, Inc., and John Wiley & Sons, Inc., New York, at p. 2.10.3); and/or 3) any polynucleotide sequence that hybridizes to the complement of the sequence depicted in FIGS. 2A–B or FIGS. 1A–C under less stringent conditions, such as moderately stringent conditions, e.g., washing in 0.2×SSC/0.1% SDS at 45° C. (Ausubel et al., 1989, supra).

In one embodiment, a variant BGS-19 polynucleotide sequence hybridizes to a naturally-occurring BGS-19 polynucleotide under stringent conditions. In another embodiment, a variant BGS-19 polynucleotide sequence hybridizes to a naturally-occurring BGS-19 polynucleotide under moderately stringent conditions. In another embodiment, the BGS-19 polynucleotide hybridizes, under stringent or moderately stringent conditions, to a fragment of a naturally-occurring BGS-19 polynucleotide wherein the naturally-occurring BGS-19 polynucleotide is not a polynucleotide consisting of Genbank Accession Nos. gi|BI518708, gi|BF308356, gi|BF205116, gi|BF969219, gi|BG826221, and/or gi|AA341128.

The term "hybridizes under highly stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989) pp. 6.3.1–6.3.6. A preferred, non-limiting example of stringent hybridization conditions are hybridization in 6× sodium chloride/sodium citrate ("SSC") at about 45° C. followed by one or more washes in 0.2×SSC, 0.1% SDS at 50–65° C. Preferably, an isolated polynucleotide of the invention that hybridizes under stringent conditions to the sequence of SEQ ID NO: 1, 3 (or GenBank Accession No. AW225336), 5 (or GenBank Accession No. AW225339), 7, 9, 11, or 13, or a complement thereof, corresponds to a naturally-occurring polynucleotide.

Accordingly, the present invention contemplates polynucleotide variants that are revealed from inter-species comparisons of homologs of the BGS-19 polynucleotides. As such, homologs of a BGS-19 polynucleotide of the invention that are found in other species are encompassed by the present invention.

In addition to the polynucleotide sequence presented in FIGS. 1 and 3, it will be appreciated by those skilled in the art that DNA sequence polymorphisms that lead to changes in the amino acid sequence may exist within a population (e.g., the human population). Such polynucleotidetic polymorphisms may exist among individuals within a population due to natural allelic variation. An allele is one of a group of polynucleotides which occur alternatively at a given polynucleotidetic locus. As used herein, the phrase "allele" or "allelic variant" refers to a nucleotide sequence which occurs at a given chromosomal locus, to a polynucleotide molecule that encodes a polypeptide encoded by the nucleotide sequence which occurs at the given chromosomal locus (e.g., a cDNA molecule), or to a polypeptide encoded by the nucleotide sequence. Allelic variations can typically result in about 1–5% variance in the nucleotide sequence of a given polynucleotide. Alternative alleles can be identified by sequencing the polynucleotide of interest in a number of different individuals. This can be readily carried out by using hybridization probes to identify the same polynucleotidetic locus in a variety of individuals, and to characterize the polymorphisms present at the polynucleotidetic locus across the individuals. In one embodiment, polymorphisms that are associated with a particular disease and/or disorder are used as markers to diagnose said disease or disorder.

The present invention also encompasses complexes formed by a BGS-19 polynucleotide sequence and a binding partner and complexes formed by a BGS-19 polypeptide and a binding partner. A binder partner can be, but is not limited to, a polypeptide, carbohydrate or lipid. In a specific embodiment, the present invention encompasses the complex of BGS-19 and SH2 domain of phosphatases, such as SHP1 and SHP2. In other specific embodiments, the present invention encompasses the complexes of BGS-19 and polypeptides, and fragments thereof, encoded by the nucleic acid sequences depicted in FIGS. 1 and 3. The present invention also provides for methods of identifying and isolating such binding partners.

The present invention also encompasses mature forms of the polypeptide comprising, or alternatively consisting of, the polypeptide sequence of SEQ ID NO:2, the polypeptide encoded by the polynucleotide described as SEQ ID NO:1, and/or the polypeptide sequence encoded by a cDNA in the deposited clone. The present invention also encompasses polynucleotides encoding mature forms of the present invention, such as, for example the polynucleotide sequence of SEQ ID NO:1, and/or the polynucleotide sequence provided in a cDNA of the deposited clone. Specifically, the present invention encompasses the polynucleotide from about nucleotide position 185 to about nucleotide position 1294 of SEQ ID NO:1 (FIGS. 1A–C).

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10:1–6 (1997). The program relies upon the algorithm developed by von Heinje, though provides additional parameters to increase the prediction accuracy.

More recently, a hidden Markov model has been developed (H. Neilson, et al., Ismb 1998;6: 122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., + or −5 residues, or Preferably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:1 and/or the polynucleotide sequence contained in the cDNA of a deposited clone, in a mammalian cell (e.g., COS cells, as desribed below). These polypeptides, and the polynucleotides encoding such polypeptides, are contemplated by the present invention.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject, sequence which are not matched/aligned with the query sequence are manually corrected for. No other manual corrections are required for the purposes of the present invention.

BGS-19 Antisense Oligonucleotides

The present invention encompasses BGS-19 antisense polynucleotides, i.e., molecules which are complementary to a sense nucleic acid encoding a polypeptide of the invention, e.g., complementary to the coding strand of a double-stranded cDNA molecule or complementary to an mRNA sequence. The antisense polynucleotide can be complementary to an entire coding strand, or to only a portion thereof, e.g., all or part of the protein coding region (or open reading frame). An antisense polynucleotide can be antisense to all or part of a non-coding region of the coding strand of a nucleotide sequence encoding a polypeptide of the invention. The non-coding regions are the 5' and 3' sequences which flank the coding region and are not translated into amino acids.

The antisense oligonucleotides of the invention can be DNA or RNA or chimeric mixtures, derivatives, or variants thereof. The oligonucleotide can be modified at the base moiety, sugar moiety, or phosphate backbone, which can, for example, improve the oligonucleotide's pharmacokinetics and/or affect an oligonucleotide's hybridization to the target mRNA. The oligonucleotide can include other appended groups, such as for example, peptides (e.g., for targeting host cell receptors in vivo), agents facilitating transport across the cell membrane (See, e.g., Letsinger et al., 1989, "Cholesteryl-conjugated oligonucleotides: synthesis, properties, and activity as inhibitors of replication of human immunodeficiency virus in cell culture", Proc Natl Acad Sci. 86:6553–6556; Lemaitre et al., 1987, "Specific antiviral activity of a poly(L-lysine)-conjugated oligodeoxyribonucleotide sequence complementary to vesicular stomatitis virus N protein mRNA initiation site", Proc Natl Acad Sci. 84:648–652; PCT Publication No. WO 88/09810), hybridization-triggered cleavage agents (See, e.g., van der Krol, 1988, "Modulation of eukaryotic polynucleotide expression by complementary RNA or DNA sequences", Biotechniques 6:958–976), and intercalating agents (See, e.g., Zon, 1988, "Oligonucleotide analogues as potential chemotherapeutic agent", Pharm Res. 5:539–549). To this end, the oligonucleotide may be conjugated to another molecule, which includes, but is not limited to, a peptide, hybridization triggered cross-linking agent, transport agent, and hybridization-triggered cleavage agent.

An antisense oligonucleotide can be, for example, about 8, 10, 15, 20, 25, 30, 35, 40, 45 or 50 nucleotides or more in length. An antisense polynucleotide of the invention can be constructed using chemical synthesis and enzymatic ligation reactions using procedures known in the art.

Antisense oligonucleotides may be single or double stranded. Double stranded RNA's may be designed based upon the teachings of Paddison et al., Proc. Nat. Acad. Sci., 99:1443–1448 (2002); and International Publication Nos. WO 01/29058, and WO 99/32619; which are hereby incorporated herein by reference.

Various well-known modifications to the DNA molecules may be introduced as a means of increasing intracellular stability and half-life. For example, an antisense polynucleotide (e.g., an antisense oligonucleotide) can be chemically synthesized using naturally occurring nucleotides or variously modified nucleotides. Possible modifications include but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone. Examples of modified nucleotides which can be used to polynucleotiderate a BGS-19 antisense polynucleotide include, but are not limited to, 1-methylguanine, 1-methylinosine, 2,2-dimethylguanine, 2-methyladenine, 2-methylguanine, 2-methylthio-N6-isopentenyladenine, 2-thiocytosine, 2-thiouracil, 2,6-diaminopurine, 3-methylcytosine, 3-(3-amino-3-N-2-carboxypropyl) uracil, 4-acetylcytosine, 4-thiouracil, 5-fluorouracil, 5-bromouracil, 5-chlorouracil, 5-iodouracil, 5-(carboxyhydroxylmethyl) uracil, 5-carboxymethylaminomethyl-2-thiouridine, 5-carboxymethylaminomethyluracil, 5-methylcytosine, 5-methoxyaminomethyl-2-thiouracil, 5-methylaminomethyluracil, 5'-methoxycarboxymethyluracil, 5-methoxyuracil, 5-methyl-2-thiouracil, 5-methyl-2-thiouracil, 5-methyluracil, hypoxanthine, 7-methylguanine, beta-D-galactosylqueosine, beta-D-mannosylqueosine, dihydrouracil, inosine, N6-isopentenyladenine, N6-adenine, uracil-5-oxyacetic acid (v), pseudouracil, queosine, wybutoxosine, xanthine, uracil-5-oxyacetic acid methylester, (acp3)w and uracil-5-oxyacetic acid (v).

In another embodiment, the antisense oligonucleotide can also comprise, one or more modified sugar moieties, which includes, but is not limited to, 2-fluoroarabinose, arabinose, hexose, and xylulose.

In another embodiment, the antisense oligonucleotide comprises a modified phosphate backbone, which includes, but is not limited to, phosphorothioate, phosphorodithioate, phosphoramidothioate, phosphoramidate, phosphordiamidate, methylphosphonate, alkyl phosphotriester, formacetal, and analogs thereof.

In yet another embodiment, the antisense oligonucleotide is an α-anomeric oligonucleotide. An α-anomeric oligonucleotide can form double-stranded hybrids with complementary RNA, but in contrast to the usual β-oligonucleotides, the nucleotide strands run parallel to each other (Gautier et al., 1987, "Alpha-DNA. IV: Alpha-anomeric and beta-anomeric tetrathymidylates covalently linked to intercalating oxazolopyridocarbazole. Synthesis, physicochemical properties and poly (rA) binding", Nucl Acids Res. 15:6625–6641). The oligonucleotide can be a 2'-O-methylribonucleotide (Inoue et al., 1987, "Synthesis and hybridization studies on two complementary nona(2'-O-methyl) ribonucleotides", Nucl Acids Res. 15:6131–6148) or a chimeric RNA-DNA analogue (Inoue et al., 1987, "Sequence-dependent hydrolysis of RNA using modified oligonucleotide splints and RNase H", FEBS Lett. 215:327–330).

The antisense oligonucleotides may be RNA or DNA, or derivatives thereof. The particular form of antisense oligonucleotide may affect the oligonucleotide's pharmacokinetic parameters such as bioavailability, metabolism, and half-life. As such, where appropriate, the invention contemplates antisense oligonucleotide derivatives having properties that improve cellular uptake, enhance nuclease resistance, improve binding to the target sequence, or increase cleavage or degradation of the target sequence. The antisense oligonucleotides may comprise bases comprising, for example, phosphorothioates or methylphosphonates. The antisense oligonucleotides, instead, can be mixed oligonucleotides comprising combinations of phosphodiesters, phosphorothioate, and/or methylphosphonate nucleotides, among others. Such oligonucleotides may possess modifications which comprise, but are not limited to, 2-O'-alkyl or 2-O'-halo sugar modifications, backbone modifications (e.g., methylphosphonate, phosphorodithioate, phosphordithioate, formacetal, 3'-thioformacetal, sulfone, sulfamate, nitroxide backbone, morpholino derivatives and peptide nucleic acid ("PNA") derivatives), or derivatives wherein the base moieties have been modified. In another embodiment, antisense oligonucleotides comprise conjugates of the oligonucleotides and derivatives thereof (Goodchild, 1990, "Conjugates of oligonucleotides and modified oligonucleotides: a review of their synthesis and properties", Bioconjug Chem. 1:165–87).

In one embodiment, the deoxyribose phosphate backbone of a polynucleotide of the invention can be modified to incorporate peptide nucleic acids ("PNAs") (See, e.g., Hyrup and Nielsen, 1996, "Peptide nucleic acids (PNA): synthesis, properties and potential applications", Bioorg Med Chem. 4:5–23). As used herein, PNAs refer to nucleic acid mimics, in which the deoxyribose phosphate backbone is replaced by a pseudopeptide backbone. The neutral backbone of PNAs allows for specific hybridization to DNA and RNA under conditions of low ionic strength. The synthesis of PNA oligomers can be performed using any suitable peptide synthesis protocol known in the art (see, e.g., Hyrup and Nielsen, 1996 supra; Perry-O'Keefe et al., 1996, "Peptide nucleic acid pre-gel hybridization: an alternative to southern hybridization", Proc Natl Acad Sci. 93:14670–14675).

PNAs can be used in therapeutic and diagnostic applications. For example, PNAs can be used as antisense or antipolynucleotide agents for sequence-specific modulation of polynucleotide expression by, e.g., inducing transcription or translation arrest or inhibiting replication. PNAs can also be used for analyzing polynucleotide mutations by, for example, PNA-directed PCR clamping, or as artificial restriction enzymes when used in combination with other enzymes, such as for example, S1 nucleases (Hyrup and Nielsen, 1996 supra), or as probes or primers for DNA sequence and hybridization (Hyrup and Nielsen, 1996, supra; Perry-O'Keefe et al., 1996, supra).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be polynucleotiderated which may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen, 1996, supra).

The synthesis of PNA-DNA chimeras can be performed using various methods known in the art (see, e.g., Hyrup and Nielsen, 1996, supra, and Finn et al., 1996, "Synthesis and properties of DNA-PNA chimeric oligomers", Nucleic Acids Res. 24:3357–3363). For example, a DNA chain can be synthesized on a solid support using standard phosphoramidite coupling chemistry and modified nucleoside analogs. Compounds such as 5'-(4-methoxytrityl) amino-5'-deoxythymidine phosphoramidite can be used as a link between the PNA and the 5' end of DNA (Mag and Engels, 1989, "Synthesis and selective cleavage of oligodeoxyribonucleotides containing non-chiral internucleotide phosphoramidate linkages", Nucleic Acids Res. 17:5973–5988). PNA monomers are then coupled in a stepwise manner to produce a chimeric molecule with a 5' PNA segment and a 3' DNA segment (Finn et al., 1996, supra). Alternatively, chimeric molecules can be synthesized with a 5' DNA segment and a 3' PNA segment.

The target sequences may be RNA or DNA, and may be single-stranded or double-stranded. Target molecules include, but are not limited to, pre-mRNA, mRNA, and DNA. In a one embodiment, the target molecule is a BGS-19 mRNA. In a preferred embodiment, the target molecule is BGS-19 pre-mRNA or BGS-19 mRNA. In a specific embodiment, the antisense oligonucleotides hybridize to a portion anywhere along a BGS-19 pre-mRNA or mRNA. In another embodiment, a BGS-19 antisense oligonucleotides are selected from those oligonucleotides which hybridize to the translation initiation site, donor splicing site, acceptor splicing site, sites for transportation, or sites for degradation of a BGS-19 pre-mRNA or mRNA.

The antisense polynucleotides of the invention can be administered to a subject or polynucleotiderated in situ such that they hybridize with or bind to cellular mRNA and/or genomic DNA encoding a selected polypeptide of the invention to thereby inhibit expression, e.g., by inhibiting transcription and/or translation. An example of a route of administration of antisense polynucleotides of the invention includes direct injection at a tissue site. Alternatively, antisense polynucleotides can be modified to target selected cells and then administered systemically. For example, for systemic administration, antisense molecules can be modified such that they specifically bind to receptors or antigens expressed on a selected cell surface, e.g., by linking the antisense polynucleotides to peptides or antibodies which bind to cell surface receptors or antigens. The antisense polynucleotides can also be delivered to cells using the vectors described herein. To achieve sufficient intracellular concentrations of the antisense molecules, vector constructs in which the antisense polynucleotide is placed under the control of a strong pol II or pol III promoter are preferred.

For in vivo therapeutic use, a phosphorothioate derivative of a BGS-19 antisense oligonucleotide can be useful, at least partly because of greater resistance to degradation. In one embodiment, a BGS-19 antisense oligonucleotide is a hybrid oligonucleotide comprising phosphorothioate bases. In another embodiment, a BGS-19 antisense oligonucleotide comprises at least one phosphorothioate linkage. In yet another embodiment, a BGS-19 antisense oligonucleotide is comprised entirely of phosphorothioate linkages. Methods for preparing oligonucleotide derivatives are known in the art. See, e.g., Stein et al., 1988, "Physicochemical properties of phosphorothioate oligodeoxynucleotides", Nucl. Acids Res., 16:3209–3221; Blake et al., 1985, "Inhibition of rabbit globin mRNA translation by sequence-specific oligodeoxyribonucleotides", Biochemistry 24:6132–6138 (methylphosphonate); Morvan et al., 1986, "alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)]", Nucl Acids Res. 14:5019–5032 (alphadeoxynucleotides); Monia et al., 1993, "Evaluation of 2'-modified oligonucleotides containing 2' deoxy gaps as antisense inhibitors of polynucleotide expression", J. Biol. Chem. 268:14514–22 (2'-O-methyl-ribonucleosides); Asseline et al., 1984, "Nucleic acid-binding molecules with high affinity and base sequence specificity: intercalating agents covalently linked to oligodeoxynucleotides", Proc Natl Acad Sci. 81:3297–3301 (acridine); Knorre et al., 1985, "Reactive oligonucleotide derivatives and sequence-specific modification of nucleic acids", Biochimie 67:785–789; Vlassov et al., 1986, "Complementary addressed modification and cleavage of a single stranded DNA fragment with alkylating oligonucleotide derivatives", Nucl Acids Res. 14:4065–4076 (N-2-chlorocethylamine and phenazine); Webb and Matteucci , 1986, "Hybridization triggered cross-linking of deoxyoligonucleotides", Nucl Acids Res. 14:7661–7674 (5-methyl-$N^4$-$N^4$-ethanocytosine);, Boutorin et al. 1984, FEBS Letters 172:43–46 (Fe-ethylenediamine tetraacetic acid ("EDTA") and analogues); Boutorin et al., 1989, "Synthesis of alkylating oligonucleotide derivatives containing cholesterol or phenazinium residues at their 3'-terminus and their interaction with DNA within mammalian cells", FEBS Lett. 254:129–132; Chen and Sigman, 1986, "Nuclease activity of 1,10-phenanthroline-copper: sequence-specific targeting", Proc Natl Acad Sci. 83:7147–7151 (5-glycylamido-1,10-o-phenanthroline); and Chu and Orgel, 1985, "Nonenzymatic sequence-specific cleavage of single-stranded DNA", Proc Natl Acad Sci. 82:963–967 (diethylenetriaamine-pentaacetic acid derivatives).

Isolated BGS-19 Polypeptides

One aspect of the invention pertains to an isolated BGS-19 protein, and biologically active portions thereof (e.g., ITIM motifs, extracellular ligand binding domains), as well as polypeptide fragments suitable for use as immunogens to raise antibodies directed against a BGS-19 polypeptide of the invention. In one embodiment, the native polypeptide can be isolated from cells or tissues expressing a BGS-19 polypeptide using standard protein purification techniques. In another embodiment, polypeptides of the invention are produced from expression vectors by recombinant DNA techniques. In yet another embodiment, a polypeptide of the invention can be synthesized chemically using standard peptide synthesis techniques.

An isolated or purified protein or biologically active portion thereof is substantially free of cellular material or other contaminating proteins from the cell or tissue source from which the protein is derived, or substantially free of chemical precursors or other chemicals when chemically synthesized. The language "substantially free" indicates protein preparations in which the protein is separated from cellular components of the cells from which it is isolated or recombinantly produced. Thus, protein that is substantially free of cellular material includes protein preparations having less than 20%, 10%, or 5% (by dry weight) of a contaminating protein. Similarly, when an isolated BGS-19 polypeptide of the invention is recombinantly produced, it is substantially free of culture medium. When the BGS-19 protein is produced by chemical synthesis, it is preferably substantially free of chemical precursors or other chemicals.

Biologically active portions of a polypeptide of the invention include polypeptides comprising amino acid sequences identical to or derived from the amino acid sequence of the protein, such that the variants sequences comprise conservative substitutions or truncations. Typically, biologically active portions comprise a domain or motif with at least one activity of the corresponding protein. Domains or motifs include, but are not limited to, a biologically active portion of a protein of the invention. Polypeptides of the invention can comprise, for example, a BGS-19 extracellular domain, BGS-19 intracellular domain, BGS-19 signal peptide, BGS-19 Ig-like domain 1 (SEQ ID NO:9), BGS-19 Ig-like domain 2 (SEQ ID NO:10), BGS-19 transmembrane domain, BGS-19 ITIM motif, subcellular localization signals. In a specific embodiment, a BGS-19 polypeptide comprises the signal domain at amino acid residues 1–15, the Ig-like domain 1 at about amino acid residues 16–113 (SEQ ID NO:9), the Ig-like domain 2 at about amino acid residues 140–241 (SEQ ID NO:10), the transmembrane domain at about amino acid residues 250–275 (SEQ ID NO:8), and the ITIM motif at about amino acid residues 329–334. The BGS-19 polypeptide (SEQ ID NO:2) has a predicted molecular weight of 42 kD.

In preferred embodiments, the following BGS-19 transmembrane domain polypeptide is encompassed by the present invention: AALGAGVAALLAFCSCL VVFRVKICR (SEQ ID NO:8). Polynucleotides encoding this polypeptide are also provided. The present invention also encompasses the use of this BGS-19 transmembrane domain polypeptide as an immunogenic and/or antigenic epitope as described elsewhere herein.

In preferred embodiments, the following BGS-19 Ig-like domain polypeptides are encompassed by the present invention:

```
GSLNKDPSYSLQVQRQVPVPEGLC                               (SEQ ID NO:9)

VIVSCNLSYPRDGWDESTAAYGYWFKGRTSPKTGAPVATNNQSREVEMSTRD

RFQLTGDPGKGSCSLVIRDAQRED,

VTALTKKPDVYIP                                          (SEQ ID NO:10)

ETLEPGQPVTVICVFNWAFKKCPAPSFSWTGAALSPRRTRPSTSQPSDPGVLELP

PIQMEHEGEFTCHAQHPLGSQHVSLSLSVIIWKLE and/or QTVHFTVREAPQI.
```

Polynucleotides encoding these polypeptides are also provided. The present invention also encompasses the use of these BGS-19 Ig-like domain polypeptides as immunogenic and/or antigenic epitopes as described elsewhere herein.

In one embodiment, a BGS-19 polypeptide has a transmembrane domain, which is an amino acid sequence comprising at least about 20 to 40 amino acid residues in length and features hydrophobic amino acid residues, such as alanine, leucine, isoleucine, phenylalanine, proline, tyrosine, tryptophan, or valine. In a preferred embodiment, a transmembrane domain comprises at least about 20 to 40 amino acid residues, preferably 25–30 amino acid residues, and has at least about 60% to 80% hydrophobic residues.

In one embodiment, a BGS-19 polypeptide comprises a portion of the amino sequence depicted in FIGS. 2A–B or FIGS. 1A–C. In one embodiment, a BGS-19 polypeptide comprises at least 4, 5, 6, 7, 8, 9, 10, 11, 12, 13, 14, 15, 16, 17, 18, 19 or 20 amino acids of the amino sequence depicted in FIGS. 2A–B or FIGS. 1A–C. In further embodiments, the BGS-19 polypeptide does not consist of the sequence

```
MLLLPLLLPVLGAGSLNKDPSYSLQVQRQVPVPEGLCVIVSCNLSYPRDGWDES  (SEQ ID NO:11)

TAAYGYWFKG;

TSPKTGAPVATNNQSREVEMSTR                                 (SEQ ID NO:12)

DRFQLTGDPGKGSCSLVIRDAQREDEAWYFFRVERGSRVRHSF;

LKVTALT;                                                (SEQ ID NO:13)

KPDVYLPETLEPG;                                          (SEQ ID NO:14)

RVKICRKEARKRAAAEQDVPSTLGPISQGHQHECSAGSSQDHPPPGAATYTPGK  (SEQ ID NO:15)
```

```
GEEQELHYASLSFQ;

GLRLWEPADQEAPSTTEYSEIKIHT                              (SEQ ID NO:16)

GQPLRGPGFGLQLEREMSGMVP;

RVKICRKEARKRAAAEQD                                     (SEQ ID NO:17)

VPSTLGPISQGHQHECSAGSSQDHPPPGAATYTPGKGEEQ;

GPGFGLQLEREMSG;                                        (SEQ ID NO:18)

LHYASLSFQGLRLW;                                        (SEQ ID NO:19)

RVKICRKEARKRAAAEQDVPSTLGPISQGHQHECSAGSSQDHP;           (SEQ ID NO:20)

PGAATYT; or                                            (SEQ ID NO:21)

GKGEEQELHYA.                                           (SEQ ID NO:22)
```

In a specific embodiment, a BGS-19 polypeptide comprises the amino acid sequence LLLPLLLPVL (SEQ ID NO:23). In another specific embodiment, a BGS-19 polypeptide comprises the amino acid sequence MLLLPLLLPVLG (SEQ ID NO:24). In another specific embodiment, a BGS-19 polypeptide comprises the amino acid sequence VPEGLC (SEQ ID NO:25). In another specific embodiment, a BGS-19 polypeptide comprises the amino acid sequence PVPEGLCV (SEQ ID NO:26). In another specific embodiment, a BGS-19 polypeptide comprises the amino acid sequence AYGYWFK (SEQ ID NO:27). In another specific embodiment, a BGS-19 polypeptide comprises the amino acid sequence AAYGYWFKG (SEQ ID NO:28). In another specific embodiment, a BGS-19 polypeptide comprises the amino acid sequence GAPVATN (SEQ ID NO:29). In another specific embodiment, a BGS-19 polypeptide comprises the amino acid sequence TGAPVATNN (SEQ ID NO:30). In another specific embodiment, a BGS-19 polypeptide comprises the amino acid sequence GAPVATNNNQSREVEMSTR (SEQ ID NO:31). In another specific embodiment, a BGS-19 polypeptide comprises the amino acid sequence GAPVATNNNQSREVEMSTRDRFQLTGDP (SEQ ID NO:32). In another specific embodiment, a BGS-19 polypeptide comprises the amino acid sequence QSREVEMSTR (SEQ ID NO:33). In another specific embodiment, a BGS-19 polypeptide comprises the amino acid sequence NQSREVEMSTRD (SEQ ID NO:34). In another specific embodiment, a BGS-19 polypeptide comprises the amino acid sequence RFQLTGDP (SEQ ID NO:35). In another specific embodiment, a BGS-19 polypeptide comprises the amino acid sequence DRFQLTGDPG (SEQ ID NO:36). In another specific embodiment, a BGS-19 polypeptide comprises the amino acid sequence KGSCSLVIRDAQ (SEQ ID NO:37). In another specific embodiment, a BGS-19 polypeptide comprises the amino acid sequence GKGSCSLVIRDAQR (SEQ ID NO:38). In another specific embodiment, a BGS-19 polypeptide comprises the amino acid sequence YFFRVERGS (SEQ ID NO:39). In another specific embodiment, a BGS-19 polypeptide comprises the amino acid sequence WYFFRVERGSR (SEQ ID NO:40). In another specific embodiment, a BGS-19 polypeptide comprises the amino acid sequence FFLKVTALT (SEQ ID NO:41). In another specific embodiment, a BGS-19 polypeptide comprises the amino acid sequence AFFLKVTALTK (SEQ ID NO:42). In another specific embodiment, a BGS-19 polypeptide comprises the amino acid sequence KPDVYIPETLEPGQPVTVICVFNWAF (SEQ ID NO:43). In another specific embodiment, a BGS-19 polypeptide comprises the amino acid sequence KKPDVYIPETLEPGQPVTVICVFNWAFK (SEQ ID NO:44). In another specific embodiment, a BGS-19 polypeptide comprises the amino acid sequence CPAPSFSWTGAALS (SEQ ID NO:45). In another specific embodiment, a BGS-19 polypeptide comprises the amino acid sequence KCPAPSFSWTGAALSP (SEQ ID NO:46). In another specific embodiment, a BGS-19 polypeptide comprises the amino acid sequence PSFSWTGAALS (SEQ ID NO:47). In another specific embodiment, a BGS-19 polypeptide comprises the amino acid sequence APSFSWTGAALSP (SEQ ID NO:48). In another specific embodiment, a BGS-19 polypeptide comprises the amino acid sequence PPIQMEH (SEQ ID NO:49). In another specific embodiment, a BGS-19 polypeptide comprises the amino acid sequence PPIQMEHE (SEQ ID NO:50). In another specific embodiment, a BGS-19 polypeptide comprises the amino acid sequence LPPIQMEHE (SEQ ID NO:51). In another specific embodiment, a BGS-19 polypeptide comprises the amino acid sequence GAALGAGVAALL (SEQ ID NO:52). In another specific embodiment, a BGS-19 polypeptide comprises the amino acid sequence LGAALGAGVAALL (SEQ ID NO:53). In another specific embodiment, a BGS-19 polypeptide comprises the amino acid sequence LGAALGAGVAALLA (SEQ ID NO:54). In another specific embodiment, a BGS-19 polypeptide comprises the amino acid sequence ELHYASLSF (SEQ ID NO:55). In another specific embodiment, a BGS-19 polypeptide comprises the amino acid sequence QELHYASLSFQ (SEQ ID NO:56).

In a particular embodiment, a BGS-19 polypeptide consists of an amino acid sequence recited above. In another particular embodiment, a BGS-19 polypeptide consists of an amino acid sequence recited above with 1, 2, 3, 4, 5, 6, 7, 8, 9 or 10 consecutive amino acids of the native BGS-19 polypeptide flanking the recited amino acid sequence. In a further embodiment, the 1, 2, 3, 4, 5, 6, 7, 8, 9 or 10 consecutive amino acids of the native BGS-19 polypeptide are the amino acids normally flanking the recited amino acid sequence.

In another particular embodiment, a BGS-19 polypeptide consists of an amino acid sequence recited above with 10, 20, 30, 40, 50, 60, 70, 80, 90 or 100 consecutive amino acids of the native BGS-19 polypeptide flanking the recited amino acid sequence. In a further embodiment, the 10, 20, 30, 40, 50, 60, 70, 80, 90 or 100 consecutive amino acids of the native BGS-19 polypeptide are the amino acids normally flanking the recited amino acid sequence.

The BGS-19 polypeptide has been shown to comprise two glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptides are encompassed by the present invention: VIVSCNLSYPRDGW (SEQ ID NO:62), and/or PVATNNQSREVEMS (SEQ ID NO:63). Polynucleotides encoding these polypeptides are also provided. The present invention also encompasses the use of these BGS-19 asparagine glycosylation site polypeptides as immunogenic and/or antigenic epitopes as described elsewhere herein.

The BGS-19 polypeptides of the present invention were determined to comprise several phosphorylation sites based upon the Motif algorithm (Genetics Computer Group, Inc.). The phosphorylation of such sites may regulate some biological activity of the BGS-19 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the BGS-19 polypeptide to associate with other immunoglobulin proteins, the ability of BGS-19 to serve as an antigen receptors, cytokine receptors, as a receptor for cell-surface molecules (e.g., other IgSF proteins, adhesion molecules), and as a counter-receptor.

Specifically, the BGS-19 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973–977 (1982); Hunter T., J. Biol. Chem. 257:4843–4848(1982), and Cooper J. A., Esch F. S., Taylor S. S., Hunter T., J. Biol. Chem. 259:7835–7841(1984), which are hereby incorporated herein by reference.

In preferred embodiments, the following tyrosine phosphorylation site polypeptides are encompassed by the present invention: IRDAQREDEAWYFFRVE (SEQ ID NO:68). Polynucleotides encoding these polypeptides are also provided. The present invention also encompasses the use of these BGS-19 tyrosine phosphorylation site polypeptides as immunogenic and/or antigenic epitopes as described elsewhere herein.

The BGS-19 polypeptide was predicted to comprise four PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: FKGRTSPKTGAPV (SEQ ID NO:64), REVEMSTRDRFQL (SEQ ID NO:65), KVTALTKKPDVYI (SEQ ID NO:66), and/or TGAALSPRRTRPS (SEQ ID NO:67). Polynucleotides encoding these polypeptides are also provided. The present invention also encompasses the use of these BGS-19 PKC phosphorylation site polypeptides as immunogenic and/or antigenic epitopes as described elsewhere herein.

The BGS-19 polypeptide was predicted to comprise three casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation sites may be found in reference to the following publication: Pinna L. A., Biochim. Biophys. Acta 1054: 267–284(1990); which is hereby incorporated herein in its entirety.

In preferred embodiments, the following casein kinase II phosphorylation site polypeptide is encompassed by the present invention: REVEMSTRDRFQLT (SEQ ID NO:69), ECSAGSSQDHPPPG (SEQ ID NO:70), and/or DQEAPSTTEYSEIK (SEQ ID NO:71). Polynucleotides encoding these polypeptides are also provided. The present invention also encompasses the use of this casein kinase II phosphorylation site polypeptide as an immunogenic and/or antigenic epitope as described elsewhere herein.

The BGS-19 polypeptide was predicted to comprise seven N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.). In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69–99(1988); and Grand R. J. A., Biochem. J. 258:625–638(1989); which is hereby incorporated herein in its entirety.

In preferred embodiments, the following N-myristoylation site polypeptides are encompassed by the present invention:

| | |
|---|---|
| TSPKTGAPVATNNQSR, | (SEQ ID NO:72) |
| ETLEPGQPVTVICVFN, | (SEQ ID NO:73) |
| WKLEHGGGLGLGAALG, | (SEQ ID NO:74) |
| LEHGGGLGLGAALGAG, | (SEQ ID NO:75) |
| HGGGLGLGAALGAGVA, | (SEQ ID NO:76) |
| GGLGLGAALGAGVAAL, and/or | (SEQ ID NO:77) |
| LGAALGAGVAALLAFC. | (SEQ ID NO:78) |

Polynucleotides encoding these polypeptides are also provided. The present invention also encompasses the use of these N-myristoylation site polypeptides as immunogenic and/or antigenic epitopes as described elsewhere herein.

Moreover, in confirmation of the BGS-19 polypeptide representing an immunoglobulin-like domain containing protein, it has been shown to comprise one Ig_MHC site according to the Motif algorithm (Genetics Computer Group, Inc.). The identification of the BGS-19 polypeptide as containing an Ig_MHC site is consistent with its potential involvement in immune and/or hematopoietic modulation.

The basic structure of immunoglobulin (Ig) molecules is a tetramer of two light chains and two heavy chains linked by disulfide bonds. There are two types of light chains: kappa and lambda, each composed of a constant domain (CL) and a variable domain (VL). There are five types of heavy chains: alpha, delta, epsilon, gamma and mu, all consisting of a variable domain (VH) and three (in alpha, delta and gamma) or four (in epsilon and mu) constant domains (CH1 to CH4).

The major histocompatibility complex (MHC) molecules are made of two chains. In class I the alpha chain is composed of three extracellular domains, a transmembrane region and a cytoplasmic tail. The beta chain (beta-2-microglobulin) is composed of a single extracellular domain. In class II, both the alpha and the beta chains are composed of two extracellular domains, a transmembrane region and a cytoplasmic tail.

It is known that the Ig constant chain domains and a single extracellular domain in each type of MHC chains are related. These homologous domains are approximately one hundred amino acids long and include a conserved intradomain disulfide bond.

The consensus pattern for Ig_MHC domain signatures is the following: [FY]-x-C-x-[VA]-x-H, wherein "x" represents any amino acid.

Sequences known to belong to this class are the following: Ig heavy chains type Alpha C region—All, in CH2 and CH3; Ig heavy chains type Delta C region—All, in CH3; Ig heavy chains type Epsilon C region—All, in CH1, CH3 and CH4; Ig heavy chains type Gamma C region—All, in CH3 and also CH1 in some cases; Ig heavy chains type Mu C region—All, in CH2, CH3 and CH4; Ig light chains type Kappa C region—In all CL except rabbit and Xenopus; Ig light chains type Lambda C region—In all CL except rabbit; MHC class I alpha chains—All, in alpha-3 domains; the cytomegalovirus MHC-1 homologous protein [6]; Beta-2-microglobulin—All; MHC class II alpha chains—All, in alpha-2 domains; and MHC class II beta chains—All, in beta-2 domains.

Additional information related to immunoglobulin domains and MGC domains may be obtained through reference to the following publications: Gough N., Trends Biochem. Sci. 6:203–205(1981); Klein J., Figueroa F., Immunol. Today 7:41–44(1986); Figueroa F., Klein J., Immunol. Today 7:78–81(1986); Orr H. T., Lancet D., Robb R. J., Lopez de Castro J. A., Strominger J. L., Nature 282:266–270(1979); Cushley W., Owen M. J., Immunol. Today 4:88–92(1983); and Beck S., Barrel B. G., Nature 331:269–272(1988); which are hereby incorporated by reference herein.

In preferred embodiments, the following Ig_MHC signature domain polypeptide is encompassed by the present invention: EHEGEFTCHAQHPLGSQ (SEQ ID NO:79). Polynucleotides encoding this polypeptide is also provided. The present invention also encompasses the use of the BGS-19 Ig_MHC signature domain polypeptide as immunogenic and/or antigenic epitopes as described elsewhere herein.

In preferred embodiments, the following N-terminal BGS-19 deletion polypeptides are encompassed by the present invention: M1-K385, L2-K385, L3-K385, L4-K385, P5-K385, L6-K385, L7-K385, L8-K385, P9-K385, V10-K385, L 11-K385, G12-K385, A13-K385, G14-K385, S15-K385, L16-K385, N17-K385, K18-K385, D19-K385, P20-K385, S21-K385, Y22-K385, S23-K385, L24-K385, Q25-K385, V26-K385, Q27-K385, R28-K385, Q29-K385, V30-K385, P31-K385, V32-K385, P33-K385, E34-K385, G35-K385, L36-K385, C37-K385, V38-K385, I39-K385, V40-K385, S41-K385, C42-K385, N43-K385, L44-K385, S45-K385, Y46-K385, P47-K385, R48-K385, D49-K385, G50-K385, W51-K385, D52-K385, E53-K385, S54-K385, T55-K385, A56-K385, A57-K385, Y58-K385, G59-K385, Y60-K385, W61-K385, F62-K385, K63-K385, G64-K385, R65-K385, T66-K385, S67-K385, P68-K385, K69-K385, T70-K385, G71-K385, A72-K385, P73-K385, V74-K385, A75-K385, T76-K385, N77-K385, N78-K385, Q79-K385, S80-

K385, R81-K385, E82-K385, V83-K385, E84-K385, M85-K385, S86-K385, T87-K385, R88-K385, D89-K385, R90-K385, F91-K385, Q92-K385, L93-K385, T94-K385, G95-K385, D96-K385, P97-K385, G98-K385, K99-K385, G100-K385, S101-K385, C102-K385, S103-K385, L104-K385, V105-K385, I106-K385, R107-K385, D108-K385, A109-K385, Q110-K385, R111-K385, E112-K385, D113-K385, E114-K385, A115-K385, W116-K385, Y117-K385, F118-K385, F119-K385, R120-K385, V121-K385, E122-K385, R123-K385, G124-K385, S125-K385, R126-K385, V127-K385, R128-K385, H129-K385, S130-K385, F131-K385, L132-K385, S133-K385, N134-K385, A135-K385, F136-K385, F137-K385, L138-K385, K139-K385, V140-K385, T141-K385, A142-K385, L143-K385, T144-K385, K145-K385, K146-K385, P147-K385, D148-K385, V149-K385, Y150-K385, I151-K385, P152-K385, E153-K385, T154-K385, L155-K385, E156-K385, P157-K385, G158-K385, Q159-K385, P160-K385, V161-K385, T162-K385, V163-K385, I164-K385, C165-K385, V166-K385, F167-K385, N168-K385, W169-K385, A170-K385, F171-K385, K172-K385, K173-K385, C174-K385, P175-K385, A176-K385, P177-K385, S178-K385, F179-K385, S180-K385, W181-K385, T182-K385, G183-K385, A184-K385, A185-K385, L186-K385, S187-K385, P188-K385, R189-K385, R190-K385, T191-K385, R192-K385, P193-K385, S194-K385, T195-K385, S196-K385, Q197-K385, P198-K385, S199-K385, D200-K385, P201-K385, G202-K385, V203-K385, L204-K385, E205-K385, L206-K385, P207-K385, P208-K385, I209-K385, Q210-K385, M211-K385, E212-K385, H213-K385, E214-K385, G215-K385, E216-K385, F217-K385, T218-K385, C219-K385, H220-K385, A221-K385, Q222-K385, H223-K385, P224-K385, L225-K385, G226-K385, S227-K385, Q228-K385, H229-K385, V230-K385, S231-K385, L232-K385, S233-K385, L234-K385, S235-K385, V236-K385, H237-K385,, W238-K385, K239-K385, L240-K385, E241-K385, H242-K385, G243-K385, G244-K385, G245-K385, L246-K385, G247-K385, L248-K385, G249-K385, A250-K385, A251-K385, L252-K385, G253-K385, A254-K385, G255-K385, V256-K385, A257-K385, A258-K385, L259-K385, L260-K385, A261-K385, F262-K385, C263-K385, S264-K385, C265-K385, L266-K385, V267-K385, V268-K385, F269-K385, R270-K385, V271-K385, K272-K385, I273-K385, C274-K385, R275-K385, K276-K385, E277-K385, A278-K385, R279-K385, K280-K385, R281-K385, A282-K385, A283-K385, A284-K385, E285-K385, Q286-K385, D287-K385, V288-K385, P289-K385, S290-K385, T291-K385, L292-K385, G293-K385, P294-K385, I295-K385, S296-K385, Q297-K385, G298-K385, H299-K385, Q300-K385, H301-K385, E302-K385, C303-K385, S304-K385, A305-K385, G306-K385, S307-K385, S308-K385, Q309-K385, D310-K385, H311-K385, P312-K385, P313-K385, P314-K385, G315-K385, A316-K385, A317-K385, T318-K385, Y319-K385, T320-K385, P321-K385, G322-K385, K323-K385, G324-K385, E325-K385, E326-K385, Q327-K385, E328-K385, L329-K385, H330-K385, Y331-K385, A332-K385, S333-K385, L334-K385, S335-K385, F336-K385, Q337-K385, G338-K385, L339-K385, R340-K385, L341-K385, W342-K385, E343-K385, P344-K385, A345-K385, D346-K385, Q347-K385, E348-K385, A349-K385, P350-K385, S351-K385, T352-K385, T353-K385, E354-K385, Y355-K385, S356-K385, E357-K385, I358-K385, K359-K385, I360-K385, H361-K385, T362-K385, G363-K385, Q364-K385, P365-K385, G370-K385, L366-K385, R367-K385, G368-K385, P369-K385, G370-K385, F371-K385, G372-K385, L373-K385, Q374-K385, L375-K385, E376-K385, R377-K385, E378-K385, and/or M379-K385 of SEQ ID NO:2. Polynucleotide sequences encoding these polypeptides are also provided. The present invention also encompasses the use of these N-terminal BGS-19 deletion polypeptides as immunogenic and/or antigenic epitopes as described elsewhere herein.

In preferred embodiments, the following C-terminal BGS-19 deletion polypeptides are encompassed by the present invention: M1-K385, M1-P384, M1-V383, M1-M382, M1-G381, M1-S380, M1-M379, M1-E378, M1-R377, M1-E376, M1-L375, M1-Q374, M1-L373, M1-G372, M1-F371, M1-G370, M1-P369, M1-G368, M1-R367, M1-L366, M1-P365, M1-Q364, M1-G363, M1-T362, M1-H361, M1-I360, M1-K359, M1-I358, M1-E357, M1-S356, M1-Y355, M1-E354, M1-T353, M1-T352, M1-S351, M1-P350, M1-A349, M1-E348, M1-Q347, M1-D346, M1-A345, M1-P344, M1-E343, M1-W342, M1-L341, M1-R340, M1-L339, M1-G338, M1-Q337, M1-F336, M1-S335, M1-L334, M1-S333, M1-A332, M1-Y331, M1-H330, M1-L329, M1-E328, M1-Q327, M1-E326, M1-E325, M1-G324, M1-K323, M1-G322, M1-P321, M1-T320, M1-Y319, M1-T318, M1-A317, M1-A316, M1-G315, M1-P314, M1-P313, M1-P312, M1-H311, M1-D310, M1-Q309, M1-S308, M1-S307, M1-G306, M1-A305, M1-S304, M1-C303, M1-E302, M1-H301, M1-Q300, M1-H299, M1-G298, M1-Q297, M1-S296, M1-I295, M1-P294, M1-G293, M1-L292, M1-T291, M1-S290, M1-P289, M1-V288, M1-D287, M1-Q286, M1-E285, M1-A284, M1-A283, M1-A282, M1-R281, M1-K280, M1-R279, M1-A278, M1-E277, M1-K276, M1-R275, M1-C274, M1-I273, M1-K272, M1-V271, M1-R270, M1-F269, M1-V268, M1-V267, M1-L266, M1-C265, M1-S264, M1-C263, M1-F262, M1-A261, M1-L260, M1-L259, M1-A258, M1-A257, M1-V256, M1-G255, M1-A254, M1-G253, M1-L252, M1-A251, M1-A250, M1-G249, M1-L248, M1-G247, M1-L246, M1-G245, M1-G244, M1-G243, M1-H242, M1-E241, M1-L240, M1-K239, M1-W238, M1-H237, M1-V236, M1-S235, M1-L234, M1-S233, M1-L232, M1-S231, M1-V230, M1-H229, M1-Q228, M1-S227, M1-G226, M1-L225, M1-P224, M1-H223, M1-Q222, M1-A221, M1-H220, M1-C219, M1-T218, M1-F217, M1-E216, M1-G215, M1-E214, M1-H213, M1-E212, M1-M211, M1-Q210, M1-I209, M1-P208, M1-P207, M1-L206, M1-E205, M1-L204, M1-V203, M1-G202, M1-P201, M1-D200, M1-S 199, M1-P198, M1-Q197, M1-S196, M1-T195, M1-S194, M1-P193, M1-R192, M1-T191, M1-R190, M1-R189, M1-P188, M1-S187, M1-L186, M1-A185, M1-A184, M1-G183, M1-T182, M1-W181, M1-S180, M1-F179, M1-S178, M1-P177, M1-A176, M1-P175, M1-C174, M1-K173, M1-K172, M1-F171, M1-A170, M1-W169, M1-N168, M1-F167, M1-V166, M1-C165, M1-I164, M1-V163, M1-T162, M1-V161, M1-P160, M1-Q159, M1-G158, M1-P157, M1-E156, M1-L155, M1-T154, M1-E153, M1-P152, M1-I151, M1-Y150, M1-V149, M1-D148, M1-P147, M1-K146, M1-K145, M1-T144, M1-L143, M1-A142, M1-T141, M1-V140, M1-K139, M1-L138, M1-F137, M1-F136, M1-A135, M1-N134, M1-S133, M1-L132, M1-F131, M1-S130, M1-H129, M1-R128, M1-V127, M1-R126, M1-S125, M1-G124, M1-R123, M1-E122, M1-V121, M1-R120, M1-F119, M1-F118, M1-Y117, M1-W116, M1-A115, M1-E114, M1-D113, M1-E112, M1-R111, M1-Q110, M1-A109, M1-D108, M1-R107, M1-I106, M1-V105, M1-L104, M1-S103, M1-C102, M1-S101, M1-G100, M1-K99, M1-G98, M1-P97, M1-D96, M1-G95, M1-T94, M1-L93, M1-Q92, M1-F91, M1-R90, M1-D89, M1-R88, M1-T87, M1-S86, M1-M85, M1-E84, M1-V83, M1-E82, M1-R81, M1-S80, M1-Q79, M1-N78, M1-N77, M1-T76, M1-A75, M1-V74, M1-P73, M1-A72, M1-G71, M1-T70, M1-K69, M1-P68, M1-S67, M1-T66, M1-R65, M1-G64, M1-K63, M1-F62, M1-W61, M1-Y60, M1-G59, M1-Y58, M1-A57, M1-A56, M1-T55, M1-S54, M1-E53, M1-D52, M1-W51, M1-G50, M1-D49, M1-R48, M1-P47, M1-Y46, M1-S45, M1-L44, M1-N43, M1-C42, M1-S41, M1-V40, M1-I39, M1-V38, M1-C37, M1-L36, M1-G35, M1-E34, M1-P33, M1-V32, M1-P31, M1-V30, M1-Q29, M1-R28, M1-Q27, M1-V26, M1-Q25, M1-L24, M1-S23, M1-Y22, M1-S21, M1-P20, M1-D19, M1-K18, M1-N17, M1-L16, M1-S15, M1-G14, M1-A13, M1-G12, M1-L11, M1-V10, M1-P9, M1-L8, and/ or M1-L7 of SEQ ID NO:2. Polynucleotide sequences encoding these polypeptides are also provided. The present invention also encompasses the use of these C-terminal BGS-19 deletion polypeptides as immunogenic and/or antigenic epitopes as described elsewhere herein.

The invention also provides chimeric or fusion proteins. As used herein, a "chimeric protein" or "fusion protein" comprises all or part (preferably biologically active) of a polypeptide of the invention fused in-frame to a heterologous polypeptide. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein comprises a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (Ausubel et al., *Current Protocols in Molecular Biology*, eds., John Wiley & Sons, 1992). Other examples of eukaryotic heterologous signal sequences include the secretory sequences of melittin and human placental alkaline phosphatase (Stratapolynucleotide; La Jolla, Calif.). In yet another example, useful prokaryotic heterologous signal sequences include the phoA secretory signal (Sambrook et al., *Molecular Cloning: A Laboratory Manual*, 2nd ed., Cold Spring Harbor Laboratory, Cold Spring Harbor Laboratory Press, Cold Spring Harbor, N.Y., 1989) and the protein A secretory signal (Pharmacia Biotech; Piscataway, N.J.).

In yet another embodiment, the fusion protein is an immunoglobulin fusion protein in which all or part of a polypeptide of the invention is fused with sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands. The immunoglobulin fusion protein can, for example, comprise a portion of a polypeptide of the invention fused with the amino-terminus or the carboxyl-terminus of an immunoglobulin constant region (see, e.g., U.S. Pat. Nos. 5,714,147; 5,116,964; 5,514,582; 5,455,165).

Chimeric and fusion proteins of the invention can be produced by standard recombinant DNA techniques. In another embodiment, the fusion polynucleotide can be synthesized by conventional techniques including automated DNA synthesizers. Alternatively, PCR amplification of polynucleotide fragments can be carried out using anchor primers which give rise to complementary overhangs between two consecutive polynucleotide fragments which can subsequently be annealed and reamplified to polynucleotiderate a chimeric polynucleotide sequence (see, e.g., Ausubel et al., supra). Moreover, many expression vectors are commercially available that already encode a fusion moiety (e.g., a GST polypeptide). A polynucleotide encoding a polypeptide of the invention can be cloned into such an expression vector such that the fusion moiety is linked in-frame to the polypeptide of the invention.

A signal sequence of a polypeptide of the invention can be used to facilitate secretion and isolation of the secreted protein or other proteins of interest. Signal sequences are typically characterized by a core of hydrophobic amino acids which are polynucleotiderally cleaved from the mature protein during secretion in one or more cleavage events. Such signal peptides comprise processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a polynucleotide encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be polynucleotiderated by mutapolynucleotidesis, e.g., discrete point mutation or truncation. Moreover, variants of a polypeptide of the invention can be produced by directed evolution techniques (see, e.g., U.S. Pat. Nos. 6,309,883 and 6,238,884). For example, recursive ensemble mutapolynucleotidesis, a technique which enhances the frequency of functional mutants in the libraries, can be used in combination with the screening assays to identify variants of a protein of the invention (see, e.g., Arkin and Yourvan, 1992, "An algorithm for protein engineering: simulations of recursive ensemble mutapolynucleotidesis", Proc Natl Acad Sci 89:7811–7815; Delagrave et al., 1993, "Recursive ensemble mutapolynucleotidesis", Protein Eng. 6:327–331).

The polypeptides of the invention can exhibit post-translational modifications, including, but not limited to, glycosylations (e.g., N-linked or O-linked glycosylations), myristylations, palmitylations, acetylations and phosphorylations (e.g., serine/threonine or tyrosine). In one embodiment, the polypeptides of the invention exhibit reduced levels of O-linked glycosylation and/or N-linked glycosylation relative to endogenously expressed. In another embodiment, the polypeptides of the invention do not exhibit O-linked glycosylation or N-linked glycosylation.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

Recombinant Vectors and Host Cells

Another aspect of the invention pertains to vectors, preferably expression vectors, comprising a BGS-19 polynucleotide or a polynucleotide encoding a BGS-19 polypeptide, BGS-19 agonist, BGS-19 antagonist, inhibitor of a BGS-19 agonist, inhibitor of a BGS-19 antagonist, or a variant thereof. In a particular embodiment, an expression vector comprises a BGS-19 polynucleotide encoding a BGS-19 polypeptide of the invention (or a portion thereof).

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In polynucleotideral, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses).

A recombinant expression vector of the invention comprises a polynucleotide of the invention in a form suitable for expression of the polynucleotide in a host cell. This means that the recombinant expression vectors include one or more regulatory sequences, selected on the basis of the host cells to be used for expression, which is operably linked to the polynucleotide to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology*, Academic Press, San Diego, Calif. (1990) p. 185.

Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by polynucleotides as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, *Gene Expression Technology: Methods in Enzymology*, Academic Press, San Diego, Calif. (1990) p. 185. Alternatively, the recombinant expression vector can be transcribed and translated in vitro, for example using T7 promoter regulatory sequences and T7 polymerase.

Expression of proteins in prokaryotes is most often carried out in *E. coli* with vectors comprising constitutive or inducible promoters directing the expression of either fusion or non-fusion proteins. Fusion vectors add a number of amino acids to a protein encoded therein, usually to the amino terminus of the recombinant protein. Such fusion vectors typically serve at least three purposes: 1) to increase expression of recombinant protein; 2) to increase the solubility of the recombinant protein; and/or 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, Gene 67:31–40), pMAL (New England Biolabs, Beverly, Mass.) and pRIT5 (Pharmacia, Piscataway, N.J.) which fuse glutathione S-transferase ("GST"), maltose E binding protein, or protein A, respectively, to the target recombinant protein.

Examples of suitable inducible non-fusion *E. coli* expression vectors include pTrc (Amann et al., 1988, "Tightly regulated tac promoter vectors useful for the expression of unfused and fused proteins in *Escherichia coli*", Gene 69:301–315) and pET 11d (Studier et al., *Gene Expression Technology: Methods in Enzymology*, Academic Press, San Diego, Calif. (1990) pp. 60–89). Target polynucleotide expression from the pTrc vector relies on host RNA polymerase transcription from a hybrid trp-lac fusion promoter. Target polynucleotide expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 polynucleotide under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology*, Academic Press, San Diego, Calif. (1990) pp. 119–128). Another strategy is to alter the sequence of the polynucleotide to be inserted into an expression vector so that the individual codons for each amino acid are those preferentially utilized in *E. coli* (Wada et al., 1992, "Codon usage tabulated from the GenBank polynucleotidetic sequence data", Nucleic Acids Res. 20 Suppl:2111–2118). Such alteration of polynucleotides of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, "A novel leader peptide which allows efficient secretion of a fragment of human interleukin 1 beta in *Saccharomyces cerevisiae*", EMBO J. 6:229–234), pMFa (Kurjan and Herskowitz, 1982, "Structure of a yeast pheromone polynucleotide (MF alpha): a putative alpha-factor precursor contains four tandem copies of mature alpha-factor", Cell 30:933–943), pJRY88 (Schultz et al., 1987, Gene 54:113–123), pYES2 (Invitrogen Corp., San Diego, Calif.), and pPicZ (Invitrogen Corp., San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, "Production of human beta interferon in insect cells infected with a baculovirus expression vector", Mol Cell Biol. 3:2156–2165) and the pVL series (Lucklow and Summers, 1989, "High level expression of nonfused foreign polynucleotides with *Autographa californica* nuclear polyhedrosis virus expression vectors" Virology 170:31–39).

In yet another embodiment, a BGS-19 polynucleotide of the invention is expressed in mammalian cells using a mammalian expression vector. Examples of mammalian expression vectors include pCDM8 (Seed, 1987, "An LFA-3 cDNA encodes a phospholipid-linked membrane protein homologous to its receptor CD2", Nature 329:840) and pMT2PC (Kaufman et al., 1987, "Translational efficiency of polycistronic mRNAs and their utilization to express heterologous polynucleotides in mammalian cells", EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., *Molecular Cloning: A Laboratory Manual,* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the BGS-19 polynucleotide preferentially in a particular cell type (e.g., using tissue-specific regulatory elements to express the polynucleotide). Tissue-specific regulatory elements are known in the art. For example, the regulatory elements of imprinted polynucleotides can be used in vector constructs with BGS-19 polynucleotides. Non-limiting examples of suitable tissue-specific promoters include the albumin promoter (liver-specific; Pinkert et al., 1987, "An albumin enhancer located 10 kb upstream functions along with its promoter to direct efficient, liver-specific expression in transgenic mice", Genes Dev. 1:268–277), lymphoid-specific promoters (Calame and Eaton, 1988, "Transcriptional controlling elements in the immunoglobulin and T cell receptor loci", Adv. Immunol. 43:235–275), in particular promoters of T cell receptors (Winoto and Baltimore, 1989, "A novel, inducible and T cell-specific enhancer located at the 3' end of the T cell receptor alpha locus", EMBO J. 8:729–733) and immunoglobulins (Banerji et al., 1983, "A lymphocyte-specific cellular enhancer is located downstream of the joining region in immunoglobulin heavy chain polynucleotides", Cell 33:729–740; Queen and Baltimore, 1983, "Immunoglobulin polynucleotide transcription is activated by downstream sequence elements", Cell 33:741–748), neuron-specific promoters (e.g., the neurofilament promoter; Byrne and Ruddle, 1989, "Multiplex polynucleotide regulation: a two-tiered approach to transpolynucleotide regulation in transgenic mice", Proc Natl Acad Sci. 86:5473–5477), pancreas-specific promoters (Edlund et al., 1985, "Cell-specific expression of the rat insulin polynucleotide: evidence for role of two distinct 5' flanking elements", Science 230:912–916), and mammary gland-specific promoters (e.g., milk whey promoter; U.S. Pat. No. 4,873,316 and European Application Publication No. 264, 166). Developmentally-regulated promoters are also encompassed, for example the murine hox promoters (Kessel and Gruss, 1990, Science 249:374–379) and the α-fetoprotein promoter (Campes and Tilghman, 1989, Genes Dev. 3:537–546).

The invention further provides a recombinant expression vector comprising a BGS-19 polynucleotide of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a polynucleotide cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense polynucleotides are produced under the control of a high efficiency regulatory region, the activity of which can be determined by the cell type into which the vector is introduced.

In another embodiment, the expression characteristics of an endogenous BGS-19 polynucleotide within a cell, cell line or microorganism may be modified by inserting a DNA regulatory element heterologous to the endogenous polynucleotide of interest into the genome of a cell, stable cell line or cloned microorganism such that the inserted regulatory element is operatively linked with an endogenous BGS-19 polynucleotide and controls, modulates or activates the endogenous polynucleotide. For example, endogenous polynucleotides of the invention which are normally "transcriptionally silent", i.e., polynucleotides which are normally not expressed, or are expressed only at very low levels in a cell line or microorganism, may be activated by inserting a regulatory element which is capable of promoting the expression of a normally expressed polynucleotide product in that cell line or microorganism. Alternatively, transcriptionally silent, endogenous polynucleotides of the invention may be activated by insertion of a promiscuous regulatory element that works across cell types.

A heterologous regulatory element may be inserted into a stable cell line or cloned microorganism, such that it is operatively linked with and activates expression of an endogenous BGS-19 polynucleotide, using techniques, such as targeted homologous recombination, which are well known to those of skill in the art (See, e.g., U.S. Pat. Nos. 5,272,071 and 5,968,502; International Publication Nos. WO 91/06667 and WO 94/12650). Alternatively, non-targeted techniques (e.g., non-homologous recombination) well known in the art can be used (see, e.g., International Publication No. WO 99/15650).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding polynucleotiderations due to either mutation or environmental influences, such progeny may not, in fact, be identical to the parent cell, but are nevertheless within the scope of the term as used herein.

Accordingly, the present invention provides a host cell having an expression vector comprising a BGS-19 polynucleotide or a polynucleotide encoding a BGS-19 polypeptide, BGS-19 agonist, BGS-19 antagonist, inhibitor of a BGS-19 agonist, inhibitor of a BGS-19 antagonist, or a variant thereof. A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a polynucleotide that encodes a selectable marker (e.g., for resistance to antibiotics) is polynucleotiderally introduced into the host cells along with the polynucleotide of interest. Preferred selectable markers include those which confer resistance to drugs, such as G418, hygromycin and methotrexate. Cells stably transfected with the introduced polynucleotide can be identified by drug selection (e.g., cells that have incorporated the selectable marker polynucleotide will survive, while the other cells die).

A host cell of the invention, such as a prokaryotic or eukaryotic host cell in culture, can be used to produce a BGS-19 polypeptide of the invention. Accordingly, the invention further provides methods for producing a BGS-19 polypeptide of the invention using the host cells of the invention. In one embodiment, the method comprises culturing the host cell of invention (into which a recombinant expression vector encoding a BGS-19 polypeptide of the invention has been introduced) in a suitable medium such that the BGS-19 polypeptide is produced. In another embodiment, the method further comprises isolating the BGS-19 polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a BGS-19 polypeptide of the invention has been introduced. Such host cells can then be used to create non-human transgenic animals in which exogenous sequences encoding a polypeptide of the invention have been introduced into their genome or homologous recombinant animals in which endogenous sequences encoding a BGS-19 polypeptide of the invention sequences have been altered. Such animals are useful for studying the function and/or activity of the polypeptide and for identifying and/or evaluating modulators of polypeptide activity. In addition to particular polynucleotide expression and/or polypeptide expression phenotypes, the transgenic animals of the invention can exhibit any of the phenotypes (e.g., processes, disorder symptoms and/or disorders), as are described in the sections above. As used herein, a "transgenic animal" is a non-human animal, preferably a mammal, more preferably a rodent such as a rat or mouse, in which one or more of the cells of the animal includes a transpolynucleotide. Other examples of transgenic animals include non-human primates, sheep, dogs, cows, goats, chickens, amphibians, etc. A transpolynucleotide is exogenous DNA which is integrated into the genome of a cell from which a transgenic animal develops and which remains in the genome of the mature animal, thereby directing the expression of an encoded polynucleotide product in one or more cell types or tissues of the transgenic animal. As used herein, an "homologous recombinant animal" is a non-human animal, preferably a mammal, more preferably a mouse, in which an endogenous polynucleotide has been altered by homologous recombination between the endogenous polynucleotide and an exogenous DNA molecule introduced into a cell of the animal, e.g., an embryonic cell of the animal, prior to development of the animal.

A transgenic animal of the invention can be created by introducing a polynucleotide encoding a BGS-19 polypeptide of the invention (or a homolog thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transpolynucleotide to increase the efficiency of expression of the transpolynucleotide. A tissue-specific regulatory sequence(s) can be operably linked to the transpolynucleotide to direct expression of the polypeptide of the invention to particular cells. Methods for polynucleotiderating transgenic animals via embryo manipulation and microinjection, particularly animals such as mice, have become conventional in the art (see, e.g., U.S. Pat. Nos. 4,736,866; 4,870,009; 4,873,191; Hogan, 1986, *Manipulating the Mouse Embryo*, Cold Spring Harbor Laboratory Press, Cold Spring Harbor, N.Y.; Wakayama et al., 1999, "Mice cloned from embryonic stem cells", Proc Natl Acad Sci. 96:14984–14989). Similar methods are used for production of other transgenic animals. A transgenic founder animal can be identified based upon the presence of the transpolynucleotide in its genome and/or expression of mRNA encoding the transpolynucleotide in tissues or cells of the animals. A transgenic founder animal can then be used to breed additional animals carrying the transpolynucleotide. Moreover, transgenic animals carrying the transpolynucleotide can further be bred to other transgenic animals carrying other transpolynucleotides.

To create an homologous recombinant animal, a vector is prepared which comprises at least a portion of a polynucleotide encoding a polypeptide of the invention into which a deletion, addition or substitution has been introduced to thereby alter, e.g., functionally disrupt, the polynucleotide. In a preferred embodiment, the vector is designed such that, upon homologous recombination, the endogenous polynucleotide is functionally disrupted (i.e., no longer encodes a functional protein; also referred to as a "knock out" vector). Alternatively, the vector can be designed such that, upon homologous recombination, the endogenous polynucleotide is mutated or otherwise altered but still encodes functional protein (e.g., the upstream regulatory region can be altered to thereby alter the expression of the endogenous protein). In the homologous recombination vector, the altered portion of the polynucleotide is flanked at its 5' and 3' ends by additional nucleic acid sequences of the polynucleotide to allow for homologous recombination to occur between the exogenous polynucleotide carried by the vector and an endogenous polynucleotide in an embryonic stem cell. The additional flanking nucleic acid sequences are of sufficient length for successful homologous recombination with the endogenous polynucleotide. Typically, several kilobases of flanking DNA (both at the 5' and 3' ends) are included in the vector (See, e.g., Thomas and Capecchi, 1987, Cell. 51:503 for a description of homologous recombination vectors). The vector is introduced into an embryonic stem cell line (e.g., by electroporation) and cells in which the polynucleotide has been introduced by homologous recombination are selected (See, e.g., Li et al., 1992, Cell 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transpolynucleotide. Methods for constructing homologous recombination vectors and homologous recombinant animals are described further in Bradley, 1991, Current Opinion in Biotechnology 2:823–829 and in PCT Publication Nos. WO 90/11354, WO 91/01140, WO 92/0968 and WO 93/04169.

In another embodiment, transgenic non-human animals can be produced which contain selected systems which allow for regulated expression of the transpolynucleotide. One example of such a system is the cre/loxP recombinase system of bacteriophage P1 (see, e.g., Lakso et al., 1992, Proc Natl Acad Sci. 89:6232–6236). Another example of a recombinase system is the FLP recombinase system of *Saccharomyces cerevisiae* (O'Gorman et al., 1991, Science 251:1351–1355). If a cre/loxP recombinase system is used to regulate expression of the transpolynucleotide, animals comprising transpolynucleotides encoding both the Cre recombinase and a selected protein are required. Such animals can be provided through the construction of "double" transgenic animals, e.g., by mating two transgenic animals, one comprising a transpolynucleotide encoding a selected protein and the other comprising a transpolynucleotide encoding a recombinase.

Clones of the non-human transgenic animals described herein can also be produced according to the methods described in Wilmut et al., 1997, Nature 385:810–813 and PCT Publication Nos. WO 97/07668 and WO 97/07669.

Agonists and Antagonists of BGS-19 Polynucleotides and Polypeptides

The present invention relates to agonists or antagonists of a BGS-19 polynucleotide, BGS-19 polypeptide, or agonists or antagonists of complexes comprising a BGS-19 polynucleotide and/or BGS-19 polypeptide.

For example, variants of the polypeptides of the invention have an altered amino acid sequence that can function as agonists (e.g., mimetics) or as antagonists. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the invention which function as either agonists (mimetics) or as antagonists can be identified by screening combinatorial libraries of mutants, e.g., truncation mutants, of the protein of the invention for agonist or antagonist activity. In one embodiment, a library of variants is polynucleotiderated by combinatorial mutapolynucleotidesis at the nucleic acid level. Such a library of variants can be produced by, for example, enzymatically ligating a mixture of synthetic oligonucleotides into polynucleotide sequences such that a depolynucleotiderate set of potential protein sequences is expressible as individual polypeptides, or alternatively, as a set of larger fusion proteins (e.g., for phage display). There are a variety of methods which can be used to produce libraries of potential variants of the polypeptides of the invention from a depolynucleotiderate oligonucleotide sequence. Methods for synthesizing depolynucleotiderate oligonucleotides are known in the art (see, e.g., Narang, 1983, Tetrahedron 39:3; Itakura et al., 1984, Annu Rev Biochem. 53:323; Itakura et al., 1984, Science 198:1056; Ike et al., 1983, Nucleic Acid Res. 11:477).

In addition, libraries of fragments of the coding sequence of a polypeptide of the invention can be used to polynucleotiderate a variegated population of polypeptides for screening and subsequent selection of variants. For example, a library of coding sequence fragments can be polynucleotiderated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening polynucleotide products of combinatorial libraries made by point mutations or truncation, and for screening cDNA libraries for polynucleotide products having a selected property. The most widely used techniques, which are amenable to high through-put analysis, for screening large polynucleotide libraries typically include cloning the polynucleotide library into replicable expression vectors, transforming appropriate cells with the resulting library of vectors, and expressing the combinatorial polynucleotides under conditions in which detection of a desired activity facilitates isolation of the vector encoding the polynucleotide whose product was detected.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

BGS-19 Antisense Oligonucleotides

The present invention relates to antagonists in the form of antisense polynucleotides, i.e., molecules which are complementary to a sense nucleic acid encoding a polypeptide of the invention, e.g., complementary to the coding strand of a double-stranded cDNA molecule or complementary to an mRNA sequence. BGS-19 antisense molecules are fully described in Section 5.2 supra.

BGS-19 Antibodies

The present invention also relates to agonists or antagonists in the form of anti-BGS-19 antibodies. An isolated polypeptide of the invention, or a fragment thereof, can be used as an immunogen to polynucleotiderate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) consecutive amino acid residues of the amino acid sequence depicted in FIGS. 2A–B or FIGS. 1A–C, and encompasses an epitope of the protein such that an antibody raised against the peptide forms a specific immune complex with the protein.

In one embodiment, the invention provides substantially purified antibodies or fragments thereof, including human or non-human antibodies or fragments thereof, which antibodies or fragments specifically bind to a polypeptide of the invention comprising an amino acid sequence selected from the group consisting of: the amino acid sequence depicted in FIGS. 2A–B or FIGS. 1A–C; a fragment of at least 8 contiguous amino acid residues of the amino acid sequence depicted in FIGS. 2A–B or FIGS. 1A–C; an amino acid sequence which is at least 95% identical to the amino acid sequence presented in depicted in FIGS. 2A–B or FIGS. 1A–C, wherein the percent identity is determined using the ALIGN program of the GCG software package with a PAM120 weight residue table, a gap length penalty of 12, and a gap penalty of 4, and an amino acid sequence which is encoded by a polynucleotide which hybridizes to the polynucleotide consisting of the sequence depicted in FIGS. 2A–B or 3 under conditions of hybridization of 6×SSC at 45° C. and washing in 0.2×SSC, 0. 1% SDS at 65° C. In various embodiments, the substantially purified antibodies of the invention, or fragments thereof, can be human, non-human, chimeric and/or humanized antibodies.

Preferred epitopes encompassed by the antigenic peptide are regions that are located on the surface of the protein, e.g., hydrophilic regions. Hydropathy plots of the polypeptides of the invention, or similar analyses, can be used to identify hydrophilic regions. In certain embodiments, BGS-19 polynucleotides are present as part of larger polynucleotides comprising nucleotide sequences that encode heterologous sequences (e.g., vector, expression vector, or fusion protein). These nucleotides can then be used to express proteins which can be used as immunogens to polynucleotiderate an immune response, or more particularly, to polynucleotiderate polyclonal or monoclonal antibodies specific to the expressed protein.

An immunogen typically is used to prepare antibodies by immunizing a suitable subject, (e.g., rabbit, goat, mouse or other mammal). An appropriate immunogenic preparation can comprise, for example, recombinantly expressed or chemically synthesized polypeptide. The preparation can further include an adjuvant, such as Freud's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that comprise an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally comprises the polypeptide. Examples of immunologically active portions of immunoglobulin molecules include F(ab) and F(ab')$_2$ fragments which can be polynucleotiderated by treating the antibody with an enzyme such as pepsin. The invention provides polyclonal and monoclonal antibodies. The term "monoclonal antibody" or "monoclonal antibody composition", as used herein, refers to a population of antibody molecules that comprise only one species of an antigen binding site capable of immunoreacting with a particular epitope.

Polyclonal antibodies can be prepared as described above by immunizing a suitable subject with a BGS-19 polypeptide of the invention as an immunogen. Preferred polyclonal antibody compositions are ones that have been selected for antibodies directed against a polypeptide or polypeptides of the invention. Particularly preferred polyclonal antibody preparations are ones that comprise only antibodies directed against a polypeptide or polypeptides of the invention. Particularly preferred immunogen compositions are those that comprise no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay ("ELISA") using immobilized polypeptide. If desired, the antibody molecules can be isolated from the mammal (e.g., from the blood) and further purified by well-known techniques, such as protein A chromatography to obtain the IgG fraction. Alternatively, antibodies specific for a BGS-19 protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample comprising antibodies directed against a large number of different epitopes, thereby polynucleotiderating a substantially purified antibody composition, i.e., one that is substantially free of contaminating antibodies. By a substantially purified antibody composition is meant, in this context, that the antibody sample comprises at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, 1975, Nature 256:495–497, the human B cell hybridoma technique (Kozbor et al., 1983, Immunol Today 4:72), the EBV-hybridoma technique (Cole et al., 1985, *Monoclonal Antibodies and Cancer Therapy*, Alan R. Liss, Inc., pp. 77–96) or trioma techniques. The technology for producing hybridomas is well known (See, e.g., *Current Protocols in Immunology,* 1994, Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for polynucleotiderating and screening phage display libraries are commercially available (e.g., the Pharmacia *Recombinant Phage Antibody System*, Catalog No. 27–9400–01; and the Stratapolynucleotide *SurfZAP Phage Display Kit*, Catalog No. 240612). Additionally, examples of methods and reagents particularly amenable for use in polynucleotiderating and screening an antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Biotechnology 9:1370–1372; Hay et al., 1992, Hum Antibod Hybridomas 3:81–85; Huse et al., 1989, Science 246:1275–1281; Griffiths et al., 1993, *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region (see, e.g., Cabilly et al., U.S. Pat. No. 4,816,567; and Boss et al., U.S. Pat. No. 4,816,397, which are incorporated herein by reference in their entirety). Humanized antibodies are antibody molecules from non-human species having one or more complementarity determining regions ("CDRs") from the non-human species and a framework region from a human immunoglobulin molecule. (See, e.g., Queen, U.S. Pat. No. 5,585,089, which is incorporated herein by reference in its entirety). Such chimeric and humanized monoclonal antibodies can be produced by recombinant DNA techniques known in the art, (see, e.g., PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041–1043; Liu et al., 1987, Proc Natl Acad Sci. 84:3439–3443; Liu et al., 1987, J. Immunol. 139:3521–3526; Sun et al., 1987, Proc Natl Acad Sci. 84:214–218; Nishimura et al., 1987, Cancer Res. 47:999–1005; Wood et al., 1985, Nature 314:446–449; Shaw et al., 1988, J Natl Cancer Inst. 80:1553–1559; Morrison, 1985, Science 229:1202–1207; Oi et al., 1986, Biotechniques 4:214; U.S. Pat. No. 5,225,539; Jones et al., 1986, Nature 321:552–525; Verhoeyan et al., 1988, Science 239: 1534; Beidler et al., 1988, J. Immunol. 141:4053–4060).

Completely human antibodies are particularly desirable for therapeutic treatment of human patients. Such antibodies can be produced, for example, using transgenic mice which are incapable of expressing endogenous immunoglobulin heavy and light chains polynucleotides, but which can express human heavy and light chain polynucleotides. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transpolynucleotides harbored by the transgenic mice rearrange during B cell differentiation, and subsequently undergo class switching and somatic mutation. Thus, IgG, IgA and IgE antibodies can be produced using techniques well known in the art, (see, e.g., Lonberg and Huszar, 1995, Int. Rev. Immunol. 13:65–93; U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies which recognize a selected epitope can be polynucleotiderated using a technique referred to as "guided selection." In this approach a selected non-human monoclonal antibody, e.g., a mouse antibody, is used to guide the selection of a completely human antibody recognizing the same epitope (see, e.g., Jespers et al., 1994, Biotechnology 12:899–903).

An antibody directed against a BGS-19 polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-4 ("IL-4"), interleukin-6 ("IL-6"), interleukin-7 ("IL-7"), granulocyte macrophase colony stimulating factor ("GM-CSF"), granulocyte colony stimulating factor ("G-CSF"), interleukin-10 ("IL-10"), interleukin-12 ("IL-12"), interleukin-15 ("IL-15"), interferon-γ ("IFN-γ"), interferon-α ("IFN-α"), or other immune factors or growth factors.

Techniques for conjugating such therapeutic moiety to antibodies are well known (see, e.g., Arnon et al., "Monoclonal Antibodies For Immunotargeting Of Drugs In Cancer Therapy", in *Monoclonal Antibodies And Cancer Therapy*, Reisfeld et al. (eds.), Alan R. Liss, Inc. (1985) pp. 243–256; Hellstrom et al., "Antibodies For Drug Delivery" in *Controlled Drug Delivery* (2nd Ed.), Robinson et al. (eds.) Marcel Dekker, Inc. (1987) pp. 623–653; Thorpe, "Antibody Carriers Of Cytotoxic Agents In Cancer Therapy: A Review", in *Monoclonal Antibodies '84: Biological And Clinical Applications*, Pinchera et al. (eds.) (1985) pp. 475–506; "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press (1985) pp. 303–316; Thorpe et al., 1992, "The Preparation And Cytotoxic Properties Of Antibody-Toxin Conjugates", Immunol Rev. 62:119–158).

Alternatively, an antibody can be conjugated to a second antibody to form an antibody heteroconjugate as described in U.S. Pat. No. 4,676,980.

An antibody with or without a therapeutic moiety conjugated to it can be used as a therapeutic that is administered alone or in combination with chemotherapeutic agents.

Alternatively, an antibody of the invention can be conjugated to a second antibody to form an "antibody heteroconjugate" as described in U.S. Pat. No. 4,676,980 or alternatively, two antibodies can be conjugated to each other to create a bispecific heteromers, or an "antibody heteropolymer" as described in U.S. Pat. Nos. 5,470,570 and 5,487,890.

An antibody with or without a therapeutic moiety conjugated to it can be used as a therapeutic that is administered alone or in combination with cytotoxic factor(s) and/or cytokine(s).

Functional Analysis of BGS-19

Human Expression Pattern of BGS-19

The expression profile of the BGS-19 polypeptide was assesed by measuring the steady state levels of BGS-19 mRNA by quantitative PCR. First strand cDNA was made from commercially available mRNA (Clontech) and subjected to real time quantitative PCR using a PE 5700 instrument (Applied Biosystems, Foster City, Calif.) which detects the amount of DNA amplified during each cycle by the fluorescent output of SYBR green, a DNA binding dye specific for double strands. The BGS-19 polypeptide showed predominately high expression levels in spleen; significantly in lung, spinal cord, and to a lesser extent, in other tissues as shown in FIG. 6.

Based upon the observed homology, the polypeptide of the present invention may share at least some biological activity with immunoglobulin-like domain containing proteins, specifically with human siglec proteins, more specifically with human siglec proteins referenced elsewhere herein.

Figure 6:
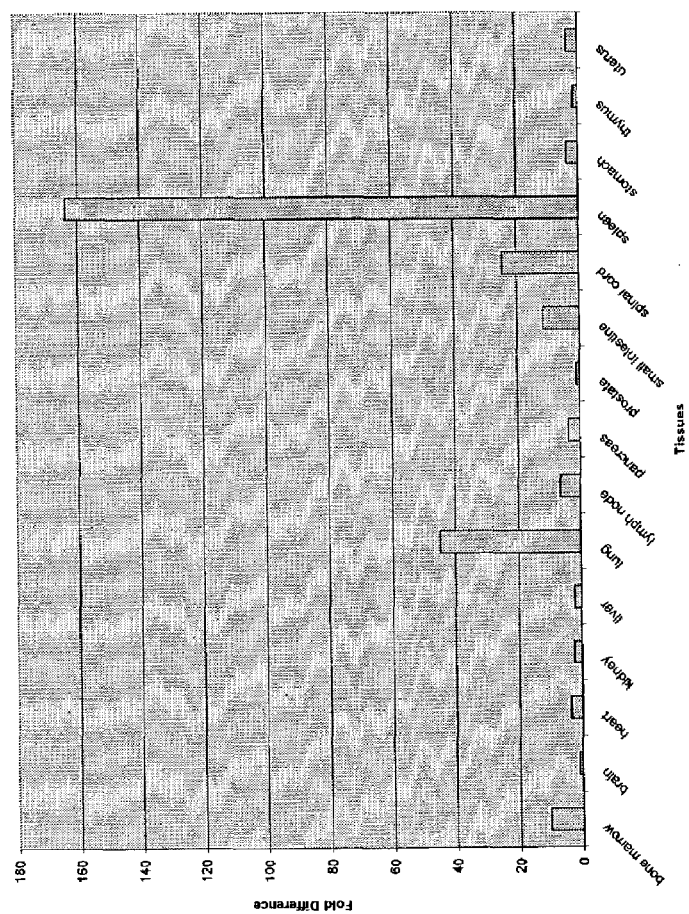
FIG. 6. Bar graph showing significant expression of BGS-19 in bone marrow, lung, lymph node, small intestine, spinal cord, and spleen.

Expanded analysis of BGS-19 expression levels by TaqMan™ quantitative PCR (See FIG. 7) extended the expression profile achieved previously (FIG. 6). BGS-19 mRNA was expressed predominately in the ovary (9000 fold over other tissues). Significant expression was observed in the testis, adrenal gland, the parenchyma of the spleen and throughout the stomach. BGS-19 was expressed in non-ovarian tissues at levels that were approximately nine fold less than that observed in the ovary.

Morever, an additional analysis of BGS-19 expression levels by TaqMan™ quantitative PCR (see FIG. 8) in disease cells and tissues indicated that the BGS-19 polypeptide is differentially expressed in ovarian tumor tissues relative to normal ovarian tissue. In the ovarian cancer results, an average of 5 samples showed a 25-fold reduction in BGS-19 steady state RNA over that observed in 5 normal samples (P=0.0145). These data suggest that BGS-19 can be used as a diagnostic marker of various ovarian cancers, and that replacing BGS-19 function may offer a novel therapeutic approach to the treatment of ovarian cancer.

The strong homology to human immunoglobulin-like domain containing proteins, combined with the predominate localized expression in spleen tissue suggests the BGS-19 polynucleotides and polypeptides, including modulators thereof, may be useful in treating, diagnosing, prognosing, and/or preventing ovarian diseases and/or disorders. Such disorders include the following, non-limiting, diseases or disorders of the ovary, in addition to disorders related to ovarian disorders: ovaran cancer; dysfunctional uterine bleeding; amenorrhea; primary dysmenorrhea; sexual dysfunction; infertility; pelvic inflammatory disease; endometriosis; placental aromatase deficiency; premature menopause; placental dysfunction; hormone deficiency; estrogen deficiency; aberrant androgen metabolism; gaberrant onset of female puberty; aberrant showing of female primary sexual characteristics; aberrant showing of female secondary sexual characteristics; precocious puberty; precocious pseudopuberty; incomplete isosexual precocity; premature thelarche; premature adrenarche; premature pubarche; polycystic ovarian disease; aberrant ovarian cycle; menorrhagia; metrorrhagia; menometrorrhagia; dysmenorrhea; hypomenorrhea; polymenorrhea; dysfunctional uterine bleeding; resistant-ovary syndrome; and/or hermaphroditism.

The strong homology to human immunoglobulin-like domain containing proteins, combined with the predominate localized expression in spleen tissue suggests the BGS-19 polynucleotides and polypeptides, including modulators thereof, may be useful in treating, diagnosing, prognosing, and/or preventing immune diseases and/or disorders. Representative uses are described elsewhere herein. Briefly, the strong expression in immune tissue indicates a role in regulating the proliferation; survival; differentiation; and/or activation of hematopoietic cell lineages, including blood stem cells.

The BGS-19 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The BGS-19 polypeptide may be useful for modulating cytokine production, antigen presentation, or other processes, such as for boosting immune responses, etc.

Moreover, the protein may represent a secreted factor that influences the differentiation or behavior of other blood cells, or that recruits hematopoietic cells to sites of injury. Thus, this polynucleotide product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be polynucleotidetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinopolynucleotidemia, factor deficiencies), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. These molecules could be important in the treatment or prevention of heart attacks (infarction), strokes, or scarring.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/ or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium*, *Mycobacterium*, *Norcardia*), Cryptococcus neoformans, Aspergillosis, Bacillaceae (e.g., Anthrax, *Clostridium*), Bacteroidaceae, Blastomycosis, *Bordetella*, *Borrelia* (e.g., *Borrelia burgdorferi*), Brucellosis, *Candidiasis*, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella*, *Salmonella* (e.g., *Salmonella typhi*, and *Salmonella paratyphi*), *Serratia*, *Yersinia*), Erysipelothrix, *Helicobacter*, Legionellosis, Leptospirosis, Listeria, Mycoplasmatales, *Mycobacterium leprae*, *Vibrio cholerae*, Neisseriaceae (e.g., Acinetobacter, Gonorrhea, Menigococcal), *Meisseria meningitidis*, Pasteurellacea Infections (e.g., Actinobacillus, Heamophilus (e.g., *Heamophilus influenza* type B), Pasteurella), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal polynucleotiderated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of depolynucleotiderate oligonucleotide probes to screen a cDNA library to identify the polynucleotides encoding the putative receptors.

Moreover, the techniques of polynucleotide-shuffling, motif-shuffling, exon-shuffling, and/or codon-shuffling (collectively referred to as "DNA shuffling") may be employed to modulate the activities of polypeptides of the invention thereby effectively polynucleotiderating agonists and antagonists of polypeptides of the invention. See polynucleotiderally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutapolynucleotidesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphopolynucleotidetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-betal, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

The strong homology to human immunoglobulin-like domain containing proteins, combined with the localized expression in lung tissue also emphasizes the potential utility for BGS-19 polynucleotides and polypeptides in treating, diagnosing, prognosing, and/or preventing pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, polynucleotides and polypeptides, including fragments and/or antagonists thereof, have uses which include, directly or indirectly, treating, preventing, diagnosing, and/or prognosing the following, non-limiting, pulmonary infections: pnemonia, bacterial pnemonia, viral pnemonia (for example, as caused by Influenza virus, Respiratory syncytial virus, Parainfluenza virus, Adenovirus, Coxsackievirus, Cytomegalovirus, Herpes simplex virus, Hantavirus, etc.), *mycobacteria pnemonia* (for example, as caused by *Mycobacterium tuberculosis*, etc.) mycoplasma pnemonia, fungal pnemonia (for example, as caused by *Pneumocystis carinii, Histoplasma capsulatum, Coccidioides immitis, Blastomyces dermatitidis, Candida* sp., *Cryptococcus neoformans, Aspergillus* sp., *Zygomycetes*, etc.), Legionnaires' Disease, *Chlamydia pnemonia*, aspiration pnemonia, *Nocordia* sp. Infections, parasitic pnemonia (for example, as caused by Strongyloides, *Toxoplasma gondii*, etc.) necrotizing pnemonia, in addition to any other pulmonary disease and/or disorder (e.g., non-pneumonia) implicated by the causative agents listed above or elsewhere herein.

The strong homology to human immunoglobulin-like domain containing proteins, combined with the localized expression in spinal cord suggests the BGS-19 polynucleotides and polypeptides may be useful in treating, diagnosing, prognosing, and/or preventing neurodepolynucleotiderative disease states, behavioral disorders, or inflammatory conditions. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this polynucleotide product in regions of the brain indicates it plays a role in normal neural function. Potentially, this polynucleotide product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or depolynucleotideration of neurons, or demyclination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) depolynucleotiderative lesions, in which a portion of the nervous system is destroyed or injured as a result of a depolynucleotiderative process including but not limited to depolynucleotideration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wemicke disease, tobacco-alcohol amblyopia, Marchiafava-Bignami disease (primary depolynucleotideration of the corpus callosum), and alcoholic cerebellar depolynucleotideration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, depolynucleotiderative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Screening Assays

The present invention also relates to screening assays particularly useful in drug discovery efforts. Thus, the invention provides methods for screening for compounds that bind and/or modulate a BGS-19 polynucleotide or polypeptide. Accordingly, in one embodiment, the invention provides a method for detecting an analyte that binds a BGS-19 polypeptide comprising the steps of contacting the BGS-19 polypeptide, or a variant thereof, with an analyte under conditions that allow the BGS-19 polypeptide to be bound by the analyte, and detecting binding of the BGS-19 polypeptide to the analyte, wherein detection of binding indicates presence of an analyte that binds the BGS-19 polypeptide. In particular embodiments, such methods can be used to detect and identify compounds that bind or affect the pharmacokinetics (e.g., catalytic activity) of a polypeptide of the invention.

In particular embodiments, the analyte is a protein. Accordingly, in one embodiments, the present invention provides a method for identifying a BGS-19-binding protein comprising the steps of contacting a BGS-19 polypeptide, or a variant thereof, with an array comprising a plurality of proteins, and detecting binding of the BGS-19 polypeptide to a protein on the array, wherein detection of binding indicates presence of a BGS-19-binding protein.

The present invention also relates to methods for detecting an analyte that binds a BGS-19 polynucleotide comprising the steps of contacting the BGS-19 polynucleotide, or a variant thereof, with an analyte under conditions that allow the BGS-19 polynucleotide to be bound by the analyte, and detecting binding of the BGS-19 polynucleotide to the analyte, wherein detection of binding indicates presence of an analyte that binds the BGS-19 polynucleotide. In particular embodiments, such methods can be used to detect and identify compounds that modulate transcription or translation of a BGS-19 polynucleotide product.

Methods for Detecting Modulators of a BGS-19 Polynucleotide or Polypeptide

The present invention relates to methods for detecting and identifying proteins that bind BGS-19 DNA sequences, such proteins including, but not limited to, proteins that affect DNA conformation and proteins that modulate transcriptional activity (e.g., transcription factors, proteins that bind enhancers). In particular embodiments, the present invention provides methods for detecting and identifying factors that bind BGS-19 RNA sequences, such factors including, but not limited to, proteins, steroid hormones, or other small molecules. In further embodiments, the BGS-19 RNA-binding factors modulate translational efficacy and/or affect RNA stability.

The present invention also relates to methods for detecting and identifying BGS-19 agonists, antagonists, as well as activators and inhibitors thereof. In specific non-limiting embodiments, BGS-19 agonists, BGS-19 antagonists, inhibitors of BGS-19 agonists, activators of BGS-19 agonists, inhibitors of BGS-19 antagonists and activators of BGS-19 antagonists are small molecules (i.e., less than 500 daltons) that bind a BGS-19 polynucleotide or BGS-19 polypeptide of the invention.

The present invention also relates to methods for screening for proteins that bind specific domains of a BGS-19 polypeptide, wherein the domains exhibit a biological activity. In one embodiment, the invention provides a method for identifying a protein having a SH2 domain comprising the steps of contacting a SH2-binding domain of a BGS-19 polypeptide, or a variant thereof, with an analyte under conditions that allow the SH2-binding domain to be bound by the analyte, and detecting binding of the SH2-binding domain to the analyte, wherein detection of binding indicates the presence of a protein having a SH2 domain. In a further embodiment, the SH2-binding domain of the BGS-19 protein comprises an immunotyrosine-based inhibition motif ("ITIM").

Accordingly, the present invention provides isolated BGS-19 polynucleotides, or derivatives thereof, as probes that can be used to screen for DNA-binding proteins including, but not limited to, proteins that affect DNA conformation or modulate transcriptional activity (e.g., enhancers, transcription factors). In another embodiment, such probes can be used to screen for RNA-binding factors, including but not limited to proteins, steroid hormones, or other small molecules. In yet another embodiment, such probes can be used to detect and identify molecules that bind or affect the pharmacokinetics or activity (e.g., enzymatic activity) of a polypeptide of the invention.

In one embodiment, a screening assay of the invention can identify a test compound that is useful for increasing or decreasing the translation of a BGS-19 mRNA, for example, by binding to one or more regulatory elements in the 5' untranslated region, the 3' untranslated region, or the coding region of the mRNA. Compounds that bind to mRNA can, inter alia, increase or decrease the rate of mRNA processing, alter its transport through the cell, prevent or enhance binding of the mRNA to ribosomes, suppressor proteins or enhancer proteins, or alter mRNA stability. Accordingly, compounds that increase or decrease mRNA translation can be used to treat or prevent disease. For example, diseases such as cancer, associated with overproduction of proteins, such as Ras, can be treated or prevented by decreasing translation of the mRNA that codes for the overproduced protein, thus inhibiting production of the protein. Conversely, the symptoms of diseases associated with decreased protein function, such as hemophilia, may be treated by increasing translation of mRNA coding for the protein whose function is decreased, e.g., factor IX in some forms of hemophilia.

Accordingly, in one embodiment, a compound identified by a screening assay of the invention inhibits the production of a BGS-19 protein. In a further embodiment, the compound inhibits the translation of a BGS-19 mRNA.

The invention provides a method for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art (see, e.g., DeWitt et al., 1993, Proc Natl Acad Sci. 90:6909; Erb et al., 1994, Proc Natl Acad Sci. 91:11422; Zuckermann et al., 1994, J Med Chem. 37:2678; Cho et al., 1993, Science 261:1303; Carrell et al., 1994, Angew Chem Int Ed Encl. 33:2059; Carell et al., 1994, Angew Chem Int Ed Encl. 33:2061; Gallop et al., 1994, J Med Chem. 37:1233).

Libraries of compounds may be presented in solution (e.g., Houghten, 1992, Biotechniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223, 409), plasmids (Cull et al., 1992, Proc Natl Acad Sci. 89:1865–1869) or phage (Scott and Smith, 1990, Science 249:386–390; Devlin, 1990, Science 249:404–406; Cwirla et al., 1990, Proc Natl Acad Sci. 87:6378–6382; Felici, 1991, J Mol Biol. 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a BGS-19 polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal polynucleotiderated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{+2}$, diacylglycerol, IP3, etc.), detecting catalytic/enzymatic activity of the target on an appropriate substrate, detecting the induction of a reporter polynucleotide (e.g., a regulatory element that is responsive to a polypeptide of the invention operably linked to a polynucleotide encoding a detectable marker, e.g., luciferase), or detecting a cellular response, for example, cellular differentiation, or cell proliferation.

In yet another embodiment, an assay of the present invention is a cell-free assay comprising contacting a BGS-19 polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a BGS-19 polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a BGS-19 polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, isotridecypoly(ethylene glycol ether)n, 3-[(3-cholamidopropyl) dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the BGS-19 polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for comprising the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtiter plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a BGS-19 polypeptide of the invention are identified in a method in which a cell is contacted with a candidate compound and the expression of the selected mRNA or protein (i.e., the mRNA or protein corresponding to a polypeptide or polynucleotide of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a BGS-19 polypeptide of the inventions can be used as "bait proteins" in a two-hybrid assay or three hybrid assay (see, e.g., U.S. Pat. No. 5,283,317; Zervos et al., 1993, Cell 72:223–232; Madura et al., 1993, J Biol Chem. 268:12046–12054; Bartel et al., 1993, Biotechniques 14:920–924; Iwabuchi et al., 1993, Oncopolynucleotide 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

The invention also provides a method for screening for compounds (e.g., potentially useful drugs) that bind a BGS- 19 polynucleotide or polypeptide. In one embodiment, test compounds are assayed for binding to a BGS-19 polynucleotide or polypeptide. In another embodiment, test compounds are assayed for binding to a complex comprising a BGS-19 polynucleotide (e.g., transcriptional complex) or a BGS-19 polypeptide (hetero- or homo-dimer or multimer). In a further embodiment, test compounds are assayed for binding to a BGS-19 polypeptide when bound to a second, different polypeptide.

The invention also provides a method for screening for compounds (e.g., potentially useful drugs) that inhibit the binding of a BGS-19 polynucleotide or polypeptide to an analyte, target molecule or binding partner. In one embodiment, test compounds are assayed to prevent formation of complexes comprising a BGS-19 polynucleotide (e.g., transcriptional complex) or a BGS-19 polypeptide (hetero- or homo-dimer or multimer). In a further embodiment, test compounds are assayed for ability to inhibit binding of a BGS-19 polypeptide to a second, different polypeptide.

In particular embodiments, the test compounds are assayed for the ability to interfere with existing complexes or existing interactions of a BGS-19 polynucleotide or polypeptide with another compound. In other embodiments, the test compound is incubated first with the BGS-19 polynucleotide or polypeptide, prior to addition of the analyte, target molecule or binding partner, after which the ability to inhibit binding is assayed. In yet other embodiments, the test compound is incubated first with the analyte, target molecule or binding partner, prior to addition of the BGS-19 polynucleotide or polypeptide, after which the ability to inhibit binding is assayed.

For example, and not by way of limitation, polynucleotides, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a polynucleotide of the invention and other polynucleotides implicated in the disorder. The levels of polynucleotide expression (i.e., a polynucleotide expression pattern) can be quantified by Northern blot analysis or RT-PCR, as described herein, or alternatively by measuring the amount of protein produced, by one of the methods as described herein, or by measuring the levels of activity of a polynucleotide of the invention or other polynucleotides. In this way, the polynucleotide expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or polynucleotide of the invention in the pre-administration sample; (iii) obtaining one or more post-administration samples from the subject; (iv) detecting the level the of the polypeptide or polynucleotide of the invention in the post-administration samples; (v) comparing the level of the polypeptide or polynucleotide of the invention in the pre-administration sample with the level of the polypeptide or polynucleotide of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

This invention further pertains to uses of agents identified by the above-described screening assays.

Drug Screening

The present invention also relates to screening assays particularly useful in drug discovery efforts. Thus, the invention provides methods for screening for compounds that bind and/or modulate a BGS-19 polynucleotide or polypeptide. Accordingly, in one embodiment, the invention provides a method for detecting an analyte that binds a BGS-19 polypeptide comprising the steps of contacting the BGS-19 polypeptide, or a variant thereof, with an analyte under conditions that allow the BGS-19 polypeptide to be bound by the analyte, and detecting binding of the BGS-19 polypeptide to the analyte, wherein detection of binding indicates presence of an analyte that binds the BGS-19 polypeptide. In particular embodiments, such methods can be used to detect and identify compounds that bind or affect the pharmacokinetics (e.g., catalytic activity) of a polypeptide of the invention.

In particular embodiments, the analyte is a protein. Accordingly, in one embodiments, the present invention provides a method for identifying a BGS-19-binding protein comprising the steps of contacting a BGS-19 polypeptide, or a variant thereof, with an array comprising a plurality of proteins, and detecting binding of the BGS-19 polypeptide to a protein on the array, wherein detection of binding indicates presence of a BGS-19-binding protein.

Using a BGS-19 polynucleotide, BGS-19 polypeptide, and/or a BGS-19-binding protein, a screening assay against, for example, a defined collection of molecules or a biological sample, can polynucleotiderate a signature of the metabolic state or biological response. Many protein arrays, antigen arrays, DNA arrays etc., known in the art, can be screened using a BGS-19 polynucleotide, polypeptide, antagonist, agonist and/or a BGS-19-binding protein to determine binding patterns. Many similar screening assays are known in the art and can be adapted for the present invention to, for example, determine a diagnosis or prognosis or monitor treatment or progression of a disorder.

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human BGS-19 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a BGS-19 polypeptide, or a bindable peptide fragment, of this invention, comprising providing a plurality of compounds, combining the BGS-19 polypeptide, or a bindable peptide fragment, with each of a plurality of compounds for a time sufficient to allow binding under suitable conditions and detecting binding of the BGS-19 polypeptide or peptide to each of the plurality of test compounds, thereby identifying the compounds that specifically bind to the BGS-19 polypeptide or peptide.

Methods of identifying compounds that modulate the activity of the novel human BGS-19 polypeptides and/or peptides are provided by the present invention and comprise combining a potential or candidate compound or drug modulator of potassium channel beta subunit biological activity with an BGS-19 polypeptide or peptide, for example, the BGS-19 amino acid sequence as set forth in SEQ ID NOS:2, and measuring an effect of the candidate compound or drug modulator on the biological activity of the BGS-19 polypeptide or peptide. Such measurable effects include, for example, physical binding interaction; the ability to cleave a suitable potassium channel beta subunit substrate; effects on native and cloned BGS-19-expressing cell line; and effects of modulators or other potassium channel beta subunit-mediated physiological measures.

Another method of identifying compounds that modulate the biological activity of the novel BGS-19 polypeptides of the present invention comprises combining a potential or candidate compound or drug modulator of a potassium channel beta subunit biological activity with a host cell that expresses the BGS-19 polypeptide and measuring an effect of the candidate compound or drug modulator on the biological activity of the BGS-19 polypeptide. The host cell can also be capable of being induced to express the BGS-19 polypeptide, e.g., via inducible expression. Physiological effects of a given modulator candidate on the BGS-19 polypeptide can also be measured. Thus, cellular assays for particular potassium channel beta subunit modulators may be either direct measurement or quantification of the physical biological activity of the BGS-19 polypeptide, or they may be measurement or quantification of a physiological effect. Such methods preferably employ a BGS-19 polypeptide as described herein, or an overexpressed recombinant BGS-19 polypeptide in suitable host cells containing an expression vector as described herein, wherein the BGS-19 polypeptide is expressed, overexpressed, or undergoes upregulated expression.

Another aspect of the present invention embraces a method of screening for a compound that is capable of modulating the biological activity of a BGS-19 polypeptide, comprising providing a host cell containing an expression vector harboring a nucleic acid sequence encoding a BGS-19 polypeptide, or a functional peptide or portion thereof (e.g., SEQ ID NOS:2); determining the biological activity of the expressed BGS-19 polypeptide in the absence of a modulator compound; contacting the cell with the modulator compound and determining the biological activity of the expressed BGS-19 polypeptide in the presence of the modulator compound. In such a method, a difference between the activity of the BGS-19 polypeptide in the presence of the modulator compound and in the absence of the modulator compound indicates a modulating effect of the compound.

Essentially any chemical compound can be employed as a potential modulator or ligand in the assays according to the present invention. Compounds tested as potassium channel beta subunit modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel BGS-19 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds polynucleotiderated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for polynucleotiderating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, *Science*, 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a BGS-19 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a BGS-19 polypeptide or peptide to measure a biological binding or ligand binding activity, the source may be a whole cell lysate that can be prepared by successive freeze-thaw cycles (e.g., one to three) in the presence of standard protease inhibitors. The BGS-19 polypeptide may be partially or completely purified by standard protein purification methods, e.g., affinity chromatography using specific antibody described infra, or by ligands specific for an epitope tag engineered into the recombinant BGS-19 polypeptide molecule, also as described herein. Binding activity can then be measured as described.

Compounds which are identified according to the methods provided herein, and which modulate or regulate the biological activity or physiology of the BGS-19 polypeptides according to the present invention are a preferred embodiment of this invention. It is contemplated that such modulatory compounds may be employed in treatment and therapeutic methods for treating a condition that is mediated by the novel BGS-19 polypeptides by administering to an individual in need of such treatment a therapeutically effective amount of the compound identified by the methods described herein.

In addition, the present invention provides methods for treating an individual in need of such treatment for a disease, disorder, or condition that is mediated by the BGS-19 polypeptides of the invention, comprising administering to the individual a therapeutically effective amount of the BGS-19-modulating compound identified by a method provided herein.

The human BGS-19 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a BGS-19 polypeptide, or a bindable peptide fragment, of this invention, comprising providing a plurality of compounds, combining the BGS-19 polypeptide, or a bindable peptide fragment, with each of a plurality of compounds for a time sufficient to allow binding under suitable conditions and detecting binding of the BGS-19 polypeptide or peptide to each of the plurality of test compounds, thereby identifying the compounds that specifically bind to the BGS-19 polypeptide or peptide.

Methods of identifying compounds that modulate the activity of the novel human BGS-19 polypeptides and/or peptides are provided by the present invention and comprise combining a potential or candidate compound or drug modulator of potassium channel beta subunit biological activity with an BGS-19 polypeptide or peptide, for example, the BGS-19 amino acid sequence as set forth in SEQ ID NO:2, and measuring an effect of the candidate compound or drug modulator on the biological activity of the BGS-19 polypeptide or peptide. Such measurable effects include, for example, physical binding interaction; the ability to cleave a suitable potassium channel beta subunit substrate; effects on native and cloned BGS-19-expressing cell line; and effects of modulators or other potassium channel beta subunit-mediated physiological measures.

Another method of identifying compounds that modulate the biological activity of the novel BGS-19 polypeptides of the present invention comprises combining a potential or candidate compound or drug modulator of a potassium channel beta subunit biological activity with a host cell that expresses the BGS-19 polypeptide and measuring an effect of the candidate compound or drug modulator on the biological activity of the BGS-19 polypeptide. The host cell can also be capable of being induced to express the BGS-19 polypeptide, e.g., via inducible expression. Physiological effects of a given modulator candidate on the BGS-19 polypeptide can also be measured. Thus, cellular assays for particular potassium channel beta subunit modulators may be either direct measurement or quantification of the physical biological activity of the BGS-19 polypeptide, or they may be measurement or quantification of a physiological effect. Such methods preferably employ a BGS-19 polypeptide as described herein, or an overexpressed recombinant BGS-19 polypeptide in suitable host cells containing an expression vector as described herein, wherein the BGS-19 polypeptide is expressed, overexpressed, or undergoes upregulated expression.

Another aspect of the present invention embraces a method of screening for a compound that is capable of modulating the biological activity of a BGS-19 polypeptide, comprising providing a host cell containing an expression vector harboring a nucleic acid sequence encoding a BGS-19 polypeptide, or a functional peptide or portion thereof (e.g., SEQ ID NOS:2); determining the biological activity of the expressed BGS-19 polypeptide in the absence of a modulator compound; contacting the cell with the modulator compound and determining the biological activity of the expressed BGS-19 polypeptide in the presence of the modulator compound. In such a method, a difference between the activity of the BGS-19 polypeptide in the presence of the modulator compound and in the absence of the modulator compound indicates a modulating effect of the compound.

Essentially any chemical compound can be employed as a potential modulator or ligand in the assays according to the present invention. Compounds tested as potassium channel beta subunit modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel BGS-19 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds polynucleotiderated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.,* 37:487–493; and Houghton et al., 1991, *Nature,* 354:84–88). Other chemistries for polynucleotiderating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, *Science*, 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a BGS-19 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay

An example of such an assay is the fluorescence based thermal shift assay (3-Dimensional Pharmaceuticals, Inc., 3DP, Exton, Pa.) as described in U.S. Pat. Nos. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a BGS-19 polypeptide or peptide to measure a biological binding or ligand binding activity, the source may be a whole cell lysate that can be prepared by successive freeze-thaw cycles (e.g., one to three) in the presence of standard protease inhibitors. The BGS-19 polypeptide may be partially or completely purified by standard protein purification methods, e.g., affinity chromatography using specific antibody described infra, or by ligands specific for an epitope tag engineered into the recombinant BGS-19 polypeptide molecule, also as described herein. Binding activity can then be measured as described.

Compounds which are identified according to the methods provided herein, and which modulate or regulate the biological activity or physiology of the BGS-19 polypeptides according to the present invention are a preferred embodiment of this invention. It is contemplated that such modulatory compounds may be employed in treatment and therapeutic methods for treating a condition that is mediated by the novel BGS-19 polypeptides by administering to an individual in need of such treatment a therapeutically effective amount of the compound identified by the methods described herein.

In addition, the present invention provides methods for treating an individual in need of such treatment for a disease, disorder, or condition that is mediated by the need of such treatment for a disease, disorder, or condition that is mediated by the BGS-19 polypeptides of the invention, comprising administering to the individual a method provided herein.

Detection Assays

Portions or fragments of the cDNA sequences identified herein (and the corresponding complete polynucleotide sequences) can be used in numerous ways as polynucleotide reagents. For example, these sequences can be used to: (i) map their respective polynucleotides on a chromosome and, thus, locate polynucleotide regions associated with polynucleotidetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a polynucleotide has been isolated, this sequence can be used to map the location of the polynucleotide on a chromosome. Accordingly, BGS-19 polynucleotides described herein or fragments thereof, can be used to map the location of the corresponding polynucleotides on a chromosome. The mapping of the sequences to chromosomes is an important first step in correlating these sequences with chromosomal aberrations associated with BGS-19-related disease.

Briefly, polynucleotides can be mapped to chromosomes by preparing PCR primers (preferably 15–25 bp in length) from the sequence of a polynucleotide of the invention. Computer analysis of the sequence of a polynucleotide of the invention can be used to rapidly select primers that do not span more than one exon in the genomic DNA, thus complicating the amplification process. These primers can then be used for PCR screening of somatic cell hybrids containing individual human chromosomes. Only those hybrids comprising the human polynucleotide corresponding to the polynucleotide sequences will yield an amplified fragment (see, e.g., Eustachio et al., 1983, Science 220: 919–924).

PCR mapping of somatic cell hybrids is a rapid procedure for assigning a particular sequence to a particular chromosome. Three or more sequences can be assigned per day using a single thermal cycler. Using the polynucleotides of the invention to design oligonucleotide primers, sublocalization can be achieved with panels of fragments from specific chromosomes. Other mapping strategies which can similarly be used to map a polynucleotide to its chromosome include in situ hybridization (see, e.g., Fan et al., 1990, Proc Natl Acad Sci. 87:6223–6227), pre-screening with labeled flow-sorted chromosomes ("CITE"), and pre-selection by hybridization to chromosome specific cDNA libraries. Fluorescence in situ hybridization ("FISH") of a DNA sequence to a metaphase chromosomal spread can further be used to provide a precise chromosomal location in one step (see, e.g., Verma et al., *Human Chromosomes: A Manual of Basic Techniques*, Pergamon Press, New York, 1988).

Reagents for chromosome mapping can be used individually to mark a single chromosome or a single site on that chromosome, or panels of reagents can be used for marking multiple sites and/or multiple chromosomes. Reagents corresponding to noncoding regions of the polynucleotides actually are preferred for mapping purposes. Coding sequences are more likely to be conserved within polynucleotide families, thus increasing the chance of cross hybridizations during chromosomal mapping.

Once a sequence has been mapped to a precise chromosomal location, the physical position of the sequence on the chromosome can be correlated with polynucleotidetic map data (see, e.g., V. McKusick, *Mendelian Inheritance in Man*, http://www.ncbi.nlm.nih.gov/Omim/). The relationship between polynucleotides and disease, mapped to the same chromosomal region, can then be identified through linkage analysis or co-inheritance of physically adjacent polynucleotides (see, e.g., Egeland et al., 1987, Nature 325:783–787).

Moreover, differences in the DNA sequences between individuals affected and unaffected with a disease associated with a polynucleotide of the invention can be determined. If a mutation is observed in some or all of the affected individuals but not in any unaffected individuals, then the mutation is likely to be the causative agent of the particular disease. Comparison of affected and unaffected individuals polynucleotiderally involves first looking for structural alterations in the chromosomes such as deletions or translocations that are visible from chromosome spreads or detectable using PCR based on that DNA sequence. Ultimately, complete sequencing of polynucleotides from several individuals can be performed to confirm the presence of a mutation and to distinguish mutations from polymorphisms.

Furthermore, the polynucleotides disclosed herein can be used to perform searches against "mapping databases", e.g., BLAST-type search, such that the chromosome position of the polynucleotide is identified by sequence homology or identity with known sequence fragments which have been mapped to chromosomes.

In addition, a polypeptide and fragments and sequences thereof and antibodies specific thereto can be used to map the location of the polynucleotide encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains (see, e.g., Pajunen et al., 1988, Cytopolynucleotidet Cell Genet. 47:37–41; Van Keuren et al., 1986, Hum Genet. 74:34–40). Alternatively, the presence of the polypeptide in the somatic cell hybrids can be determined by assaying an activity or property of the polypeptide, for example, enzymatic activity, (see, e.g., Bordelon-Riser et al., 1979, Somatic Cell Genetics 5:597–613; Owerbach et al., 1978, Proc Natl Acad Sci. 75:5640–5644).

Tissue Typing

The BGS-19 polynucleotides can also be used to identify individuals from minute biological samples. The United States military, for example, is considering the use of restriction fragment length polymorphism ("RFLP") for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the polynucleotides described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The polynucleotides of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals.

If a panel of reagents from the polynucleotides described herein is used to polynucleotiderate a unique identification database for an individual, those same reagents can later be used to identify tissue from that individual. Using the unique identification database, positive identification of the individual, living or dead, can be made from extremely small tissue samples.

Uses for Forensic Biology

DNA-based identification techniques can also be used in forensic biology. Forensic biology is a scientific field employing polynucleotidetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample. This can be very useful in cases where a forensic pathologist is presented with a tissue of unknown origin. Panels of such probes can be used to identify tissue by species and/or by organ type.

The BGS-19 polynucleotides of the invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme polynucleotiderated fragments. Sequences targeted to non-coding regions are particularly appropriate for this use as greater numbers of polymorphisms occur in the non-coding regions, making it easier to differentiate individuals using this technique. Examples of polynucleotide reagents include the polynucleotides of the invention or portions thereof, e.g., fragments derived from non-coding regions having a length of at least 20 or 30 bases.

Accordingly, the BGS-19 polynucleotides of the invention can be used to provide polynucleotide reagents, e.g., labeled probes that can be used in, for example, to identify a specific cell type or tissue type by in situ hybridization technique.

Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. As such, the present invention contemplates use of the BGS-19 polynucleotides, BGS-19 polypeptides, BGS-19 agonists and/or BGS-19 antagonists of the invention to screen, diagnose, stage, prevent and/or treat disorders characterized by aberrant expression or activity of the BGS-19 polynucleotide and/or polypeptides of the invention. Such disorders include, but are not limited to, cancers, immune related disorders, developmental disorders.

One aspect of the present invention relates to diagnostic assays for determining expression of a polypeptide or polynucleotide of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention, such as a proliferative disorder, e.g., cancer. Accordingly, the present invention provides a method for diagnosing a BGS-19-related disorder, comprising comparing an amount of BGS-19 polynucleotide or BGS-19 polypeptide expressed in a normal tissue to an amount expressed in a diseased tissue.

The invention also provides for prognostic (or predictive) assays for determining whether an individual is at risk of developing a disorder associated with aberrant expression or activity of a polypeptide of the invention. For example, mutations in a polynucleotide of the invention can be assayed in a biological sample. Such assays can be used for prognostic or predictive purpose to thereby prophylactically treat an individual prior to the onset of a disorder characterized by or associated with aberrant expression or activity of a polypeptide of the invention. Accordingly, the present invention provides a method for determining a prognosis of a BGS-19-related disorder, comprising the step of comparing an amount of BGS-19 polynucleotide or BGS-19 polypeptide expressed in a biological sample at a first stage of a disease to an amount of BGS-19 polynucleotide or BGS-19 polypeptide expressed in the sample at a second stage of the disease.

Another aspect of the invention provides methods for expression of a BGS-19 polynucleotide or BGS-19 polypeptide of the invention or activity of a BGS-19 polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the in vivo expression or activity of a BGS-19 polypeptide of the invention. These and other agents are described in further detail in the following sections.

Diagnostic Assays

The present invention provides a method for diagnosing a BGS-19-related disorder, comprising comparing an amount of BGS-19 polynucleotide or BGS-19 polypeptide expressed in a normal tissue to an amount expressed in a diseased tissue. An exemplary method for detecting the presence or absence of a BGS-19 polypeptide or BGS-19 polynucleotide of the invention in a biological sample involves obtaining a biological sample from a test subject and contacting the biological sample with a compound or an agent capable of detecting a BGS-19 polypeptide or polynucleotide (e.g., mRNA, genomic DNA) of the invention such that the presence of a polypeptide or polynucleotide of the invention is detected in the biological sample.

In a specific embodiment, the invention provides a method for diagnosing a BGS-19-related disorder in a subject comprising the steps of contacting a BGS-19 antibody with a sample, suspected of containing a BGS-19 polypeptide, from said subject under conditions that allow the BGS-19 polypeptide to be bound by the BGS-19 antibody and detecting or measuring binding of the BGS-19 antibody to the BGS-19 polypeptide, wherein detection or measurement of binding indicates presence or amount, respectively, of the BGS-19 polypeptide, and wherein the BGS-19-related disorder is determined to be present when the presence or amount of detected BGS-19 polypeptide differs from a control value representing the amount of BGS-19 polypeptide present in an analogous sample from a subject not having the BGS-19-related disorder.

A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as that presented in FIGS. 1A–C or a portion thereof, such as an oligonucleotide of at least 15, 30, 50, 100, 250 or 500 contiguous nucleotides in length and sufficient to specifically hybridize under stringent conditions to a mRNA or genomic DNA encoding a polypeptide of the invention, excluding a polynucleotide consisting of Genbank Accession Nos. gi|BI518708, gi|BF308356, gi|BF205116, gi|BF969219, gi|BG826221, and/or gi|AA341128. Other suitable probes for use in the diagnostic assays of the invention are described herein.

A preferred agent for detecting a BGS-19 polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The detection methods of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assay (ELISA), Western blotting, immunoprecipitation and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample comprises protein molecules from the test subject. Alternatively, the biological sample can comprise mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a BGS-19 polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

Probes based on the sequence of a BGS-19 polynucleotide of the invention can be used to detect transcripts or genomic sequences encoding the same protein molecule encoded by a selected polynucleotide. The probe comprises a label group attached thereto, e.g., a radioisotope, a fluorescent compound, an enzyme, or an enzyme co-factor. Such probes can be used as part of a diagnostic test kit for examining protein expression in cells or tissues, such as by measuring levels of a polynucleotide encoding the protein in a sample of cells from a subject, e.g., detecting mRNA levels or determining whether a polynucleotide encoding the protein has been mutated or deleted.

Antibodies directed against wild-type or mutant BGS-19 polynucleotides or polypeptides, or conserved variants or peptide fragments thereof, may also be used as diagnostics and prognostics, as described herein. Such diagnostic methods, may be used to detect abnormalities in the level of BGS-19 polynucleotide expression, or abnormalities in the structure and/or temporal, tissue, cellular, or subcellular location of BGS-19 polynucleotide product. Antibodies, or fragments of antibodies, such as those described below, may be used to screen potentially therapeutic compounds in vitro to determine their effects on BGS-19 polynucleotide expression and BGS-19 peptide production. The compounds which have beneficial effects on cancer can be identified and a therapeutically effective dose determined.

The tissue or cell type to be analyzed will polynucleotiderally include those which are known, or suspected, to express the BGS-19 polynucleotide such as, for example, bone marrow, brain, heart, kidney, liver, lung, lymph node, pancreas, prostate, small intestine, spinal cord, spleen, stomach, thymus and uterus. Many protein isolation methods are well known in the art (see, e.g., Harlow and Lane, 1988, *Antibodies: A Laboratory Manual*, Cold Spring Harbor Laboratory Press, Cold Spring Harbor, N.Y., which is incorporated herein by reference in its entirety). The isolated cells can be derived from cell culture or from a patient. The analysis of cells taken from culture may be a necessary step to test the effect of compounds on the expression of the BGS-19 polynucleotide.

Preferred diagnostic methods for the detection of BGS-19 polynucleotide products or conserved variants or peptide fragments thereof, may involve, for example, immunoassays wherein the BGS-19 polynucleotide products or conserved variants, including polynucleotide products which are the result of alternatively spliced transcripts, or peptide fragments are detected by their interaction with an anti-BGS-19 polynucleotide product-specific antibody.

For example, antibodies, or fragments of antibodies, useful in the present invention may be used to quantitatively or qualitatively detect the presence of BGS-19 polynucleotide products or conserved variants or peptide fragments thereof. The antibodies (or fragments thereof) useful in the present invention may, additionally, be employed histologically, as in immunofluorescence or immunoelectron microscopy, for in situ detection of BGS-19 polynucleotide products or conserved variants or peptide fragments thereof. In situ detection may be accomplished by removing a histological specimen from a patient, such as paraffin embedded sections of lymphoid tissues and applying thereto a labeled antibody of the present invention. The antibody (or fragment) is preferably applied by overlaying the labeled antibody (or fragment) onto a biological sample. When a BGS-19 polynucleotide product is present in the cytoplasm, the antibody of the invention can be introduced inside the cell, for example, by making the cell membrane permeable. Through the use of such a procedure, it is possible to determine not only the presence of a BGS-19 polynucleotide product, or conserved variants or peptide fragments, but also the distribution of a BGS-19 in a cell, tissue, or organ of interest. Using the present invention, those of ordinary skill will readily perceive that any of a wide variety of histological methods (such as staining procedures) can be modified in order to achieve such in situ detection.

Immunoassays for BGS-19 polynucleotide products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying BGS-19 polynucleotide products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled BGS-19 polynucleotide specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-BGS-19 polynucleotide product antibody may be determined according to standard methods. Those skilled in the art will be able to determine operative and optimal assay conditions for each determination by using standard techniques.

One of the ways in which the BGS-19 polynucleotide peptide-specific antibody can be detectably labeled is by linking the same to an enzyme and use in an enzyme immunoassay (Voller, 1978, "The Enzyme Linked Immunosorbent Assay (ELISA)", 1978, Diagnostic Horizons 2:1–7, Microbiological Associates Quarterly Publication, Walkersville, Md.); Voller et al., 1978, J Clin Pathol. 31:507–520; Butler, 1981, Meth Enzymol. 73:482–523; Maggio, *Enzyme Immunoassay*, CRC Press, Boca Raton, Fla., 1980; Ishikawa et al., *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect BGS-19 peptides through the use of a radioimmunoassay ("RIA") (See, e.g., B. Weintraub, *Principles of Radioimmunoassays, Seventh Training Course on Radioligand Assay Techniques*, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid ("DTPA") or ethylenediaminetetraacetic acid ("EDTA").

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Any of numerous immunoassays can be used in the practice of the instant invention. Antibodies, or antibody fragments comprising the binding domain, are known in the art or can be obtained by procedures standard in the art such as those described in Harlow and Lane, *Antibodies: A Laboratory Manual*, Cold Spring Harbor Laboratory, 1988.

Detecting and Staging Cancer in a Patient

Cancer can be detected and staged in a patient using a BGS-19 polynucleotide and polypeptide of the invention. In one embodiment of the present invention, measurement of at least one BGS-19 polynucleotide products or fragments thereof, or soluble BGS-19 polynucleotide products can be used to detect cancer in a subject or to stage the cancer in a subject.

Staging refers to the grouping of patients according to the extent of their disease. Staging is useful in choosing treatment for individual patients, estimating prognosis, and comparing the results of different treatment programs. Staging of cancer is performed initially on a clinical basis, according to the physical examination and laboratory radiologic evaluation. The most widely used clinical staging system is the one adopted by the International Union against Cancer (UICC) and the American Joint Committee on Cancer (AJCC) Staging and End Results Reporting. It is based on the tumor-nodes-metastases (TNM) system as detailed in the 1988 *Manual for Staging of Cancer*.

Accordingly, in an exemplary embodiment, the invention provides a method for staging a disease in a subject comprising the steps of contacting a BGS-19 binding protein with a sample, suspected of containing a BGS-19 polypeptide, from the subject under conditions that allow the BGS-19 polypeptide to be bound by the BGS-19 binding protein and detecting or measuring binding of the BGS-19 binding protein to the BGS-19 polypeptide, wherein detection or measurement of binding indicates presence or amount, respectively, of the BGS-19 polypeptide, and wherein the stage of the disease is determined when the presence or amount of detected BGS-19 polypeptide is compared with the amount of BGS-19 polypeptide present in an analogous sample from a subject having a particular stage of the disease. In a further embodiment, the disease is a BGS-19-related disorder.

In another embodiment, the invention provides a method for staging a BGS-19-related disorder in a subject comprising the steps of contacting a BGS-19 antibody with a sample, suspected of containing a BGS-19 polypeptide, from the subject under conditions that allow the BGS-19 polypeptide to be bound by the BGS-19 antibody and detecting or measuring binding of the BGS-19 antibody to the BGS-19 polypeptide, wherein detection or measurement of binding indicates presence or amount, respectively, of the BGS-19 polypeptide, and wherein the stage of the BGS-19-related disorder in the subject is determined when the presence or amount of detected BGS-19 polypeptide is compared with the amount of BGS-19 polypeptide present in an analogous sample from a subject having a particular stage of the BGS-19-related disorder.

Prognostic Assays

The methods described herein can furthermore be utilized as prognostic assays to identify subjects having or at risk of developing a disease or disorder associated with aberrant expression or activity of a BGS-19 polypeptide of the invention. For example, the assays described herein, such as the preceding diagnostic assays or the following assays, can be utilized to identify a subject having or at risk of developing a disorder associated with aberrant expression or activity of a BGS-19 polypeptide of the invention, e.g., an immunologic disorder, or proliferative disorders.

Alternatively, the prognostic assays can be utilized to identify a subject having or at risk for developing such a disease or disorder. Thus, the present invention provides a method in which a test sample is obtained from a subject and a BGS-19 polypeptide or polynucleotide (e.g., mRNA, genomic DNA) of the invention is detected, wherein the presence of the polypeptide or polynucleotide is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

The prognostic assays described herein, for example, can be used to identify a subject having or at risk of developing disorders such as cancers. In another example, prognostic assays described herein can be used to identify a subject having or at risk of developing related disorders associated with expression of polypeptides of the invention.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or polynucleotide encoding the polypeptide is detected (e.g., wherein the presence of the polypeptide or polynucleotide is diagnostic for a subject that can be administered the agent to treat a disorder associated with aberrant expression or activity of the polypeptide).

The methods of the invention can also be used to detect polynucleotidetic lesions or mutations in a BGsS19 polynucleotide of the invention, thereby determining if a subject with the lesioned polynucleotide is at risk for a disorder characterized by aberrant expression or activity of a polypeptide of the invention. In preferred embodiments, the methods include detecting, in a sample of cells from the subject, the presence or absence of a polynucleotidetic lesion or mutation characterized by at least one of an alteration affecting the integrity of a polynucleotide encoding the polypeptide of the invention, or the mis-expression of the polynucleotide encoding the polypeptide of the invention. For example, such polynucleotidetic lesions or mutations can be detected by ascertaining the existence of at least one of: 1) a deletion of one or more nucleotides from the BGS-19 polynucleotide; 2) an addition of one or more nucleotides to the BGS-19 polynucleotide; 3) a substitution of one or more nucleotides of the BGS-19 polynucleotide; 4) a chromosomal rearrangement of the BGS-19 polynucleotide; 5) an alteration in the level of a messenger RNA transcript of the BGS-19 polynucleotide; 6) an aberrant modification of the BGS-19 polynucleotide, such as of the methylation pattern of the genomic DNA; 7) the presence of a non-wild type splicing pattern of a messenger RNA transcript of the BGS-19 polynucleotide; 8) a non-wild type level of the protein encoded by the BGS-19 polynucleotide; 9) an allelic loss of a the BGS-19 polynucleotide; and 10) an inappropriate post-translational modification of the protein encoded by the BGS-19 polynucleotide. As described herein, there are a large number of assay techniques known in the art which can be used for detecting lesions in a polynucleotide.

In certain embodiments, detection of the lesion involves the use of a probe/primer in a polymerase chain reaction ("PCR") (See, e.g., U.S. Pat. Nos. 4,683,195 and 4,683,202), such as anchor PCR or RACE PCR, or, alternatively, in a ligation chain reaction (see, e.g., Landegran et al., 1988, Science 241:1077–1080; Nakazawa et al., 1994, Proc Natl Acad Sci. 91:360–364), the latter of which can be particularly useful for detecting point mutations in a polynucleotide (See, e.g., Abravaya et al., 1995, Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected polynucleotide under conditions such that hybridization and amplification of the polynucleotide (if present) occurs, and detecting the presence or absence of an amplification product, or detecting the size of the amplification product and comparing the length to a control sample. It is anticipated that PCR and/or ligation chain reaction can be useful as a preliminary amplification step in conjunction with any of the techniques used for detecting mutations described herein.

Alternative amplification methods include self sustained sequence replication (Guatelli et al.,1990, Proc Natl Acad Sci. 87:1874–1878), transcriptional amplification system (Kwoh et al., 1989, Proc Natl Acad Sci. 86:1173–1177), Q-Beta Replicase (Lizardi et al., 1988, Biotechnology 6:1197), or any other nucleic acid amplification method, followed by the detection of the amplified molecules using techniques well known to those of skill in the art. These detection schemes are especially useful for the detection of polynucleotides if such molecules are present in very low numbers.

In an alternative embodiment, mutations in a selected polynucleotide from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, polynucleotidetic mutations can be identified by hybridizing a sample and control nucleic acids, e.g., DNA or RNA, to high-density arrays comprising hundreds or thousands of oligonucleotides probes (Cronin et al., 1996, Human Mutation 7:244–255; Kozal et al., 1996, Nature Medicine 2:753–759). For example, polynucleotidetic mutations can be identified in two-dimensional arrays containing light-polynucleotiderated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type polynucleotide and the other complementary to the mutant polynucleotide.

In yet another embodiment, any of a variety of sequencing reactions known in the art can be used to directly sequence the selected polynucleotide and detect mutations by comparing the sequence of the sample nucleic acids with the corresponding wild-type (control) sequence (see, e.g., Maxim and Gilbert, 1977, Proc Natl Acad Sci. 74:560; Sanger, 1977, Proc Natl Acad Sci. 74:5463). It is also contemplated that any of a variety of automated sequencing procedures can be utilized when performing the diagnostic assays, including sequencing by mass spectrometry (see, e.g., PCT Publication No. WO 94/16101; Cohen et al., 1996 Adv Chromatogr. 36:127–162; Naeve et al., 1995, "Accuracy of automated DNA sequencing: a multi-laboratory comparison of sequencing results", Biotechniques. 19:448–453; Griffin et al., 1993, Appl Biochem Biotechnol. 38:147–159).

Other methods for detecting mutations in a selected polynucleotide include methods in which protection from cleavage agents is used to detect mismatched bases in RNA/RNA or RNA/DNA heteroduplexes (Myers et al., 1985, Science 230:1242). In polynucleotideral, the technique of "mismatch cleavage" entails providing heteroduplexes formed by hybridizing (labeled) RNA or DNA comprising the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation (see, e.g., Cotton et al., 1988, Proc Natl Acad Sci. 85:4397; Saleeba et al., 1992, Methods Enzymol. 217:286–295). In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of E. coli cleaves A at G/A mismatches and the thymidine DNA glycosylase from HeLa cells cleaves T at G/T mismatches (Hsu et al., 1994, Carcinopolynucleotidesis 15:1657–1662). Accordingly, in one embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like (see, e.g., U.S. Pat. No. 5,459,039).

In other embodiments, alterations in electrophoretic mobility will be used to identify mutations in polynucleotides. For example, single strand conformation polymorphism may be used to detect differences in electrophoretic mobility between mutant and wild type nucleic acids (see, e.g., Orita et al., 1989, Proc Natl Acad Sci. 86:2766; Cotton, 1993, Mutat Res. 285:125–144; Hayashi, 1992, Genet Anal Tech Appl. 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., 1991, Trends Genet. 7:5).

In yet another embodiment, the movement of mutant or wild-type fragments in polyacrylamide gels containing a gradient of denaturant is assayed using denaturing gradient gel electrophoresis (Myers et al., 1985, Nature 313:495). When denaturing gradient gel electrophoresis is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, 1987, Biophys Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al., 1986, Nature 324:163); Saiki et al., 1989, Proc Natl Acad Sci. 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., 1989, Nucleic Acids Res. 17:2437–2448) or at the extreme 3' end of one primer where, under appropriate conditions, mismatch can prevent or reduce polymerase extension (Prossner, 1993, Tibtech 11:238). In addition, it may be desirable to introduce a novel restriction site in the region of the mutation to create cleavage-based detection (Gasparini et al., 1992, Mol. Cell Probes 6:1). It is anticipated that in certain embodiments amplification may also be performed using Taq ligase for amplification (Barany, 1991, Proc Natl Acad Sci. 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one polynucleotide probe or antibody reagent described herein, which may be conveniently used, e.g., in clinical settings to diagnose patients exhibiting symptoms or family history of a disease or illness involving a polynucleotide encoding a polypeptide of the invention. Furthermore, any cell type or tissue, e.g., preferably peripheral blood leukocytes, in which the polypeptide of the invention is expressed may be utilized in the prognostic assays described herein.

Pharmacogenomics

Pharmacogenomics relates to clinically significant hereditary variations in the response to drugs due to altered drug disposition and abnormal action in affected persons (see, e.g., Linder, 1997, Clin Chem. 43:254–266. In polynucleotideral, two types of pharmacopolynucleotidetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacopolynucleotidetic conditions can occur either as rare defects or as polymorphisms.

Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a BGS-19 polypeptide of the invention, expression of a BGS-19 polynucleotide of the invention, or mutation content of the BGS-19 polynucleotide of the invention in an individual can be determined to thereby select appropriate agent(s) for therapeutic or prophylactic treatment of the individual.

Accordingly, in addition to the nucleotide sequence presented, it will be appreciated by those skilled in the art that DNA sequence polymorphisms that lead to changes in the amino acid sequence may exist within a population (e.g., the human population). Such polynucleotidetic polymorphisms may exist among individuals within a population due to natural allelic variation. An allele is one of a group of polynucleotides which occur alternatively at a given polynucleotidetic locus. As used herein, the phrase "allelic variant" refers to a nucleotide sequence which occurs at a given locus or to a polypeptide encoded by the nucleotide sequence. Such natural allelic variations can typically result in 1–5% variance in the nucleotide sequence of a given polynucleotide. Alternative alleles can be identified by sequencing the polynucleotide of interest in a number of different individuals or by using hybridization probes to identify the same polynucleotidetic locus in a variety of individuals. Any and all such nucleotide variations and resulting amino acid polymorphisms or variations that are the result of natural allelic variation and that do not alter the functional activity are intended to be within the scope of the invention.

Prophylactic Methods

The present invention provides for prophylactic and therapeutic methods of treating a subject at risk of or having the BGS-19-related disorder. Such the BGS-19-related disorder includes, but is not limited to, immune related disorders, developmental disorders, autoimmune disease, and cancer.

Accordingly, the present invention provides for prophylactic and therapeutic methods of treating a subject at risk of (or susceptible to) a disorder or having a disorder associated with aberrant expression or activity of the BGS-19 polypeptide of the invention. For example, disorders characterized by aberrant expression or activity of the polypeptides.

In one aspect, the invention provides a method for preventing in a subject, a disease or condition associated with an aberrant expression or activity of the BGS-19 polypeptide of the invention, by administering to the subject an agent which modulates expression of at least one activity of the BGS-19 polypeptide. Subjects at risk for a disease which is caused or contributed to by aberrant expression or activity of the BGS-19 polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject.

The prophylactic agents described herein can be used to treat a subject at risk of developing a BGS-19-related disorder. The appropriate prophylactic agent can be determined based on screening assays described herein.

Methods of Treatment

The present invention provides for methods for the prevention and/or treatment of a BGS-19-related disorder comprising administering to a patient in need thereof a BGS-19 polynucleotide, BGS-19 polypeptide, BGS-19 agonist, BGS-19 antagonist, or an inhibitor of a BGS-19 agonist or antagonist.

More particularly, the present invention relates to uses of BGS-19 polynucleotides, polypeptides, and BGS-19 antagonists for the prevention, diagnosis, prognosis and management of immune related disorders and cancer. The invention contemplates uses of BGS-19 polynucleotides, polypeptides, and BGS-19 antagonists (e.g., antibodies directed against BGS-19 polypeptides of the invention) to treat such diseases.

The invention pertains to methods of modulating BGS-19 expression or activity of a BGS-19 polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecules. In one embodiment, the agent stimulates one or more of the biological activities of the polypeptide. Examples of such stimulatory agents include the active polypeptide of the invention and a polynucleotide encoding the polypeptide of the invention that has been introduced into the cell.

In another embodiment, the agent inhibits one or more of the biological activities of the polypeptide of the invention. Examples of such inhibitory agents include antisense polynucleotides and antibodies. These modulatory methods can be performed in vitro (e.g., by culturing the cell with the agent) or, alternatively, in vivo (e.g., by administering the agent to a subject or in the vicinity of the cells). As such, the present invention provides methods of treating an individual afflicted with a disease or disorder characterized by aberrant expression or activity of a BGS-19 polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a BGS-19 polypeptide of the invention or a polynucleotide of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

Cancers and Therapeutics

BGS-19 polynucleotides, BGS-19 polypeptides, BGS-19 agonists, BGS-19 antagonists, inhibitors of such agonists or antagonists, and variants thereof, can be used to modulate the development and progression of non-cancerous cell-proliferative disorders such as, but not limited to, deregulated proliferation (e.g., hyperdysplasia, hyper-IgM syndrome, or lymphoproliferative disorders), cirrhosis of the liver (a condition in which scarring has overtaken normal liver repolynucleotideration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, tissue hypertrophy (e.g., prostatic hyperplasia), ovarian cancer or proliferative ovarian disorder.

BGS-19 polynucleotides, BGS-19 polypeptides, BGS-19 agonists, BGS-19 antagonists, inhibitors of such agonists or antagonists, and variants thereof, can also be used to modulate the development and progression of cancers such as, but not limited to, neoplasms, tumors, carcinomas, sarcomas, adenomas or myeloid lymphoma tumors, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon sarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hematoma, bile duct carcinoma, melanoma, choriocarcinoma, semicoma, embryonal carcinoma, Wilms' tumor, cervical cancer, testicular tumor, lung carcinoma, small cell carcinoma, bladder carcinoma, epithelial carcinoma, glioma, astrocytoma, medulloblastoma, craniopharyngioma, ependynoma, pinealoma, hemangioblastoma, retinoblastoma), leukemias, (e.g. acute lymphocytic leukemia), acute myelocytic leukemia (myelolastic, promyelocytic, myelomonocytic, monocytic and erythroleukemia), chronic leukemias (chronic myelocytic (granulocytic) leukemia and chronic lymphocytic leukemia), or polycythemia vera, or lymphomas (Hodgkin's disease and non-Hodgkin's diseases), multiple myelomas and Waldenstrom's macroglobulinemia. In particular, the BGS-19 polynucleotides, polypeptides, and modulators thereof, can be used to modulate the development and progression of hormone-sensitive cancers, such as but not limited to cancer of the breast, ovary, uterus, prostate, testis, skin and brain.

Antisense Therapy

The present invention provides compositions and methods for the use of a BGS-19 antisense oligonucleotide to prevent or treat a BGS-19-related disorder, such as cancer. The invention also provides pharmaceutical compositions comprising a BGS-19 antisense oligonucleotide, as well as methods for their prophylactic and therapeutic use. An antisense oligonucleotide, or an analogue or derivative thereof, refers to a range of chemical species that recognize polynucleotide target sequences through Watson-and-Crick hydrogen bonding interactions with the nucleotide bases of the target sequences. The target sequences may be RNA or DNA, and may be single-stranded or double-stranded. Target molecules include, but are not limited to, pre-mRNA, mRNA, and DNA. Also encompassed by the invention are drug delivery means and therapeutic regimens for the pharmaceutical compositions of the invention.

In one embodiment, a BGS-19 antisense oligonucleotide is administered to a human to prevent or treat a BGS-19 related disorder, wherein BGS-19 mRNA or protein is expressed at above-normal levels.

In another embodiment, a BGS-19 antisense oligonucleotide is administered to a human at a high dose to prevent or treat a BGS-19 related disorder.

In another embodiment, a BGS-19 antisense oligonucleotide is administered to a human at a low or reduced dose to prevent or treat a BGS-19 related disorder.

Aside from affecting diseased tissue, a BGS-19 antisense oligonucleotide can affect normal tissues, which include tissues containing cells that normally express a BGS-19 polynucleotide. Additionally, a BGS-19 antisense oligonucleotide can affect normal tissues that, although not expressing a BGS-19 polynucleotide, are compromised by diseased tissues. In a particular embodiment, a BGS-19 antisense oligonucleotide can protect normal tissues that do or do not normally express a BGS-19 polynucleotide.

In a specific embodiment, the invention provides for a BGS-19 antisense oligonucleotide that is administered to a human, in combination with one of more additional therapeutic agents. In a further embodiment, the additional therapeutic agent is a second, different antisense oligonucleotide. In another further embodiment, the additional therapeutic agent is a chemotherapeutic agent.

Antibody Therapy

The present invention provides for methods for preventing or treating a BGS-19 related disorder comprising administering to a patient in need thereof, an antibody that can bind a BGS-19 polypeptide.

Accordingly, by following procedures well known in the art for developing antibodies useful in clinical settings, an antibody directed to a BGS-19 polypeptide can be used for antibody therapy. Depending on the disease to be treated, a dose of approximately 1 µg/kg to 20 mg/kg of a composition comprising an antibody of the present invention is administered to the patient. In one embodiment, the dose of antibody is 1 µg/kg to 100 µg/kg. In another embodiment, the dose of antibody is 101 µg/kg to 999 µg/kg. In another embodiment, the dose of antibody is 1 mg/kg to 5 mg/kg. In yet another embodiment, the dose of antibody is 6 mg/kg to 10 mg/kg. In yet another embodiment, the dose of antibody is 11 mg/kg to 20 mg/kg. The progress of an antibody therapy can be monitored using standard techniques and assays (See, e.g., International Patent Publication No. WO 94/04188).

Small Molecule Therapy

The present invention also encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. The factors to consider in choosing an appropriate dose of a small molecule agent will be understood by the ordinarily skilled physician, veterinarian, or scientist. The dose(s) of the small molecule will vary, for example, depending upon the identity, size, and condition of the subject or sample being treated, further depending upon the route by which the composition is to be administered, if applicable, and the effect which the practitioner desires the small molecule to have upon the polynucleotide or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or polynucleotide of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, polynucleotideral health, gender, and diet of the subject, the time of administration, the route of administration, the rate of excretion, any drug combination, and the degree of expression or activity to be modulated.

The human BGS-19 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a BGS-19 polypeptide, or a bindable peptide fragment, of this invention, comprising providing a plurality of compounds, combining the BGS-19 polypeptide, or a bindable peptide fragment, with each of a plurality of compounds for a time sufficient to allow binding under suitable conditions and detecting binding of the BGS-19 polypeptide or peptide to each of the plurality of test compounds, thereby identifying the compounds that specifically bind to the BGS-19 polypeptide or peptide.

Methods of identifying compounds that modulate the activity of the novel human BGS-19 polypeptides and/or peptides are provided by the present invention and comprise combining a potential or candidate compound or drug modulator of immunoglobulin domain containing polypeptide biological activity with an BGS-19 polypeptide or peptide, for example, the BGS-19 amino acid sequence as set forth in SEQ ID NO:2, and measuring an effect of the candidate compound or drug modulator on the biological activity of the BGS-19 polypeptide or peptide. Such measurable effects include, for example, physical binding interaction; the ability to cleave a suitable immunoglobulin domain containing polypeptide substrate; effects on native and cloned BGS-19-expressing cell line; and effects of modulators or other immunoglobulin domain containing polypeptide-mediated physiological measures.

Another method of identifying compounds that modulate the biological activity of the novel BGS-19 polypeptides of the present invention comprises combining a potential or candidate compound or drug modulator of a immunoglobulin domain containing polypeptide biological activity with a host cell that expresses the BGS-19 polypeptide and measuring an effect of the candidate compound or drug modulator on the biological activity of the BGS-19 polypeptide. The host cell can also be capable of being induced to express the BGS-19 polypeptide, e.g., via inducible expression. Physiological effects of a given modulator candidate on the BGS-19 polypeptide can also be measured. Thus, cellular assays for particular immunoglobulin domain containing polypeptide modulators may be either direct measurement or quantification of the physical biological activity of the BGS-19 polypeptide, or they may be measurement or quantification of a physiological effect. Such methods preferably employ a BGS-19 polypeptide as described herein, or an overexpressed recombinant BGS-19 polypeptide in suitable host cells containing an expression vector as described herein, wherein the BGS-19 polypeptide is expressed, overexpressed, or undergoes upregulated expression.

Another aspect of the present invention embraces a method of screening for a compound that is capable of modulating the biological activity of a BGS-19 polypeptide, comprising providing a host cell containing an expression vector harboring a nucleic acid sequence encoding a BGS-19 polypeptide, or a functional peptide or portion thereof (e.g., SEQ ID NOS:2); determining the biological activity of the expressed BGS-19 polypeptide in the absence of a modulator compound; contacting the cell with the modulator compound and determining the biological activity of the expressed BGS-19 polypeptide in the presence of the modulator compound. In such a method, a difference between the activity of the BGS-19 polypeptide in the presence of the modulator compound and in the absence of the modulator compound indicates a modulating effect of the compound.

Essentially any chemical compound can be employed as a potential modulator or ligand in the assays according to the present invention. Compounds tested as immunoglobulin domain containing polypeptide modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel BGS-19 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.,* 37:487–493; and Houghton et al., 1991, *Nature,* 354:84–88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA,* 90:6909–6913), vinylogous polypeptides (Hagihara et al., 1992, *J. Amer. Chem. Soc.,* 114:6568), nonpeptidal peptidomimetics with glucose scaffolding (Hirschmann et al., 1992, *J. Amer. Chem. Soc.,* 114:9217–9218), analogous organic synthesis of small compound libraries (Chen et al., 1994, *J. Amer. Chem. Soc.,* 116:2661), oligocarbamates (Cho et al., 1993, *Science,* 261:1303), and/or peptidyl phosphonates (Campbell et al., 1994, *J. Org. Chem.,* 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology,* 14(3):309–314) and PCT/US96/10287), carbohydrate libraries (e.g., Liang et al., 1996, *Science,* 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a BGS-19 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a BGS-19 polypeptide or peptide to measure a biological binding or ligand binding activity, the source may be a whole cell lysate that can be prepared by successive freeze-thaw cycles (e.g., one to three) in the presence of standard protease inhibitors. The BGS-19 polypeptide may be partially or completely purified by standard protein purification methods, e.g., affinity chromatography using specific antibody described infra, or by ligands specific for an epitope tag engineered into the recombinant BGS-19 polypeptide molecule, also as described herein. Binding activity can then be measured as described.

Compounds which are identified according to the methods provided herein, and which modulate or regulate the biological activity or physiology of the BGS-19 polypeptides according to the present invention are a preferred embodiment of this invention. It is contemplated that such modulatory compounds may be employed in treatment and therapeutic methods for treating a condition that is mediated by the novel BGS-19 polypeptides by administering to an individual in need of such treatment a therapeutically effective amount of the compound identified by the methods described herein.

In addition, the present invention provides methods for treating an individual in need of such treatment for a disease, disorder, or condition that is mediated by the BGS-19 polypeptides of the invention, comprising administering to the individual a therapeutically effective amount of the BGS-19-modulating compound identified by a method provided herein.

Gene Therapy

Gene therapy approaches may also be used in accordance with the present invention to modulate the expression of a BGS-19 polynucleotide. Gene therapy refers to therapy performed by the administration to a subject of an expressed or expressible polynucleotide. Accordingly, the present invention provides for a method for treating or preventing a BGS-19-related disorder comprising administering to a patient in need thereof an effective amount of a mammalian expression vector comprising a BGS-19 polynucleotide or a polynucleotide encoding a BGS-19 polypeptide, BGS-19 agonist, BGS-19 antagonist, inhibitor of a BGS-19 agonist, inhibitor of a BGS-19 antagonist, or a variant thereof.

Any of the methods for polynucleotide therapy available in the art can be used in accordance with the present invention (See, e.g., Goldspiel et al., 1993, Clinical Pharmacy 12:488–505; Grossman and Wilson, 1993, Curr Opin Genet Devel. 3:110–114; Salmons and Gunzberg, 1993, Human Gene Therapy 4:129–141; Morgan and Anderson, 1993, Ann Rev Biochem. 62:191–217; Mulligan, 1993, Science 260:926–932; Tolstoshev, 1993, Ann Rev Pharmacol Toxicol. 32:573–596; Clowes et al., 1994, J Clin Invest. 93:644–651; Kiem et al., 1994, Blood 83:1467–1473, each of which is incorporated herein by reference). Gene therapy vectors can be administered to a subject systemically or locally by, for example, intravenous injection (See, e.g., U.S. Pat. No. 5,328,470) or by stereotactic injection (See, e.g., Chen et al., 1994, Proc Natl Acad Sci. 91:3054–57). Synthetic polynucleotides, the in vitro or in vivo transcription and translation of which results in the production of a BGS-19 antagonist, for example, may be constructed by techniques well known in the art. For example, antisense, ribozyme, triple helix molecules, and/or recombinant antibodies may be used to target by polynucleotide therapy a BGS-19 polynucleotide of the invention, resulting in a decrease in the respective BGS-19 polynucleotide expression and/or BGS-19 protein levels. Techniques for the production and use of antisense, ribozyme, and/or triple helix molecules are well known to those of skill in the art, and in accordance with the present invention, can be applied to a nucleotide sequence encoding a BGS-19 polypeptide of the invention.

A pharmaceutical preparation of the polynucleotide therapy vector can comprise a polynucleotide therapy vector in an acceptable diluent, or can comprise a slow release matrix in which the polynucleotide delivery vehicle is embedded. Alternatively, where the complete polynucleotide delivery vector can be produced intact from recombinant cells, e.g., retroviral vectors, the pharmaceutical preparation can include one or more cells which produce the polynucleotide delivery system.

The present invention encompasses vectors comprising a polynucleotide encoding a BGS-19 polypeptide of the invention, or the complement thereof. In one embodiment, a BGS-19 polynucleotide of the invention to be introduced for purposes of polynucleotide therapy comprises an inducible promoter operably linked to the coding region in the antisense orientation, such that expression of the polynucleotide can be controlled using an appropriate inducer or inhibitor of transcription. In another embodiment, the vector comprises a promoter which expresses the cloned construct constitutively. In a further embodiment, the promoter can be downregulated by a suppressor molecule. Alternatively, the vector comprises a promoter, such that an inducing molecule initiates or increases expression of the cloned antisense BGS-19 polynucleotide. In a preferred embodiment, the vector comprises a cell-specific promoter. In another preferred embodiment, the vector comprises a disease-specific promoter, such that expression is largely limited to diseased tissues or tissues surrounding diseased tissues. In another particular embodiment, a BGS-19 antisense oligonucleotide is placed within a mammalian expression vector such that a BGS-19 antisense construct comprises the entire cDNA sequence.

Gene therapy involves introducing a polynucleotide construct to cells in tissue culture or in vivo. Methods for introduction of polynucleotides of the invention to cells in vitro include, but are not limited to, electroporation, lipofection, calcium phosphate-mediated transfection, and viral infection. Usually, the method of transfer includes the transfer of a selectable marker to the cells, after which the cells are placed under selection to isolate the cells which have taken up and express the transferred polynucleotide. The transfected cells then can be administered to a subject.

An expression construct can be delivered directly into a subject. In one embodiment, the polynucleotides of the invention can be injected directly into the target tissue or cell derivation site. Alternatively, a subject's cells are first transfected with an expression construct in vitro, after which the transfected cells are administered back into the subject (i.e., ex vivo polynucleotide therapy). Accordingly, the polynucleotides of the invention can be delivered in vivo or ex vivo to target cells. Several methods have been developed for delivering the polynucleotides of the invention to target cells or target tissues.

Another approach to polynucleotide therapy involves transferring a polynucleotide to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred polynucleotide. Those cells are then delivered to a subject. In another embodiment, the polynucleotides of the invention can be introduced into the target tissue as an implant, for example, in a polymer formulation (See, e.g., U.S. Pat. No. 5,702,717). In another embodiment, the polynucleotides of the invention can be targeted to the desired cells or tissues.

In one embodiment, a polynucleotide of the invention is administered to inhibit BGS-19 activity using polynucleotide therapy.

In a particular embodiment, a vector is introduced in vivo such that it is taken up by a cell and directs the transcription of an antisense BGS-19 polynucleotide of the invention. Such a vector can remain episomal or can become chromosomally integrate. Expression vectors can be plasmid, viral, or others known in the art, that can be used to replicate and/or express the cloned nucleotide sequence encoding a BGS-19 antisense polynucleotide in a target mammalian cell. A variety of expression vectors useful for introducing into cells the polynucleotides of the inventions are well known in the art (See, e.g., Promega™ catalogue, 2001; Stratapolynucleotide™ catalogue, 2001). Expression constructs can be introduced into target cells and/or tissues of a subject using vectors which include, but are not limited to adenovirus, adeno-associated virus, retrovirus and herpes virus vectors, in addition to other particles that introduce DNA into cells, such as liposomes.

A polynucleotide of the invention can be expressed using any promoter known in the art capable of expression in mammalian, preferably human cells. Such promoters can be inducible or constitutive. These promoters include, but are not limited to, a casein promoter (Cerdan et al., 1998, "Accurate spatial and temporal transpolynucleotide expression driven by a 3.8-kilobase promoter of the bovine beta-casein polynucleotide in the lactating mouse mammary gland", Mol Reprod Dev. 49:236–45), whey acid promoter (Doppler et al., 1991, "Lactogenic hormone and cell type-specific control of the whey acidic protein polynucleotide promoter in transfected mouse cells", Mol Endocrinol. 5:1624–1632), SV40 early promoter region (Bernoist and Chambon, 1981, Nature 290:304–310), the promoter comprised in the 3' long terminal repeat of Rous sarcoma virus (Yamamoto et al., 1980, Cell 22:787–797), the herpes thymidine kinase promoter (Wagner et al., 1981, "Nucleotide sequence of the thymidine kinase polynucleotide of herpes simplex virus type 1", Proc Natl Acad Sci. 78:1441–1445) and the regulatory sequences of the metallothionein polynucleotide (Brinster et al., 1982, "Regulation of metallothionein—thymidine kinase fusion plasmids injected into mouse eggs", Nature 296:39–42).

In one embodiment in which recombinant cells are used in polynucleotide therapy, nucleotides complementary to polynucleotides encoding polypeptides of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (See, e.g., PCT Publication WO 94/08598; Stemple and Anderson, 1992, Cell 71:973–985; Pittelkow and Scott, 1986, Mayo Clinic Proc. 61:771; Rheinwald, 1980, Meth Cell Bio. 21A:229).

In a specific embodiment, the polynucleotide to be introduced for purposes of polynucleotide therapy comprises an inducible promoter operably linked to the coding region, such that expression of the polynucleotide is controllable by controlling the presence or absence of the appropriate inducer of transcription.

A polynucleotide encoding a biologically active portion of a polypeptide of the invention can be prepared, expressing the encoded portion of the polypeptide protein (e.g., by recombinant expression in vitro) and assessing the activity of the encoded portion of the polypeptide.

In another embodiment, an antisense BGS-19 polynucleotide comprises an appended group such as a peptide (e.g., for targeting host cell receptors in vivo ), or an agent that facilitates transport across the cell membrane (See, e.g., Letsinger et al., 1989, Proc Natl Acad Sci. 86:6553–6556; Lemaitre et al., 1987, Proc Natl Acad Sci. 84:648–652; PCT Publication No. WO 88/09810) or the blood-brain barrier (See, e.g., PCT Publication No. WO 89/10134). In another embodiment, an antisense BGS-19 polynucleotide can be modified with hybridization-triggered cleavage agents (See, e.g., Krol et al., 1988, Biotechniques 6:958–976) or intercalating agents (See, e.g., Zon, 1988, Pharm Res. 5:539–549). To this end, an antisense BGS-19 polynucleotide may be conjugated to another molecule, e.g., a peptide, hybridization triggered cross-linking agent, transport agent, or hybridization-triggered cleavage agent.

Any type of plasmid, cosmid, YAC or viral vector can be used to prepare the recombinant construct. Alternatively, vectors can be used which selectively target a tissue or cell type, e.g., viruses which infect cells of the immune system.

Further specificity can be realized by using a tissue-specific or cell-specific promoter in the expression vector.

In a specific embodiment, an expression vector is administered directly in vivo, where the vector is expressed to produce the encoded product. This can be accomplished by any of numerous methods known in the art, e.g., by placing a polynucleotide of the invention in an appropriate expression vector such that, upon administration, the vector becomes intracellular and expresses a BGS-19 antisense oligonucleotide. Such vectors can be internalized by using, for example, a defective or attenuated retroviral vector or other viral vectors that can infect mammalian cells (See, e.g., U.S. Pat. No. 4,980,286).

Alternatively, an expression construct comprising a polynucleotide of the invention can be injected directly into a target tissue as naked DNA. In another embodiment, an expression construct comprising a polynucleotide of the invention can be introduced intracellularly using microparticle bombardment, for example, by using a Biolistic polynucleotide gun (Dupont™). In another embodiment, an expression construct comprising a polynucleotide of the invention can be coated with lipids, or cell-surface receptors, or transfecting agents, such that encapsulation in liposomes, microparticles, or microcapsules facilitates access to target tissues and/or entry into target cells. In yet another embodiment, an expression construct comprising a polynucleotide of the invention is linked to a polypeptide that is internalized in a subset of cells or is targeted to a particular cellular compartment. In a further embodiment, the linked polypeptide is a nuclear targeting sequence which targets the vector to the cell nucleus. In another further embodiment, the linked polypeptide is a ligand that is internalized by receptor-mediated endocytosis in cells expressing the respective receptor for the ligand (See, e.g., Wu and Wu, 1987, J. Biol. Chem. 262:4429–4432).

In another embodiment, nucleic acid-ligand complexes can be formed such that the ligand comprises a fusogenic viral peptide which disrupts endosomes, thereby allowing the nucleic acid to avoid lysosomal degradation. In another embodiment, a polynucleotide of the invention can be targeted in vivo via a cell-specific receptor resulting in cell-specific uptake and expression (See, e.g., International Patent Publications WO 92/06180, WO 92/22635, WO 92/20316, WO 93/14188, and WO 93/2022. In yet another embodiment, a polynucleotide of the invention is introduced intracellularly and, by homologous recombination, can transiently or stably be incorporated within the host cell DNA, which then allows for its expression, (Koller and Smithies, 1989, Proc Natl Acad Sci. 86:8932–8935; Zijlstra et al., 1989, Nature 342:435–438).

In one embodiment, viral vectors are used that comprise nucleic acids encoding compounds that activate cytokine receptors (i.e., cytokines or antibodies), or compounds that activate molecules expressed on activated immune cells (See, e.g., Miller et al., 1993, Meth. Enzymol. 217:581–599). In a specific embodiment, a viral vector that comprises polynucleotides encoding 4-1BB ligand, or anti-4-1BB immunoglobulin, and/or IL-12 are used. For example, a retroviral vector can be used in which sequences not necessary for packaging of the viral genome and integration into host cell DNA have been deleted, and polynucleotide sequences encoding 4-1BB ligand, or anti-4-1BB immunoglobulin, or IL-12 are cloned into the vector, thereby facilitating delivery of the transpolynucleotide into a subject. Greater detail about retroviral vectors is available in Boesen et al., 1994, Biotherapy 6:291–302, which describes the use of a retroviral vector to deliver the mdr1 polynucleotide to hematopoietic stem cells.

Other viral vectors can be used for polynucleotide therapy approaches in accordance with the invention. For example, adenoviruses are useful for delivering polynucleotide constructs to respiratory epithelia. Other targets for adenovirus-based delivery systems are the liver, the central nervous system, endothelial cells, and muscle cells. Moreover, adenoviruses are able to infect non-dividing cells (See, e.g., Rosenfeld et al., 1991, Science 252:431–434; Rosenfeld et al., 1992, Cell 68:143–155; Mastrangeli et al., 1993, J. Clin. Invest. 91:225–234; Kozarsky and Wilson, 1993, Curr. Opin. Genetics Develop. 3:499–503; Bout et al., 1994, Human Gene Therapy 5:3–10; PCT Publication No. WO 94/12649; and Wang et al., 1995, Gene Therapy 2:775–783).

Adeno-associated virus can also be used in accordance with the polynucleotide therapy approaches of the present invention (See, e.g., Walsh et al., 1993, Proc. Soc. Exp. Biol. Med. 204:289–300; U.S. Pat. No. 5,436,146).

In this embodiment, the polynucleotide is introduced into a cell prior to administration in vivo of the resulting recombinant cell. Such introduction can be carried out by any method known in the art, including, but not limited to, transfection, electroporation, microinjection, infection with a viral or bacteriophage vector comprising the polynucleotides, cell fusion, chromosome-mediated polynucleotide transfer, microcell-mediated polynucleotide transfer, and spheroplast fusion. Numerous techniques are known in the art for the introduction of foreign polynucleotides into cells (See, e.g., Maniatis et al., 1989; *Current Protocols in Molecular Biology*, John Wiley & Sons, 2000; Loeffler and Behr, 1993, Meth. Enzymol. 217:599–618; Cohen et al., 1993, Meth Enzymol. 217:618–644; Cline, 1985, Pharmacol Ther. 29:69–92) and can be used in accordance with the present invention. In a preferred embodiment, the technique stably transfers a polynucleotide of the invention to a target cell, such that the polynucleotide is inherited by the cell's progeny.

The resulting recombinant cells can be delivered to a subject by various methods known in the art, and the skilled artisan would appreciate appropriate modes of administration. For example, intravenous administration may be the preferred mode of administration for recombinant hematopoietic stem cells. Similarly, the number of recombinant cells to be administered to a subject can be determined by one skilled in the art, and would include a consideration of factors such as the desired effect, the disease state, and the mode of administration.

Cells into which a polynucleotide of the invention can be introduced for purposes of polynucleotide therapy include, but are not limited to pWLNEO, pSV2CAT, pOG44, pXT1 and pSG available from Stratapolynucleotide; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

One skilled in the art will appreciate that many different promoters can be used to drive expression of a BGS-19 antisense construct. In one embodiment, the promoter comprises hormone-sensitive elements. For example, a promoter comprising an androgen-sensitive enhancer would be activated to greater degree in androgen-producing cells or adjacent tissues. Such an expression construct may be beneficial for targeting tissues secreting abnormally high levels of androgen. In another embodiment, the promoter comprises elements of a fibroblast-specific promoter. In a further embodiment, the fibroblast-specific promoter comprises promoter elements from synovial fibroblasts. In another embodiment, the promoter is derived from an imprinted polynucleotide, many of which are known in the art. In another embodiment, the promoter is derived from a tumor-specific promoter, many of which are known in the art.

Alternatively, the promoter comprises elements of promoters that are activated in aggressive rheumatoid arthritis synovial fibroblasts. In a particular embodiment, the promoter comprises a portion of a BGS-19 promoter. In a non-limiting example, a viral vector is used in which the viral promoter is replaced fully, or in part, with at least parts of a BGS-19 promoter. Such an expression construct would more specifically be expressed in BGS-19-expressing cells, and higher expression of a BGS-19 antisense oligonucleotide would occur in cells expressing above-normal levels of BGS-19.

Gene therapy approaches may also be used in accordance with the present invention to inhibit BGS-19. For example, ribozyme and triple helix molecules may be used to target a BGS-19 polynucleotide products resulting in a decrease in BGS-19 protein. Techniques for the production and use of antisense ribozyme and/or triple helix molecules are well known to those of skill in the art and can be designed with respect to the nucleotide sequence encoding the amino acid sequence of BGS-19.

Antisense Gene Therapy

Antisense approaches to polynucleotide therapy involve the use of riboprobes that may hybridize to a portion of the target mRNA. The skilled artisan will recognize that absolute complementarity is not required, such that some degree of mismatch can result in, at least, transitory duplex formation. In one non-limiting example, the antisense riboprobe binds to the target mRNA transcript and prevents its translation.

Riboprobes that are complementary to the 5' untranslated sequences, up to and including the AUG initiation codon, can be used effectively to inhibit translation of a BGS-19 mRNA. Additionally, riboprobes complementary to the 3' untranslated sequences of mRNAs also can be effective at inhibiting BGS-19 mRNA translation (See, e.g., Wagner, 1994, Nature 372:333–335). Moreover, antisense riboprobes complementary to mRNA coding regions can be used in accordance with the invention.

Preferably, in vitro studies are performed to assess the ability of an antisense riboprobe to inhibit polynucleotide expression. These studies typically use controls which distinguish between antisense-mediated inhibition of polynucleotide expression and nonspecific biological effects of riboprobes. Preferably, these studies compare antisense-mediated changes in the levels of the target RNA or target protein with levels of an internal control RNA or protein.

In one embodiment, a recombinant DNA construct that has a BGS-19 antisense riboprobe under the control of a pol m or pol II promoter is used to polynucleotiderate BGS-19 antisense riboprobes in a cell. The use of such a construct to transfect target cells in the subject can result in the transcription of sufficient amounts of a BGS-19 riboprobe to reduce or inhibit BGS-19 mRNA and/or protein expression. Low transfection rates or low transcription activity of the DNA construct can nevertheless polynucleotiderate sufficient BGS-19 antisense molecules to demonstrate clinical effectiveness.

In another embodiment, a BGS-19 antisense polynucleotide is cloned into an expression vector, preferably a mammalian expression vector. In a specific embodiment, the BGS-19 antisense polynucleotide comprises the sequence of a full-length BGS-19 DNA. In another specific embodiment, the BGS-19 antisense polynucleotide comprises the sequence of a 5' untranslated region, which optionally can include the sequence, AUG, indicating the start of the coding region.

In another embodiment, antisense polynucleotides of the invention are cloned into a vector, which is designed to target the vector (and thereby target expression of the antisense riboprobe) to specific tissues or cell-types. For example, an antisense riboprobe can be linked to peptides or antibodies that specifically bind receptors or antigens expressed on the target cell surface, thereby targeting the vector to cells) can be administered.

In another embodiment, the vector comprises a promoter that is more highly activated in diseased cells or tissues, as compared to normal cells or tissues.

A preferred approach to achieve intracellular concentrations of the antisense sufficient to suppress translation of endogenous mRNAs involves the use of a recombinant DNA construct in which the antisense oligonucleotide is placed under the control of a strong pol III or pol II promoter. The use of such a construct to transfect target cells in a patient will result in the transcription of sufficient amounts of single stranded RNAs that can form complementary base pairs with the endogenous BGS-19polynucleotide transcripts and thereby prevent translation of the BGS-19 polynucleotide mRNA. For example, a vector can be introduced in vivo such that the vector is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter comprised in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), and the regulatory sequences of the metallothionein polynucleotide (Brinster et al., 1982, Nature 296:39–42). Any type of plasmid, cosmid, YAC (yeast artificial chromosome), or viral vector can be used to prepare the recombinant DNA construct which can be introduced directly into the tissue site. Alternatively, viral vectors that selectively infect the desired tissue can be used.

A construct designed for polynucleotide therapy approaches can also be used in contexts no involving polynucleotide therapy.

Ribozyme Therapy

The invention also provides for ribozymes targeting BGS-19 expression. Ribozymes are enzymatic RNA molecules capable of catalyzing the specific cleavage of a single-stranded nucleic acid, such as an mRNA (See, e.g., Rossi, 1994, Current Biology 4:469–471). The mechanism of a trans-acting ribozyme action involves sequence-specific hybridization of the ribozyme molecule to a complementary target, followed by an endonucleolytic cleavage. The composition of ribozyme molecules include one or more sequences complementary to the target polynucleotide mRNA, and catalytic sequences responsible for mRNA cleavage (See, e.g., U.S. Pat. No. 5,093,246 which is incorporated by reference in its entirety). Thus, ribozymes, e.g., hammerhead ribozymes (Haselhoff and Gerlach, 1988, Nature 334:585–591), can be used to catalytically cleave mRNA transcripts thereby inhibiting the expression of a protein encoded by a particular mRNA. A trans-acting ribozyme having specificity for a polynucleotide encoding a polypeptide of the invention can be designed based upon the nucleotide sequence of the polynucleotides of the invention. Accordingly, in one embodiment, an engineered hammerhead motif ribozyme molecule specifically and efficiently catalyzes endonucleolytic cleavage of RNA sequences encoding a BGS-19 polypeptide of the invention.

In another embodiment, an mRNA encoding a polypeptide of the invention is used to select a catalytic RNA having a specific ribonuclease activity from a pool of RNA molecules (See, e.g., Bartel and Szostak, 1993, Science 261: 1411–1418).

Specific ribozyme cleavage sites within a potential RNA target are identified by scanning the molecule of interest for ribozyme cleavage sites, which include the sequences GUA, GUU and GUC. Once identified, short RNA sequences of approximately 15 to 20 ribonucleotides corresponding to a cleavage site of a target polynucleotide are evaluated for predicted structural features, such as secondary structure, that may make the oligonucleotide suitable. The suitability of candidate sequences also can be evaluated by testing their ability to hybridize with complementary oligonucleotides, using for example, ribonuclease protection assays.

In one embodiment, a ribozyme in the form of an antisense riboprobe is polynucleotiderated from a mammalian expression vector. In another embodiment, a ribozyme in the form of an oligonucleotide administered directly to the patient. In a further embodiment, the ribozyme is administered systemically. In another further embodiment, the ribozyme is administered directly to the cells or tissue, in vivo or ex vivo.

The ribozymes of the present invention also include RNA endoribonucleases, such as the ribozyme which occurs naturally in Tetrahymena thermophila (also known as the IVS, or L-19 IVS RNA) and has been extensively described (Zaug et al., 1984, Science 224:574–578; Been and Cech, 1986, Cell 47:207–216; Zaug and Cech, 1986, Science 231:470–475; Zaug et al., 1986, Nature 324:429–433; published International Patent Publication No. WO 88/04300). These ribozymes have an 8 bp active site which hybridizes to a target RNA sequence to cause cleavage of the target RNA. Accordingly, the invention encompasses ribozymes that target active sites comprising 8 bp, which are present in a BGS-19 polynucleotide.

As discussed for antisense approaches, supra, the ribozymes of the invention can be composed of modified oligonucleotides (e.g. for improved stability or targeting) and should be delivered to cells that express a BGS-19 polynucleotide in vivo. A preferred method of delivery involves using a DNA construct "encoding" the ribozyme under the control of a strong constitutive pol III or pol II promoter, so that transfected cells will produce sufficient quantities of the ribozyme to cause degradation of an endogenous BGS-19 mRNA and thereby inhibit translation. Because ribozymes unlike antisense molecules, are catalytic, a relatively low intracellular concentration is required for efficiency.

Ribozymes of the invention can be prepared by any method known in the art for the synthesis of DNA and RNA molecules. For example, chemical synthesis can be achieved by synthesizing oligodeoxyribonucleotides and oligoribonucleotides using solid phase phosphoramidite chemical synthesis. Alternatively, ribozyme polynucleotides can be polynucleotiderated by in vitro or in vivo transcription of DNA sequences. Such DNA sequences can be incorporated into a wide variety of vectors which incorporate suitable RNA polymerase promoters such as the T7 or SP6 polymerase promoters. Alternatively, antisense cDNA constructs can be introduced stably into cell lines, such that the synthesize ribozymes are expressed constitutively or inducibly, depending on the promoter used.

Triple Helix Therapy

The invention also encompasses polynucleotides which form triple helical structures. For example, expression of a polypeptide of the invention can be inhibited by targeting nucleotide sequences complementary to the regulatory region of the polynucleotide encoding the polypeptide (e.g., the promoter and/or enhancer) to form triple helical structures that prevent transcription of the polynucleotide in target cells (see, e.g., Helene, 1991, Anticancer Drug Des. 6:569–584; Helene, 1992, Ann NY Acad Sci. 660:27–36; Maher, 1992, Bioassays 14:807–815).

Polynucleotides to be used to inhibit transcription by triple helix formation can be single stranded oligonucleotides. The base composition of these oligonucleotides can be designed to promote triple helix formation via Hoogsteen base pairing rules, preferably with long stretches of purines or pyrimidines on one strand of the duplex. Nucleotide sequences can be pyrimidine-based thereby resulting in TAT and CGC+triplets] across the three associated strands of the resulting triple helix. The pyrimidine-rich molecules provide base complementarity to a purine-rich region of a single strand of the duplex in a parallel orientation to that strand. Purine-rich polynucleotides also can be chosen, for example, comprising a stretch of guanine residues. These molecules can form a triple helix with a DNA duplex that is rich in GC pairs, in which most of the purine residues are located on a single strand of the targeted duplex, resulting in GGC triplets across the three strands in the triplex.

Additionally, the number of potential sequences that can be targeted for triple helix formation can be increased by creating a "switchback" polynucleotide. Switchback molecules are synthesized in an alternating 5'-3', 3'-5' manner, such that the molecule first hybridizes with one strand of a duplex, followed by hybridization with another strand, thus eliminating the requirement for a stretch of purines or pyrimidines on one strand of a duplex.

Ribozyme and triple helix molecules of the invention can be prepared by any method known in the art for the synthesis of DNA or RNA molecules (e.g., oligodeoxyribonucleotides or oligoribonucleotides). Such methods include, for example, solid phase phosphoramidite chemical synthesis. For further examples of methods of synthesis, see Section 5.6.14 regarding methods for synthesis of antisense oligonucleotides, supra.

These oligonucleotides can be administered directly, for example, via injection. Alternatively, RNA molecules can be polynucleotiderated in vitro or in vivo by transcription of DNA sequences. Such DNA sequences may be incorporated into a wide variety of vectors known in the art that feature a suitable RNA polymerase promoter such as, for example, a T7 or SP6 polymerase promoter.

Antibody Gene Therapy

In one embodiment, polynucleotides comprising sequences encoding antibodies that bind to a BGS-19 are administered via polynucleotide therapy. In a particular embodiment, recombinant cells are used that comprise polynucleotides encoding antibodies to BGS-19 polypeptides of the invention. The polynucleotide construct is expressed such that the recombinant antibody is secreted or expressed on the cell surface. The recombinant cells are then administered in vivo for therapeutic effect.

Antibodies of the invention, including antibodies conjugated to therapeutic moieties, can be administered to an individual alone or in combination with a chemotherapeutic drug, cytotoxic factor, and/or cytokine. In one embodiment, an antibodies directed to a BGS-19 polypeptide is administered first, followed by chemotherapeutic drug, cytotoxic factor, and/or cytokine within 24 hours. The treatment cycle can be repeated if warranted by the clinical response of the patient. Furthermore, the antibody, chemotherapeutic drug, cytotoxic factor, and/or cytokine can be administered via separate routes, such as for example, by intravenous and intramuscular administration. Cytotoxic factors include, but are not limited to, TNF-α, TNF-β, IL-1, IFN-γ, and IL-2. Chemotherapeutic drugs include, but are not limited to, 5-fluorouracil (5FU), vinblastine, actinomycin D, etoposide, cisplatin, methotrexate, and doxorubicin. Cytokines include, but are not limited to, IL-2, IL-3, IL-4, IL-5, IL-6, IL-7, IL-8, IL-9, IL-10, and IL-12.

Vaccine Therapy

The nucleotides of the invention, including variants and derivatives, can be used as vaccines, e.g., by polynucleotidetic immunization. Genetic immunization is particularly advantageous as it stimulates a cytotoxic T-cell response but does not utilize live attenuated vaccines, which can revert to a virulent form and infect the host causing the very infection sought to be prevented. As used herein, polynucleotidetic immunization comprises inserting the nucleotides of the invention into a host, such that the nucleotides are taken up by cells of the host and the proteins encoded by the nucleotides are translated. These translated proteins are then either secreted or processed by the host cell for presentation to immune cells and an immune reaction is stimulated. Preferably, the immune reaction is a cytotoxic T cell response, however, a humoral response or macrophage stimulation is also useful in preventing future infections. The skilled artisan will appreciate that there are various methods for introducing foreign nucleotides into a host animal and subsequently into cells for polynucleotidetic immunization, for example, by intramuscular injection of about 50 mg of plasmid DNA encoding the proteins of the invention solubilized in 50 ml of sterile saline solution, with a suitable adjuvant (See, e.g., Weiner and Kennedy, 1999, Scientific American 7:50–57; Lowrie et al., 1999, Nature 400:269–271).

Combination Therapies

The administration of a BGS-19 antagonist can potentiate the effect of anti-cancer agents. In a preferred embodiment, the invention further encompasses the use of combination therapy to prevent or treat cancer.

In one embodiment, breast cancer can be treated with a pharmaceutical composition comprising a BGS-19 antagonist in combination with 5-fluorouracil, cisplatin, docetaxel, doxorubicin, Herceptin®, gemcitabine (Seidman, 2001, "Gemcitabine as single-agent therapy in the management of advanced breast cancer", Oncology 15:11–14), IL-2, paclitaxel, and/or VP-16 (etoposide).

In another embodiment, prostate cancer can be treated with a pharmaceutical composition comprising a BGS-19 antagonist in combination with paclitaxel, docetaxel, mitoxantrone, and/or an androgen receptor antagonist (e.g., flutamide).

In another embodiment, leukemia can be treated with a pharmaceutical composition comprising a BGS-19 antagonist in combination with fludarabine, cytosine arabinoside, gemtuzumab (MYLOTARG), daunorubicin, methotrexate, vincristine, 6-mercaptopurine, idarubicin, mitoxantrone, etoposide, asparaginase, prednisone and/or cyclophosphamide. As another example, myeloma can be treated with a pharmaceutical composition comprising a BGS-19 antagonist in combination with dexamethasone.

In another embodiment, melanoma can be treated with a pharmaceutical composition comprising a BGS-19 antagonist in combination with dacarbazine.

In another embodiment, colorectal cancer can be treated with a pharmaceutical composition comprising a BGS-19 antagonist in combination with irinotecan.

In another embodiment, lung cancer can be treated with a pharmaceutical composition comprising a BGS-19 antagonist in combination with paclitaxel, docetaxel, etoposide and/or cisplatin.

In another embodiment, non-Hodgkin's lymphoma can be treated with a pharmaceutical composition comprising a BGS-19 antagonist in combination with cyclophosphamide, CHOP, etoposide, bleomycin, mitoxantrone and/or cisplatin.

In another embodiment, gastric cancer can be treated with a pharmaceutical composition comprising a BGS-19 antagonist in combination with cisplatin.

In another embodiment, pancreatic cancer can be treated with a pharmaceutical composition comprising a BGS-19 antagonist in combination with gemcitabine.

These combination therapies can also be used to prevent cancer, prevent the recurrence of cancer, or prevent the spread or metastasis or cancer.

Combination therapy also includes, in addition to administration of a BGS-19 antagonist, the use of one or more molecules, compounds or treatments that aid in the prevention or treatment of cancer (i.e., cancer therapeutics), which molecules, compounds or treatments includes, but is not limited to, chemoagents, immunotherapeutics, cancer vaccines, anti-angiogenic agents, cytokines, hormone therapies, polynucleotide therapies, and radiotherapies.

In one embodiment, one or more chemoagents, in addition to a BGS-19 antagonist, is administered to treat a cancer patient. A chemoagent (or "anti-cancer agent" or "anti-tumor agent" or "cancer therapeutic") refers to any molecule or compound that assists in the treatment of tumors or cancer. Examples of chemoagents contemplated by the present invention include, but are not limited to, cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, *Bacillus Calmette* and *Guerin*, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, colchicine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gemcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

In one embodiment, said chemoagent is gemcitabine at a dose ranging from 100 to 1000 mg/m$^2$/cycle. In one embodiment, said chemoagent is dacarbazine at a dose ranging from 200 to 4000 mg/m$^2$/cycle. In a preferred embodiment, said dose ranges from 700 to 1000 mg/m$^2$/cycle. In another embodiment, said chemoagent is fludarabine at a dose ranging from 25 to 50 mg/m$^2$/cycle. In another embodiment, said chemoagent is cytosine arabinoside (Ara-C) at a dose ranging from 200 to 2000 mg/m$^2$/cycle. In another embodiment, said chemoagent is docetaxel at a dose ranging from 1.5 to 7.5 mg/kg/cycle. In another embodiment, said chemoagent is paclitaxel at a dose ranging from 5 to 15 mg/kg/cycle. In yet another embodiment, said chemoagent is cisplatin at a dose ranging from 5 to 20 mg/kg/cycle. In yet another embodiment, said chemoagent is 5-fluorouracil at a dose ranging from 5 to 20 mg/kg/cycle. In yet another embodiment, said chemoagent is doxorubicin at a dose ranging from 2 to 8 mg/kg/cycle. In yet another embodiment, said chemoagent is epipodophyllotoxin at a dose ranging from 40 to 160 mg/kg/cycle. In yet another embodiment, said chemoagent is cyclophosphamide at a dose ranging from 50 to 200 mg/kg/cycle. In yet another embodiment, said chemoagent is irinotecan at a dose ranging from 50 to 75, 75 to 100, 100 to 125, or 125 to 150 mg/m$^2$/cycle. In yet another embodiment, said chemoagent is vinblastine at a dose ranging from 3.7 to 5.4, 5.5 to 7.4, 7.5 to 11, or 11 to 18.5 mg/m$^2$/cycle. In yet another embodiment, said chemoagent is vincristine at a dose ranging from 0.7 to 1.4, or 1.5 to 2 mg/m$^2$/cycle. In yet another embodiment, said chemoagent is methotrexate at a dose ranging from 3.3 to 5, 5 to 10, 10 to 100, or 100 to 1000 mg/m$^2$/cycle.

In a preferred embodiment, the invention further encompasses the use of low doses of chemoagents when administered as part of a BGS-19 antagonist treatment regimen. For example, initial treatment with a BGS-19 antagonist increases the sensitivity of a tumor to subsequent challenge with a dose of chemoagent, which dose is near or below the lower range of dosages when the chemoagent is administered without a BGS-19 antagonist. In one embodiment, a BGS-19 antagonist and a low dose (e.g., 6 to 60 mg/m$^2$/day or less) of docetaxel are administered to a cancer patient. In another embodiment, a BGS-19 antagonist and a low dose (e.g., 10 to 135 mg/m$^2$/day or less) of paclitaxel are administered to a cancer patient. In yet another embodiment, a BGS-19 antagonist and a low dose (e.g., 2.5 to 25 mg/m$^2$/day or less) of fludarabine are administered to a cancer patient. In yet another embodiment, a BGS-19 antagonist and a low dose (e.g., 0.5 to 1.5 g/m$^2$/day or less) of cytosine arabinoside (Ara-C) are administered to a cancer patient.

The invention, therefore, contemplates the use of one or more BGS-19 antagonists, which is administered prior to, subsequently, or concurrently with low doses of chemoagents, for the prevention or treatment of cancer.

In one embodiment, said chemoagent is gemcitabine at a dose ranging from 10 to 100 mg/m$^2$/cycle.

In one embodiment, said chemoagent is cisplatin, e.g., PLATINOL or PLATINOL-AQ (Bristol Myers), at a dose ranging from 5 to 10, 10 to 20, 20 to 40, or 40 to 75 mg/m$^2$/cycle. In another embodiment, a dose of cisplatin ranging from 7.5 to 75 mg/m$^2$/cycle is administered to a patient with ovarian cancer. In another embodiment, a dose of cisplatin ranging from 5 to 50 mg/m$^2$/cycle is administered to a patient with bladder cancer.

In another embodiment, said chemoagent is carboplatin, e.g., PARAPLATIN (Bristol Myers), at a dose ranging from 2 to 4, 4 to 8, 8 to 16, 16 to 35, or 35 to 75 mg/m$^2$/cycle. In another embodiment, a dose of carboplatin ranging from 7.5 to 75 mg/m$^2$/cycle is administered to a patient with ovarian cancer. In another embodiment, a dose of carboplatin ranging from 5 to 50 mg/m$^2$/cycle is administered to a patient with bladder cancer. In another embodiment, a dose of carboplatin ranging from 2 to 20 mg/m$^2$/cycle is administered to a patient with testicular cancer.

In another embodiment, said chemoagent is docetaxel, e.g., TAXOTERE (Rhone Poulenc Rorer) at a dose ranging from 6 to 10, 10 to 30, or 30 to 60 mg/m$^2$/cycle.

In another embodiment, said chemoagent is paclitaxel, e.g., TAXOL (Bristol Myers Squibb), at a dose ranging from 10 to 20, 20 to 40, 40 to 70, or 70 to 135 mg/kg/cycle.

In another embodiment, said chemoagent is 5-fluorouracil at a dose ranging from 0.5 to 5 mg/kg/cycle.

In another embodiment, said chemoagent is doxorubicin, e.g., ADRIAMYCIN (Pharmacia & Upjohn), DOXIL (Alza), RUBEX (Bristol Myers Squibb), at a dose ranging from 2 to 4, 4 to 8, 8 to 15, 15 to 30, or 30 to 60 mg/kg/cycle.

In another embodiment, a BGS-19 antagonist is administered in combination with one or more immunotherapeutic agents, such as antibodies and immunomodulators, which includes, but is not limited to, Herceptin®, Retuxan®, OvaRex, Panorex, BEC2, IMC-C225, Vitaxin, Campath I/H, Smart M195, LymphoCide, Smart I D10, and Oncolym, rituxan, rituximab, gemtuzumab, or trastuzumab.

In another embodiment, a BGS-19 antagonist is administered in combination with one or more anti-angiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077–2083), a 14-amino acid peptide corresponding to a fragment of collagen I (Tolma et al., 1993, J. Cell Biol. 122:497–511), a 19 amino acid peptide corresponding to a fragment of Thrombospondin I (Tolsma et al., 1993, J. Cell Biol. 122:497–511), a 20-amino acid peptide corresponding to a fragment of SPARC (Sage et al., 1995, J. Cell. Biochem. 57:1329–1334), or any fragments, family members, or derivatives thereof, including pharmaceutically acceptable salts thereof.

Other peptides that inhibit angiopolynucleotidesis and correspond to fragments of laminin, fibronectin, procollagen, and EGF have also been described (see, e.g., Cao, 1998, Prog Mol Subcell Biol. 20:161–176). Monoelonal antibodies and cyclic pentapeptides, which block certain integrins that bind RGD proteins (i.e., possess the peptide motif Arg-Gly-Asp), have been demonstrated to have antivascularization activities (Brooks et al., 1994, Science 264: 569–571; Hammes et al., 1996, Nature Medicine 2:529–533). Moreover, inhibition of the urokinase plasminogen activator receptor by receptor antagonists inhibits angiopolynucleotidesis, tumor growth and metastasis (Min et al., 1996, Cancer Res. 56: 2428–33; Crowley et al., 1993, Proc Natl Acad Sci. 90:5021–25). Use of such anti-angiogenic agents is also contemplated by the present invention.

In another embodiment, a BGS-19 antagonist is administered in combination with a regimen of radiation.

In another embodiment, a BGS-19 antagonist is administered in combination with one or more cytokines, which includes, but is not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In yet another embodiment, a BGS-19 antagonist is administered in combination with a cancer vaccine. Examples of cancer vaccines include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-specific antigens (e.g., BAGE, GAGE-1, GAGE-2, MAGE-1, MAGE-3, N-acetylglucosaminyltransferase-V, p15), mutated antigens that are tumor-specific (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma)). For human tumor antigens recognized by T cells, see polynucleotiderally Robbins and Kawakami, 1996, Curr. Opin. Immunol. 8:628–36. Cancer vaccines may or may not be purified preparations.

In yet another embodiment, a BGS-19 antagonist is used in association with a hormonal treatment. Hormonal therapeutic treatments comprise hormonal agonists, hormonal antagonists (e.g., flutamide, tamoxifen, leuprolide acetate (LUPRON), LH-RH antagonists), inhibitors of hormone biosynthesis and processing, and steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

In yet another embodiment, a BGS-19 antagonist is used in association with a polynucleotide therapy program in the treatment of cancer. In one embodiment, polynucleotide therapy with recombinant cells secreting interleukin-2 is administered in combination with a BGS-19 antagonist to prevent or treat cancer, particularly lymphoma (See, e.g., Deshmukh et al., 2001, J Neurosurg. 94:287–292).

In one embodiment, a BGS-19 antagonist is administered, in combination with at least one cancer therapeutic agent, for a short treatment cycle to a cancer patient to treat cancer. The duration of treatment with the cancer therapeutic agent may vary according to the particular cancer therapeutic agent used. The invention also contemplates discontinuous administration or daily doses divided into several partial administrations. An appropriate treatment time for a particular cancer therapeutic agent will be appreciated by the skilled artisan, and the invention contemplates the continued assessment of optimal treatment schedules for each cancer therapeutic agent.

The present invention contemplates at least one cycle, preferably more than one cycle during which a single therapeutic or sequence of therapeutics is administered. An appropriate period of time for one cycle will be appreciated by the skilled artisan, as will the total number of cycles, and the interval between cycles. The invention contemplates the continued assessment of optimal treatment schedules for each BGS-19 antagonist and cancer therapeutic agent.

Pharmaceutical Compositions

Since inhibition of expression of a BGS-19 polynucleotide or inhibition of a BGS-19 protein can have significant therapeutic responses in a patient with a BGS-19-related disorder, the invention provides useful pharmaceutical compositions, treatment courses, and modes of delivery. Accordingly, in one embodiment, a pharmaceutical composition comprises a polynucleotide or polypeptide of the invention, and derivatives thereof, which refers to any pharmaceutically acceptable homolog, analogue, or fragment corresponding to the pharmaceutical composition of the invention. In another embodiment, the present invention provides for a pharmaceutical composition that comprises a BGS-19 antagonist and a pharmaceutically acceptable carrier.

The carrier can be a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic lipids, including, but not limited to N-(1(2,3-dioleyloxy) propyl)-N,N,N-trimethylammonium chloride ("DOTMA") and diolesylphosphotidylethanolamine ("DOPE"). Liposomes are also suitable carriers for the antisense oligonucleotides of the invention. Such compositions should comprise a therapeutically effective amount of the compound, together with a suitable amount of carrier so as to provide the form for proper administration to the patient. The formulation should suit the mode of administration.

Pharmaceutically acceptable salts are prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride ("DOTMA"), diolesylphosphotidylethanolamine ("DOPE") and liposomes. Such compositions should comprise a therapeutically effective amount of the compound, together with a suitable amount of carrier so as to provide an appropriate formulation for administration to a patient. For example, oral administration requires enteric coatings to protect the antagonist from degradation within the gastrointestinal tract. In another example, the antagonist may be administered in a liposomal formulation to facilitate transport in circulatory system, effect delivery across cell membranes to intracellular sites, and shield the antagonist from degradative enzymes.

In another embodiment, a pharmaceutical composition comprises a BGS-19 antagonist and one or more therapeutic agents and a pharmaceutically acceptable carrier. In a particular embodiment, the pharmaceutical composition comprises a BGS-19 antagonist and one or more cancer therapeutic agents and a pharmaceutically acceptable carrier.

In a further embodiment, a pharmaceutical composition, comprising a BGS-19 antagonist, with or without other therapeutic agents, and a pharmaceutically acceptable carrier, is at an effective dose.

The compositions of the invention can be formulated as neutral or salt forms. Pharmaceutically acceptable salts include those formed with free amino groups, such as for example, those derived from hydrochloric, phosphoric, acetic, oxalic, and tartaric acids, and those formed with free carboxyl groups, such as for example, those derived from sodium, potassium, ammonium, calcium, ferric hydroxides, isopropylamine, triethylamine, 2-ethylamino ethanol, histidine, and procaine.

In a preferred embodiment, the composition is formulated in accordance with routine procedures as a pharmaceutical composition adapted for subcutaneous injection or intravenous administration to humans. Typically, compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

The polynucleotides, polypeptides, and antibodies of the invention can be incorporated into pharmaceutical compositions suitable for administration. Such compositions typically comprise the polynucleotide, protein, or antibody, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the pharmaceutical compositions of the invention is contemplated.

The invention includes methods for preparing pharmaceutical compositions for modulating the expression or activity of a polypeptide or polynucleotide of the invention. Such methods comprise formulating a pharmaceutically acceptable carrier with an agent which modulates expression or activity of a polypeptide or polynucleotide of the invention. Such compositions can further include additional active agents. Thus, the invention further includes methods for preparing a pharmaceutical composition by formulating a pharmaceutically acceptable carrier with an agent which modulates expression or activity of a polypeptide or polynucleotide of the invention and additional polynucleotides, polypeptides, and antibodies of the invention.

Selection of a preferred effective dose can be determined by a skilled artisan based upon the consideration of factors which will be known to one of ordinary skill in the art. Such factors include the particular form of a BGS-19 antagonist and its pharmacokinetic parameters such as bioavailability, metabolism and half-life, which is established during the development procedures typically employed in obtaining regulatory approval of a pharmaceutical compound. Further factors that can be used to determine an effective dose include the disease to be treated, the benefit to be achieved in a patient, the patient's body mass, the patient's immune status, the route of administration, whether administration of a BGS-19 antagonist and/or combination therapeutic agent is acute or chronic, concomitant medications, and other factors known by the skilled artisan to affect the efficacy of administered pharmaceutical agents.

In one embodiment, the pharmaceutical composition comprises a BGS-19 antisense oligonucleotide at a dose of about 0.01 to 0. 1, 0.1 to 0.9, 1 to 5, or 6 to 10 mg/kg/day; and a pharmaceutically acceptable carrier. The actual amount of any particular antisense oligonucleotide administered can depend on several factors, such as the type of disease, the toxicity of the antisense oligonucleotide to normal cells of the body, the rate of uptake of the antisense oligonucleotide by tumor cells, and the weight and age of the individual to whom the antisense oligonucleotide is administered. The skilled artisan will appreciate the factors that may interfere with the action or biological activity of the antisense oligonucleotide in vivo, an effective amount of the antisense oligonucleotide can be determined empirically by routine procedures, including, for example, via clinical trials.

In another embodiment, the pharmaceutical compositions of the invention comprise a BGS-19 antisense oligonucleotide at a particularly high dose, which ranges from about 10 to 50 mg/kg/day. In a specific embodiment a particularly high dose of BGS-19 antisense oligonucleotide, ranging from 11 to 15, 16 to 20, 21 to 25, 26 to 30, 31 to 35, 36 to 40, 41 to 45, or 46 to 50 mg/kg/day, is administered during a treatment cycle.

A preferred effective dose of a BGS-19 antisense oligonucleotide can be determined by a skilled artisan, especially given that several antisense oligonucleotide compounds are currently undergoing clinical trials. These routine trials can establish the particular form of antisense oligonucleotide to be administered, an appropriate delivery route, and a particular antisense oligonucleotide's pharmacokinetic parameters such as bioavailability, metabolism, and half-life. Other factors typically considered during the course of a clinical trial are the patient's body mass, the patient's immune status, the disease to be treated, the benefit to be achieved in a patient, the route of administration, whether administration of an antisense oligonucleotide and/or combination therapeutic agent is acute or chronic, concomitant medications, and other factors known by the skilled artisan to affect the efficacy of administered pharmaceutical agents.

Modes of Administration

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. A pharmaceutical composition of the invention is formulated to be compatible with its intended route of administration. Examples of routes of administration include parenteral, e.g., intravenous, intramuscular, intraperitoneal, intraorbital, intracapsular, intraspinal, intrasternal, intra-arterial, intradermal, subcutaneous, oral (e.g., inhalation), transdermal (topical), transmucosal, and rectal administration. The skilled artisan can appreciate the specific advantages and disadvantages to be considered in choosing a mode of administration.

Multiple modes of administration are encompassed by the invention. For example, a BGS-19 antagonist is administered by subcutaneous injection, whereas a combination therapeutic agent is administered by intravenous infusion.

A BGS-19 antagonist can be administered before, during, and/or after the administration of one or more therapeutic agents. In one embodiment, a BGS-19 antagonist can first be administered to cancer patient to reduce the expression of BGS-19, which increases the tumor's sensitivity to subsequent challenge with a cancer therapeutic agent. In another embodiment, a BGS-19 antagonist can be administered after administration of a cancer therapeutic agent to reduce tumor expression of BGS-19, which can deter tumor resistance, and thereby prevent relapse or minimization of response to the cancer therapeutic agent. In yet another embodiment, there can be a period of overlap between the administration of BGS-19 antagonist and one or more cancer therapeutic agents.

Moreover, administration of one or more species of BGS-19 antagonist, with or without other therapeutic agents, may occur simultaneously (i.e., co-administration) or sequentially. In one embodiment, a BGS-19 antagonist is first administered to increase sensitivity of a tumor to subsequent administration of a cancer therapeutic agent or irradiation therapy. In another embodiment, the periods of administration of one or more species of a BGS-19 antagonist, with or without other therapeutic agents may overlap. For example, a BGS-19 antagonist is administered for 14 days, and a second therapeutic agent is introduced beginning on the seventh day of BGS-19 antagonist treatment, and treatment with the second therapeutic agent continues beyond the 14-day BGS-19 antagonist treatment.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide, for example. The parenteral preparation can be enclosed in ampules, disposable syringes or multiple dose vials made of glass or plastic.

Pharmaceutical compositions adapted for parenteral administration include, but are not limited to, aqueous and non-aqueous sterile injectable solutions or suspensions, which may contain antioxidants, buffers, bacteriostats and solutes that render the compositions substantially isotonic with the blood of an intended recipient. Such compositions may also comprise water, alcohols, polyols, glycerine and vegetable oils, for example. Compositions adapted for parenteral administration can be packaged in unit-dose or multi-dose containers (e.g., sealed ampules and vials). These compositions can be stored in a freeze-dried (lyophilized) condition, which requires the addition of a sterile liquid carrier, e.g., sterile saline solution for injections, prior to use. Extemporaneous injection solutions and suspensions may be prepared from sterile powders, granules and tablets. Such compositions should comprise a therapeutically effective amount of a BGS-19 antagonist and/or other therapeutic agent, together with a suitable amount of carrier so as to provide the form for proper administration to the patient. The formulation should suit the mode of administration.

Systemic administration can also be by transmucosal or transdermal means. For transmucosal or transdermal administration, penetrants appropriate to the barrier to be permeated are used in the formulation. Penetrants for transmucosal administration are polynucleotiderally known in the art, and include, for example, detergents, bile salts, and fusidic acid derivatives. Transmucosal administration can be accomplished through the use of nasal sprays or suppositories. For transdermal administration, the active compounds are formulated into ointments, salves, gels, or creams as polynucleotiderally known in the art.

Pharmaceutical compositions adapted for transdermal administration can be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols, or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable compositions. In these compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for oral administration may be provided, for example, as capsules, tablets, powders, granules, solutions, syrups, suspensions (in aqueous or non-aqueous liquids), edible foams, whips, or emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatin capsules may comprise, for example, vegetable oils, waxes, fats, semi-solid, or liquid polyols. Solutions and syrups may comprise, for example, water, polyols and sugars.

Pharmaceutically compatible binding agents, and/or adjuvant materials can be included as part of the composition. The tablets, pills, capsules, and troches can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location. Oral formulations preferably comprise 10% to 95% active ingredient by weight.

Pharmaceutical compositions adapted for nasal administration can comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers such as, for example, nasal sprays or nasal drops. These compositions may comprise aqueous or oil solutions of the active ingredient. Compositions for administration by inhalation may be supplied in specially adapted devices including, but not limited to, pressurized aerosols, nebulizers, or insufflators, which can be constructed so as to provide predetermined dosages of the active ingredient.

Pharmaceutical compositions adapted for rectal administration can be prepared in the form of suppositories (e.g., with conventional suppository bases such as cocoa butter and other glycerides) or retention enemas for rectal delivery. Pharmaceutical compositions adapted for vaginal administration may be provided, for example, as pessaries, tampons, creams, gels, pastes, foams, or spray formulations.

In one embodiment, a pharmaceutical composition of the invention is delivered by a controlled-release system. For example, the pharmaceutical composition may be administered using intravenous infusion, an implantable osmotic pump, a transdermal patch, liposomes, or other modes of administration. In one embodiment, a pump may be used (See, e.g., Langer, 1990, Science 249:1527–1533; Sefton, 1987, CRC Crit Ref Biomed Eng. 14:201; Buchwald et al., 1980, Surgery 88:507; Saudek et al., 1989, N Engl J Med. 321:574). In another embodiment, the compound can be delivered in a vesicle, in particular a liposome (See, e.g., Langer, 1990, Science 249:1527–1533; Treat et al., 1989, in *Liposomes in the Therapy of Infectious Disease and Cancer*, Lopez-Berestein and Fidler (eds.) Liss, New York, pp. 353–365; Lopez-Berestein, ibid., pp. 317–327; International Patent Publication No. WO 91/04014; U.S. Pat. No. 4,704,355). In another embodiment, polymeric materials can be used (See, e.g., *Medical Applications of Controlled Release*, Langer and Wise (eds.) CRC Press: Boca Raton, Fla., 1974; *Controlled Drug Bioavailability, Drug Product Design and Performance*, Smolen and Ball (eds.) Wiley: New York (1984); Ranger and Peppas, 1953, J. Macromol Sci Rev Macromol Chem. 23:61; Levy et al., 1985, Science 228:190; During et al., 1989, Ann. Neurol. 25:351; Howard et al., 1989, J Neurosurg. 71:105).

In one embodiment, the active compounds, which comprise polynucleotides, polypeptides, or antibodies of the invention, are prepared with carriers that will protect the compound from rapid elimination from the body. Such carriers can be a controlled release formulation, which includes, but is not limited to, implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In a particular embodiment, polypeptides of the invention can be administered using a biodegradable polymer having reverse thermal gelatin properties (See, e.g., U.S. Pat. No. 5,702,717).

In yet another embodiment, a controlled release system can be placed in proximity of the target. For example, a micropump may deliver controlled doses directly into the axillary lymph node region, thereby requiring only a fraction of the systemic dose (See, e.g., Goodson, 1984, in *Medical Applications of Controlled Release*, vol. 2, pp. 115–138).

In one embodiment, it may be desirable to administer a pharmaceutical composition of the invention locally to the area in need of treatment; this may be achieved, for example, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers. Suppositories polynucleotiderally comprise active ingredients in the range of 0.5% to 10% by weight.

Pharmaceutical compositions suitable for injectable use include sterile aqueous solutions, or dispersions, or sterile powders (for the extemporaneous preparation of sterile injectable solutions or dispersions). For intravenous administration, suitable carriers include physiological saline, bacteriostatic water, Cremophor EL™ (BASF; Parsippany, N.J.) or phosphate buffered saline (PBS). The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, or by the use of a surfactant. Prevention of the action of microorganisms can be achieved by various antibacterial and antifungal agents, such as for example, parabens, chlorobutanol, phenol, ascorbic acid, and thimerosal. It can be preferable to include in the composition isotonic agents, such as for example, sugars, polyalcohols (e.g., mannitol), sorbitol, and sodium chloride. Prolonged absorption of the injectable compositions can be brought about by including in the composition an agent which delays absorption, such as for example, aluminum monostearate and gelatin.

Sterile injectable solutions can be prepared by incorporating the required amount of an active compound (e.g., a polypeptide or antibody) in an appropriate solvent with one or a combination of ingredients enumerated above, as required, followed by filtered sterilization. Generally, dispersions are prepared by incorporating the active compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder comprising the active ingredient.

For administration by inhalation, the compounds are delivered in the form of an aerosol spray from a pressurized container or dispenser which comprises a suitable propellant, e.g., a gas such as carbon dioxide, or a nebulizer.

Oral or parenteral compositions can be formulated in dosage unit form for ease of administration and uniformity of dosage. Dosage unit form as used herein refers to physically discrete units suited as unitary dosages for the subject to be treated, such that each unit contains a predetermined quantity of active compound, which is calculated to produce the desired therapeutic effect, and a pharmaceutical carrier. The skilled artisan will appreciate that dosage unit forms are dependent on the unique characteristics of the active compound, the particular therapeutic effect to be achieved, and the limitations inherent in the art of compounding such an active compound for human administration.

For antibodies, the preferred dosage is 0.1 mg/kg to 100 mg/kg of body weight (polynucleotiderally 10 mg/kg to 20 mg/kg). For example, if the antibody is to act in the brain, a dosage of 50 mg/kg to 100 mg/kg is usually appropriate. Since partially human antibodies and fully human antibodies polynucleotiderally have a longer half-life in a patient than other antibodies, lower dosages and less frequent administration is possible. Modifications, such as lipidation, can be used to stabilize antibodies and to enhance uptake and tissue penetration (See, e.g., Cruikshank et al., 1997, J Acquir Immune Defic Syndr Hum Retrovirol. 14:193–203).

In one embodiment, a therapeutically effective amount of a polypeptide of the invention ranges from about 0.001 to 30 mg/kg body weight. In another embodiment, a therapeutically effective amount of a polypeptide of the invention ranges from about 0.01 to 25 mg/kg body weight. In another embodiment, a therapeutically effective amount of a polypeptide of the invention ranges from about 0.1 to 20 mg/kg body weight. In yet another embodiment, a therapeutically effective amount of a polypeptide of the invention ranges from about 1 to 10 mg/kg, 2 to 9 mg/kg, 3 to 8 mg/kg, 4 to 7 mg/lkg, or 5 to 6 mg/kg body weight.

The skilled artisan will appreciate that certain factors may influence the dose necessary to effectively treat a subject, which factors include, but are not limited to, previous treatment regimens, severity of the disease or disorder, polynucleotideral health and/or age of the subject, and concurrent diseases. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Kits

The invention also encompasses kits for detecting the presence of a BGS-19 polypeptide or polynucleotide of the invention in a biological sample (a test sample). Such kits can be used to determine if a subject is suffering from or is at increased risk of developing a disorder associated with aberrant expression of a polypeptide of the invention as discussed, for example, in sections above relating to uses of the sequences of the invention.

In an exemplary embodiment, a kit comprises, in a first container, a purified BGS-19 polynucleotide, BGS-19 polypeptide, BGS-19 agonist, BGS-19 antagonist, and in a second container, a molecule that binds to the BGS-19 polynucleotide, BGS-19 polypeptide, BGS-19 agonist, BGS-19 antagonist when bound to an analyte in a biological sample. The molecule can be, for example, a detectable tag that recognizes a complex comprising BGS-19 and the analyte such that the interaction between BGS-19 and the analyte is identified.

For example, kits can be used to determine if a subject is suffering from or is at increased risk of disorders such as cancer, in particular hormone-sensitive cancers, such as but not limited to cancer of the breast, ovary, uterus, prostate, testis, skin and brain.

In another example, kits can be used to determine if a subject is suffering from or is at risk for a disorder associated with aberrant expression of a polypeptide of the invention.

The kit, for example, can comprise a labeled compound or agent capable of detecting the BGS-19 polypeptide or BGS-19 mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the BGS-19 polypeptide or the first antibody and is conjugated to a detectable agent.

For oligonucleotide-based kits, the kit can comprise, for example: (1) an oligonucleotide, e.g., a detectably labeled oligonucleotide, which hybridizes to a BGS-19 polynucleotide sequence encoding a polypeptide of the invention or (2) a pair of primers useful for amplifying a polynucleotide encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also comprise a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

The invention provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition comprises an antibody of the invention, a therapeutic moiety, and a pharmaceutically acceptable carrier.

The pharmaceutical compositions of the invention can be included in a container, pack, or dispenser together with instructions for administration.

EXAMPLES

Example 1

Identification of BGS-19 Gene

IgSF protein sequences with immunoglobulin domains from several different species, were used as probes to search the human genomic sequence database. The search program used was Gapped BLAST (Altschul et al., 1997, "Gapped BLAST and PSI-BLAST: a new polynucleotideration of protein database search programs", Nucleic Acids Res. 25:3389–3402). The best genomic exon matches from the BLAST results were then searched against the non-redundant protein and patent sequence databases. From this analysis, exons encoding potential novel open reading frames (ORF) were identified based on sequence homology. The protein sequences with the greatest similarity were then used as templates to predict additional exons using the GENE-WISEDB program (Birney and Durbin, 2000, "Using Gene-Wise in the Drosophila annotation experiment", Genome Res. 10:547–548). The final predicted exons were assembled and consensus sequences of polynucleotides were obtained using the predicted exon sequences. With these analyses, a predicted partial sequence of a novel human cell surface IgSF protein, named BGS-19 was identified directly from a human genomic sequence ACOI 1452. The computationally predicted nucleotide and amino acid sequences of BGS-19 are depicted in FIGS. 1–4.

The isolated full-length of BGS-19 is a 1985-bp cDNA that encodes a 385 amino acid protein (see, e.g., FIGS. 3–4). A search of BGS-19 against protein databases identified Siglec-6, Siglec-7, and Siglec-10 as the three closest homologs of BGS-19. Using the global alignment program, GAP, from the GCG bioinformatics software package, BGS-19 was found to have 41.4% identity and 48.0% similarity to Siglec-6, 44.7% identity and 50.8% similarity to Siglec-7 protein, and 46.6% identity and 51.7% similarity to Siglec-10 protein (FIGS. 4A–E). Similar to Siglec-6, Siglec-7 and Siglec-10, BGS-19 has a predicted signal peptide cleavage site between residues 15 and 16 (predicted by SPScan program from GCG software package). There is a predicted single transmembrane domain between residues 250 and 275 (SEQ ID NO:8). BGS-19 is a type I cell surface receptor. Two predicted Ig domains are in the extracellular region at residues 16–113 and residues 140–241, (HMM Pfam search, Bateman et al., 2000).

BGS-19 has a typical ITIM (immuno-receptor tyrosine-based inhibitory motif, residues 329–334=LHYASL). Tyr 331 is part of a typical ITIM signature. Many studies have shown that all of the inhibitory receptors identified thus far are characterized by one or more ITIMs in their cytoplasmic tail. Upon tyrosine phosphorylation, ITIM binds the src homology (SH2) domains of phophatases such as SHP-1 and SHP-2, resulting in the downregulation of natural killer cell triggering and cytotoxicity (Renard et al., 1997, "Transduction of cytotoxic signals in natural killer cells: a polynucleotideral model of fine tuning between activatory and inhibitory pathways in lymphocytes", Immunol Rev. 155:205–221). Recently, Siglec-7 (p75/AIRM 1), was found to function as an inhibitory receptor in human natural killer cells (Falco et al., 1999, "Identification and molecular cloning of p75/AIRM 1, a novel member of the sialoadhesin family that functions as an inhibitory receptor in human natural killer cells", J Exp Med. 190:793–802). As such, BGS-19 can be useful as an inhibitory receptor.

BGS-19 is highly expressed in lung and lymphocyte-rich tissues, such as spleen, lymph node and bone marrow (FIG. 6). Therefore, BGS-19 can be useful for studies and manipulations involving cells of the immune system. See, e.g., Whitney et al., 2001, "A new siglec family member, siglec-10, is expressed in cells of the immune system and has signaling properties similar to CD33", Eur J Biochem. 268:6083–6096 (demonstrating high expression of Siglec-10 in asthmatic eosinophils). As such, BGS-19 can be useful as a signaling molecule.

Example 2

Cloning of the Novel Human BGS-19

A multiplex cloning method was used to extend the bioinformatic polynucleotide prediction for BGS19 into full length cDNA. The multiplex cloning method is used to extend large numbers of bioinformatic polynucleotide predictions into full length sequences by multiplexing probes and cDNA libraries to minimize the overall effort typically required for cDNA cloning. Plasmid-based directionally cloned cDNA libraries are converted into a population of pure, covalently-closed, circular, single-stranded molecules. Long biotinylated DNA oligo probes are designed from predicted polynucleotide sequences. Probes and libraries are hybridized in solution in formamide buffer rather than in the aqueous buffers recommended in other biotin/strepavidin cDNA capture methods (i.e., GeneTrapper). Information on the representation of clones in the libraries is not required to perform the hybridization. The hybridization is carried out twice. After the first selection, the isolated sequences are screened with PCR primers specific for the targeted clones. The second hybridization is carried out with only those oligo probes whose polynucleotide-specific PCR assays gave positive results. The secondary hybridization serves to 'normalize* the selected library thereby decreasing the amount of screening needed to identify particular clones. The method is robust and sensitive. Typically, dozens of cDNAs are isolated for any one particular polynucleotide, thereby increasing the chances of obtaining a full-length cDNA. The entire complexity of any cDNA library is screened in the solution hybridization process, which is advantageous for finding rare sequences. Although 50 oligo probes per experiment are currently being used, larger numbers of probes can also be used.

General Cloning Strategy

Using bioinformatic predicted polynucleotide sequence, the following types of polynucleotide-specific PCR primers and cloning oligos are designed:

A) PCR primer pairs that reside within a single predicted exon;

B) PCR primer pairs that cross putative exon/intron boundaries; and

C) an 80 mer antisense and sense oligo with a biotin moiety on the 5' end.

The primer pairs from the A type primer are optimized on human genomic DNA; the B type primers are optimized on a mixture of first strand cDNAs made with and without reverse transcriptase, from brain and testis poly $A^+$ RNA. The information obtained with the B type primers is used to assess which putative expressed sequences exhibit reverse transcriptase dependent expression. The A type primer pairs are less stringent for identifying expressed sequences, because they amplify genomic DNA as well as cDNA. However, because the A type primers can amplify genomic DNA, they provide the necessary positive control for the primer pair. Negative results using the B type primer are only valid upon confirmation, with the positive control, that the sequence is indeed expressed in the first strand.

The biotinylated 80 mer oligos are added en masse to pools of single stranded cDNA libraries. Up to 50 probes have been successfully used on pools for 15 different libraries. The orientation of the oligo depends on the orientation of the cDNA in its vector. Antisense 80 mer oligos are used for those libraries and cloned into pCMVSPORT and pSPORT whereas sense 80 mer oligos are used for cDNA libraries cloned into pSPORT2. After the primary selection is carried out, all of the captured DNA is repaired to double stranded form using the T7 primer for the commercial libraries in pCMVSPORT, and the Sp6 primer for in-house constructed libraries in pSPORT. The resulting DNA is electroporated into E. coli DH12S and plated onto 150 mm plates with nylon filters. The cells are scraped from the plate and a frozen stock is made. This is the primary selected library. One-fifth of the library is converted into single strand form and the DNA assayed with the polynucleotide specific primers pairs (GSPs). The second round of hybridization is carried out with 80 mer oligos for only those sequences that were positive with the polynucleotide-specific-primers. After the second round, the captured single strand DNAs are repaired with a pool of GSPs, where only the primer complementary to the single-stranded circular DNA is used (the antisense primer for pCMVSPORT and pSPORT1 and the sense primer for pSPORT2). The resulting colonies are screened by PCR using the GSPs. Typically, greater than 80% of the clones are positive for any given GSP. DNA from each well of the entire 96 well block of clones was prepared and each of the clones sized by either PCR or restriction enzyme digestion. A selection of clones for each targeted sequence are chosen for transposon-hopping and DNA sequencing.

Success of the method, like any cDNA cloning method, depends of on the quality of the libraries employed. High complexity and large average insert size are required. HPLC is used to fractionate cDNA to construct libraries.

Example 3

Construction of A Size Fractionated cDNA Library for the Isolation of Large Insert Clones Poly $A^+$ RNA from Clontech is treated with DNase I to remove genomic DNA contamination. The RNA is converted into double stranded cDNA using the SuperScript Plasmid System for cDNA Synthesis and Plasmid Cloning (Life Technologies). The cDNA is size fractionated on a TransGenomics HPLC size exclusion column (TosoHass) with dimensions of 7.8mm×30 cm and a particle size of 10 μm. Tris buffered saline is used as the mobile phase, and the column is run at a flow rate of 0.5 ml/min. The system is calibrated using a 1 kb ladder to determine which fractions are to be pooled to obtain the largest cDNA library. Generally, fractions that eluted in the range of 12 to 15 minutes are used. The cDNA is precipitated, concentrated and then ligated into the Sal I/Not I sites in pSPORT. Following electroporation of the cDNA into DH12S, DNA from the resulting colonies is prepared and subjected to Sal I/Not I restriction enzyme digestion. Generally, the average insert size of libraries made by this procedure is greater than 3.5 Kb and the overall complexity of the library is greater than $10^7$ independent clones. The library is amplified in semi-solid agar for 2 days at 30 C. An aliquot (200 microliters) of the amplified library is inoculated into a 200 ml culture for single-stranded DNA isolation by super-infection with a fi helper phage. The single-stranded circular DNA is concentrated by ethanol precipitation, resuspended at a concentration of one microgram per microliter and used for the cDNA capture experiments.

Example 4

Conversion of Double Stranded cDNA Libraries into Single Strand Circular Form

I. Preparation of Culture.

LB medium (200 mL+400 μl carb) is inoculated with 0.2 to 1 ml of thawed cDNA library. The culture is incubated, shaking at 250 rpm at 37° C. for 45 min. The optical density of the culture is measured. The OD600 is preferably between 0.025 and 0.040. One mL M13K07 helper phage is added to the culture and grown for 2 hours. At that time, 500 μL Kanamycin (30 mg/mL) is added and incubation continued for 15–18 hours.

II. Preparation of Cells for Precipitation.

Cultures are poured into six 50 mL tubes. Cells are centrifuged at 10000 rpm in an HB-6 rotor for 15 minutes at 4° C. The supernatant is retrieved and cells discarded. The supernatant is filtered through a 0.2 μm filter. DNase I (12000 units from Gibco) is added and incubated at room temperature for 90 minutes.

III. PEG Precipitation of DNA.

Fifty mL of ice-cold 40% PEG 8000, 2.5 M NaCl, 10 mM $MgSO_4$ is added to the cell pellets. The solution is mixed and distributed into 6 centrifuge tubes and covered with parafilm. The tubes are incubated on wet ice for 1 hour (or at 4° C. overnight).

Phage are pelleted at 10000 rpm in an HB-6 rotor for 20 minutes at 4° C. The supernatant is discarded and the sides of the tubes wiped dry. The pellets are resuspended in 1 mL TE, pH 8.

The resuspended pellets are placed in a 14 mL Sarstedt tube (6 mL total). SDS is added to 0.1% (60 μL of stock 10% SDS). Proteinase K (60 μL of 20 mg/mL) is then added and incubated at 42C for 1 hour.

DNA is extracted with phenol/chloroform by first adding 1 mL of 5M NaCl followed by an equal volume of phenol/chloroform (6 mL). The mixture is vortexed and centrifuged at 5K in an HB-6 rotor for 5 minutes at 4° C. The aqueous (top) phase is transferred to a new Sarstedt tube. Extractions are repeated until no interface is visible.

The DNA is precipitated in ethanol by adding 2 volumes of 100% ethanol and precipitating overnight at −20° C. The DNA is centrifuged at 10000 rpm in HB-6 rotor for 20 minutes at 4° C. The ethanol is discarded and the pellets resuspended in 700 μL 70% ethanol. The resuspended pellets are centrifuged at 14000 rpm for 10 minutes at 4° C. The ethanol is discarded and the pellets dried by vacuum.

Oligosaccharides are then removed by resuspending the pellet in 50 μL TE, pH 8. The solutions are frozen on dry ice for 10 minutes and centrifuged at 14000 rpm for 15 minutes at 4° C. The supernatant is transferred to a new tube and the volume recorded.

The concentration of DNA is determined by measuring absorbance at 260/280. DNA is diluted 1:100 in a quartz cuvette (3 μL DNA+297 μL TE). The following equation is used to calculate DNA concentration:

(32 μg/mL*OD)(mL/100 μL)(100)(OD260)=DNA concentration

The preferred purity ratio is 1.7–2.0.

The DNA is diluted to 1 μg/uL with TB, pH 8 and stored at 4° C.

To test the quality of single-stranded DNA (ssDNA) the following reaction mixtures are prepared:
1. DNA mix per reaction
   a. 1 μL of 5 ng/μL ssDNA (1:200 dilution of V.I.D.2 above)
   b. 11 μL dH2O
   c. 1.5 μL 10 μM T7 SPORT primer (fresh dilution of stock)
   d. 1.5 μL 10× Precision-Taq buffer
2. Repair mix per reaction
   a. 4 μL 5 mM dNTPs (1.25 mM each)
   b. 1.5 μL 10× Precision-Taq buffer
   c. 9.25 μL dH2O
   d. 0.25 μL Precision-Taq polymerase
   e. Preheat cocktail at 70° C. until middle of thermal cycle The DNA mixes are aliquoted into PCR tubes and thermal cycle carried out as follows:
1. 95° C., 20 sec
2. 59° C., 1 min; add 15 μL repair mix
3. 73° C., 23 min Ethanol precipitation of the ssDNA is performed by adding 15 μg glycogen, 16 μL 7.5 M $NH_4OAc$, 125 μL 100% ethanol. The sample is centrifuged at 14000 rpm for 30 minutes at 4° C. and the pellet washed with 125 μL 70% ethanol. The ethanol is discarded and pellet dried by vacuum. The pellet is resuspended in 10 μL TB, pH 8.

The DNA is electroporated into DH10B or DH12S cells. A DNA mixture consisting of:
1. 2 μL repaired library (=1.0×10−3 μg)
2. 1 μL 1 ng/μL unrepaired library (=1.0×10−3 μg)
3. 1 μL 0.01 μg/uL pUC19 positive control DNA (=1× 10−5 μg)

is aliquoted to Eppendorf tubes. Cells are thawed on ice-water. Forty μL of cells are added to each DNA aliquot by pipetting into a chilled cuvette placed between metal plates. Electroporation is carried out at 1.8 kV. Immediately following electroporation, 1 mL SOC (SOB+glucose+$Mg^{++}$) media is added to the cuvette, then transferred to a 15 mL tube. Cells are allowed to recover for 1 hr at 37° C. with shaking (225 rpm). Cells are then plated according to the following dilution scheme:
A. Dilutions of Culture
   1. Serial dilutions of culture in 1:10 increments (20 μL into 180 μL LB broth)
   2. Repaired dilutions
      a. 1:100
      b. 1:1K
      c. 1:10K
   3. Unrepaired dilutions
      a. 1:10
      b. 1:100
   4. Positive control dilutions
      a. 1:10
      b. 1:100

100 μL of each dilution is plated on small LB+carb plates and incubated at 37° C. overnight. Colonies are counted to calculate titer as follows:
1. use smallest countable dilution
2. (# of colonies)(dilution factor)(200 μL/100 μL)(1000 μL/20 μL)=CFUs
3. CFUs/μg DNA used=CFU/μg % Background=(unrepaired CFU/μg /repaired CFU/ μg)×100%

Example 5

Solution Hybridization and DNA Capture

One microliter of anti-sense biotinylated oligos (or sense oligos when annealing to single stranded DNA from pSPORT2 vector), containing one hundred and fifty nanograms of 1 to 50 different 80 mer oligo probes, is added to six microliters (six micrograms) of a mixture of up to 15 single-stranded covalently closed circular cDNA libraries and seven microliters of 100% formamide in a 0.5 ml PCR tube. The sequence of the 80 mer oligos used is as follows: TGGGCTGGTCCGTCCTTTGAACC AGTAGCCATAAG-CAGCAGTAGACTCGTCCCAGCCATC-CCGGGGGTAGGAGA GGTTGC (SEQ ID NO:57). The mixture is heated in a thermal cycler to 95° C. for 2 min. Fourteen microliters of 2× hybridization buffer (50% formamide, 1.5 M NaCl, 0.04 M $NaPO_4$, pH 7.2, 5 min EDTA, 0.2% SDS) is added to the heated probe/cDNA library mixture and incubated at 42° C. for 26 hours. Hybrids between the biotinylated oligo and the circular cDNA are isolated by diluting the hybridization mixture to 220 microliters solution containing 1 M NaCl, 10 mm Tris-HCl pH 7.5, 1 mM EDTA, pH 8.0 and adding 125 microliters of streptavidin magnetic beads. This solution is incubated at 42° C. for 60 min, and mixed every 5 min to re-suspend the beads. The beads are separated from the solution with a magnet and washed three times in 200 microliters of 0.1× SSPE, 0.1% SDS at 45° C.

The single stranded cDNA is released from the biotinylated oligo/streptavidin magnetic bead complex by adding 50 microliters of 0.1 N NaOH and incubating at room temperature for 10 min. Six microliters of 3 M sodium acetate is added along with 15 micrograms of glycogen and the solution ethanol precipitated with 120 microliters of 100% ethanol. The precipitated DNA is resuspended in 12 microliters of TB (10 min TrisHCl, pH 8.0), 1 mM EDTA, pH 8.0). The single-stranded cDNA is converted into double-stranded DNA in a thermal cycler by mixing 5 microliters of the captured DNA with 1.5 microliters of 10 micromolar standard SP6 primer for libraries in pSPORT1 and 2 and 17 primer for libraries in pCMVSPORT and 1.5 microliters of 10×PCR buffer.

Sequences of primers used to repair single-stranded circular DNA isolated from the primary selection are as follows:

```
T7Sport   5'-TAATACGACTCACTATAGGG-3' (SEQ ID NO:58)

SP6Sport  5'-ATTTAGGTGACACTATAG-3'   (SEQ ID NO:59)
```

The mixture is heated to 95° C. for 20 seconds and the temperature gradually brought down to 59° C. Fifteen microliters of a repair mix, that was preheated to 70° C. is added to the DNA (repair mix contains 4 microliters of 5 mM dNTPs (1.25 mM each), 1.5 microliters of 10× PCR buffer, 9.25 microliters of water, and 0.25 microliters of Taq polymerase). The solution incubation temperature is raised back to 73° C. and incubated for 23 mm. The repaired DNA is ethanol precipitated and resuspended in 10 microliters of TB. Electroporation is carried out using two microliters DNA per 40 microliters of E. coli DH12S cells. Three hundred and thirty three microliters are plated onto one 150-mm plate of LB agar plus 100 micrograms/milliliter of ampicillin. After overnight incubation at 37° C., the colonies from all plates are harvested by scraping into 10 ml of LB medium+50 micrograms/milliliter of ampicillin and 2 ml of sterile glycerol.

The second round of selection is initiated by making single-stranded circular DNA from the primary selected library using the method listed above. The purified single-stranded circular DNA is then assayed with polynucleotide-specific primers for each of the targeted sequences using standard PCR conditions.

The sequences of the Gene-Specific-Primer ("GSP") pairs used to identify the various targeted cDNAs in the primary selected single stranded cDNA libraries are as follows:

```
Left Primer    CATCGTGTCTTGCAACCTCT  (SEQ ID NO:60)
1:

Right Primer   CTCTCTCCACCCGAAAGAAG  (SEQ ID NO:61)
1:
```

The secondary hybridization is carried out using only those 80 mer biotinylated probes whose targeted sequences were positive with the GSPs. The resulting single-stranded circular DNA is converted to double strands using the antisense oligo for each target sequence as the repair primer (the sense primer is used for material captured from pSPORT2 libraries. The resulting double stranded DNA is electroporated into DH1OB and the resulting colonies inoculated into 96 deep well blocks. Following overnight growth, DNA is prepared and sequentially screened for each of the targeted sequences using the GSPs. The DNA is also cut with Sal I and Not I and the inserts sized by agarose gel electrophoresis.

Example 6

Expression Profile of BGS-19

The same PCR primer pair that was used to identify BGS-19 cDNA clones was used to measure the steady state levels of mRNA by quantitative PCR (SEQ ID NO:60 and 61). Briefly, first strand cDNA was made from commercially available mRNA (Clontech) and subjected to real time quantitative PCR using a PE 5700 instrument (Applied Biosystems, Foster City, Calif.) which detects the amount of DNA amplified during each cycle by the fluorescent output of SYBR green, a DNA binding dye specific for double strands. The specificity of the primer pair for its target is verified by performing a thermal denaturation profile at the end of the run which gives an indication of the number of different DNA sequences present by determining melting Tm. In the case of the BGS-19 primer pair, only one DNA fragment was detected having a homopolynucleotideous melting point. Contributions of contaminating genomic DNA to the assessment of tissue abundance is controlled for by performing the PCR with first strand made with and without reverse transcriptase. In all cases, the contribution of material amplified in the no reverse transcriptase controls was negligible.

Small variations in the amount of cDNA used in each tube was determined by performing a parallel experiment using a primer pair for a polynucleotide expressed in equal amounts in all tissues, cyclophilin. These data were used to normalize the data obtained with the BGS-19 primer pair. The PCR data was converted into a relative assessment of the difference in transcript abundance amongst the tissues tested and the data are presented in bar graph form. Transcripts corresponding to BGS-19 are found in highest concentration in RNA isolated from the spleen and lung.

| Primer pair used for profiling | | |
|---|---|---|
| BGS19.2s | AAGAACCAGACCAAGCACCT | (SEQ ID NO:80) |
| BGS19.2a | CCCTTTCTGGAGAAGTCCAC | (SEQ ID NO:81) |

Detail Methods

DNase the RNA

I. Dilute 5 μg of poly A+ RNA to 77 uL w/DEPC H2O

II. Rxn mix—make cocktail for samples +1 extra reaction for pipetting errors

| Components | vol/rxn |
|---|---|
| 10X PCR Buffer | 10 λ |
| 25 mM MgCl2 | 8 λ |
| RNase-Out 40 U/uL | 2.5 λ |
| RNase-Free Dnase (B-M) | 2.5 λ |
| | 23 λ |

A. Add 23 λ mix to each sample  
B. Incubate @ RT, 15'  
C. Add 1 micorliters 250 mM EDTA  
D. Incubate @ 6 degrees C., 15 minutes on ice III. Clean-Up  
A. Extract w/100 λ Phenol:Chloroform:Isoamyl Alcohol  
  1. Vortex 1 minute  
  2. Spin @ 12K rpm 2 minute  
  3. Remove 90–95 λ of the top aqueous phase, transfer to new tube  
B. Ethanol precipitation  
  1. Add 1 λ 20 ug/λ glycogen, 15 λ 2M NaAcetate, 290 λ 100% EtOH  
  2. ppt @ −2 degrees C. for 1 h  
  3. Pellet @ 4 degrees C., for 30 minutes  
  4. Wash in 500 λ 70% EtOH, dry  
  5. Resuspend in 22 uL RNase-free WATER First Strand cDNA Synthesis I. Split volume of RNA above into 2 tubes (RT+/RT−)  
II. Prime  
  A. Add 1 λ Oligo(dT) to each  
  B. Incubate @ 7 degrees C., 10 minutes on ice  
III. Rxn mix—make cocktail for samples +1 extra reaction for pipetting errors

| Components | Vol/rxn |
|---|---|
| 10X PCR Buffer | 2 λ |
| 25 mM MgCl2 | 2 λ |
| 10 mM dNTP mix | 1 λ |
| 0.1 M DTT | 2 λ |
| | 7 λ |

A. Add 7 λ mix to each sample  
B. Incubate @ 4 degrees C., 5 minutes  
C. Add 1 λ SuperScript II RT to RT+ and 1 λ DEPC WATER to RT− samples  
D. Incubate @ 4 degrees C., 50 minutes  
IV. Terminate rxn @ 7 degrees C., 15 minutes on ice  
V. Add 1 λ RNase H, incubate @ 3 degrees C., 20 minutes  
VI. Add 79 λ water final conc.=2.5 ng/uL cDNA (assuming 100% conversion)

Quantitative PCR

I. Determine number of rxns and amount of mix needed  
  A. all samples run in triplicate, so sample tubes need 3.5 rxns worth of mix  
  B. =(2×# tissue samples+1 no template control+1 for pipetting error)(3.5)

II. Rxn mix

| Components | vol/rxn |
|---|---|
| 2X SybrGreen Master Mix | 25 λ |
| water | 23.5 λ |
| primer mix (10 uM ea.) | 0.5 λ |
| cDNA (2.5 ng/uL) | 1 λ |

A. Make mix minus cDNA for enough reactions as determined above  
B. Aliquot 171.5 λ of mix to sample tubes  
C. Add 3.5 λ of cDNA to each sample tube  
D. Mix gently and spin down to collect  
E. Aliquot 3×50 λ to optical plate  
III. Set up 5700  
  A. Enter primer and sample set-up  
  B. Save (plate) As . . .  
  C. Run default program including dissociation protocol  
    1) Hold, 2 min, 50° C.  
    2) Hold, 10 min, 95° C.  
    3) Cycle 40 cycles  
      Melt, 15 sec, 96° C.  
      Anneal/Extend, 1 min, 60° C.

Example 7

Method of Assessing the Expression Profile of the Novel BGS-19 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18 s and 28 s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For BGS-19, the primer probe sequences were as follows

```
Forward Primer
5'-CAGGGATGGTTCCAAAGTGAA-3'      (SEQ ID NO:86)

Reverse Primer
5'-GTGCGACTCCCACACACTTG-3'       (SEQ ID NO:87)

TaqMan Probe
5'-AGGTCTCCATGGCAACAGGACACCA-3'  (SEQ ID NO:88)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription reaction and Sequence Detection 100 ng of Dnase-treated total RNA was annealed to 2.5 µM of the respective gene-specific reverse primer in the presence of 5.5 mM Magnesium Chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TaqMan probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

Figure 7:
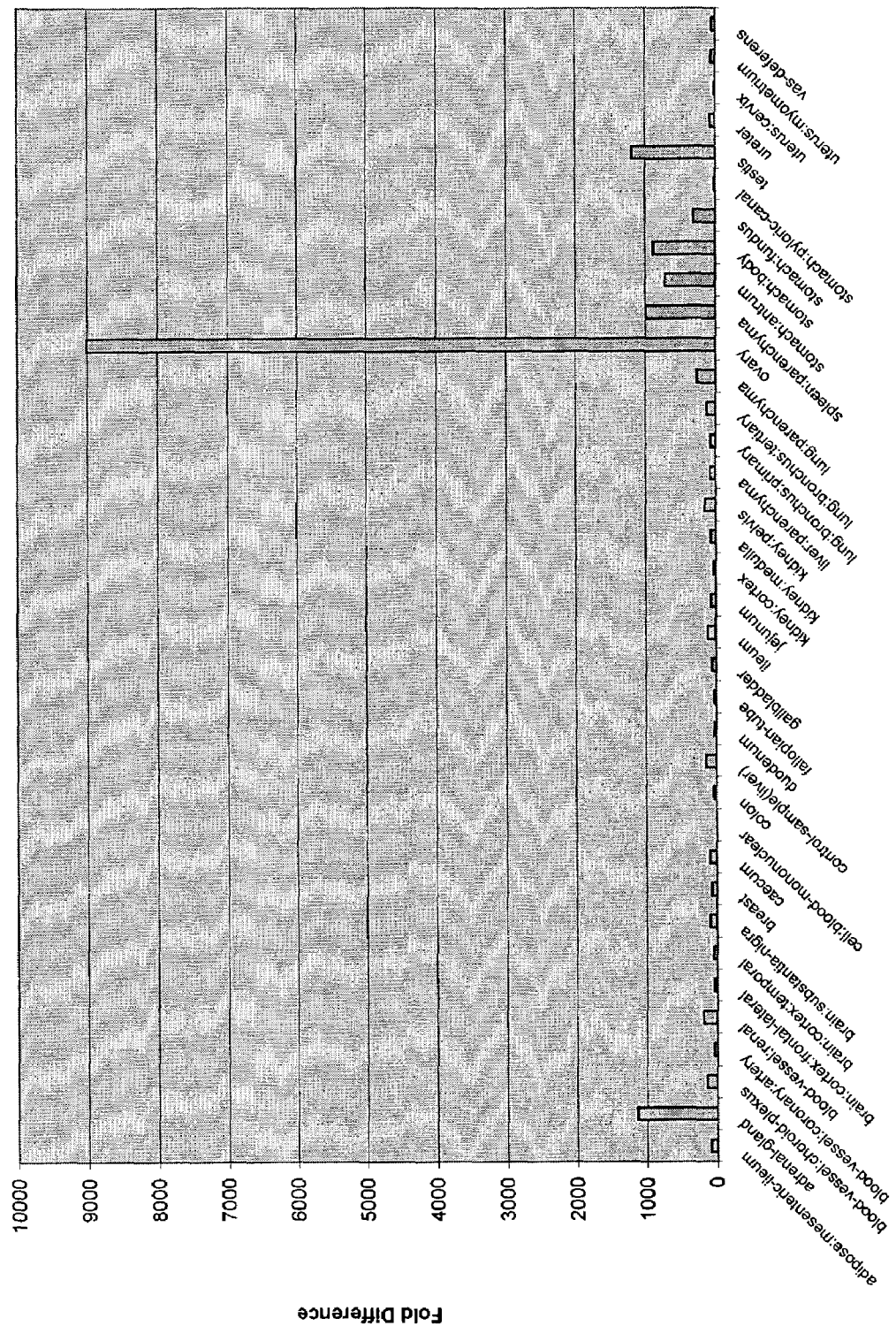
FIG. 7 shows an expanded expression profile of the novel human cell surface protein with immunoglobulin folds, BGS-19. The figure illustrates the relative expression level of BGS-19 amongst various mRNA tissue sources. As shown, the BGS-19 polypeptide was expressed predominately in the ovary. Expression of BGS-19 was also significantly expressed in the testis, adrenal gland, the parenchyma of the spleen, throughout the stomach, and to a lesser extent in the other tissues as shown. Expression data was obtained by measuring the steady state BGS-19 mRNA levels by quantitative PCR using the PCR primer pair provided as SEQ ID NO:85 and 86, and Taqman probe (SEQ ID NO:87) as described herein.
Figure 8:
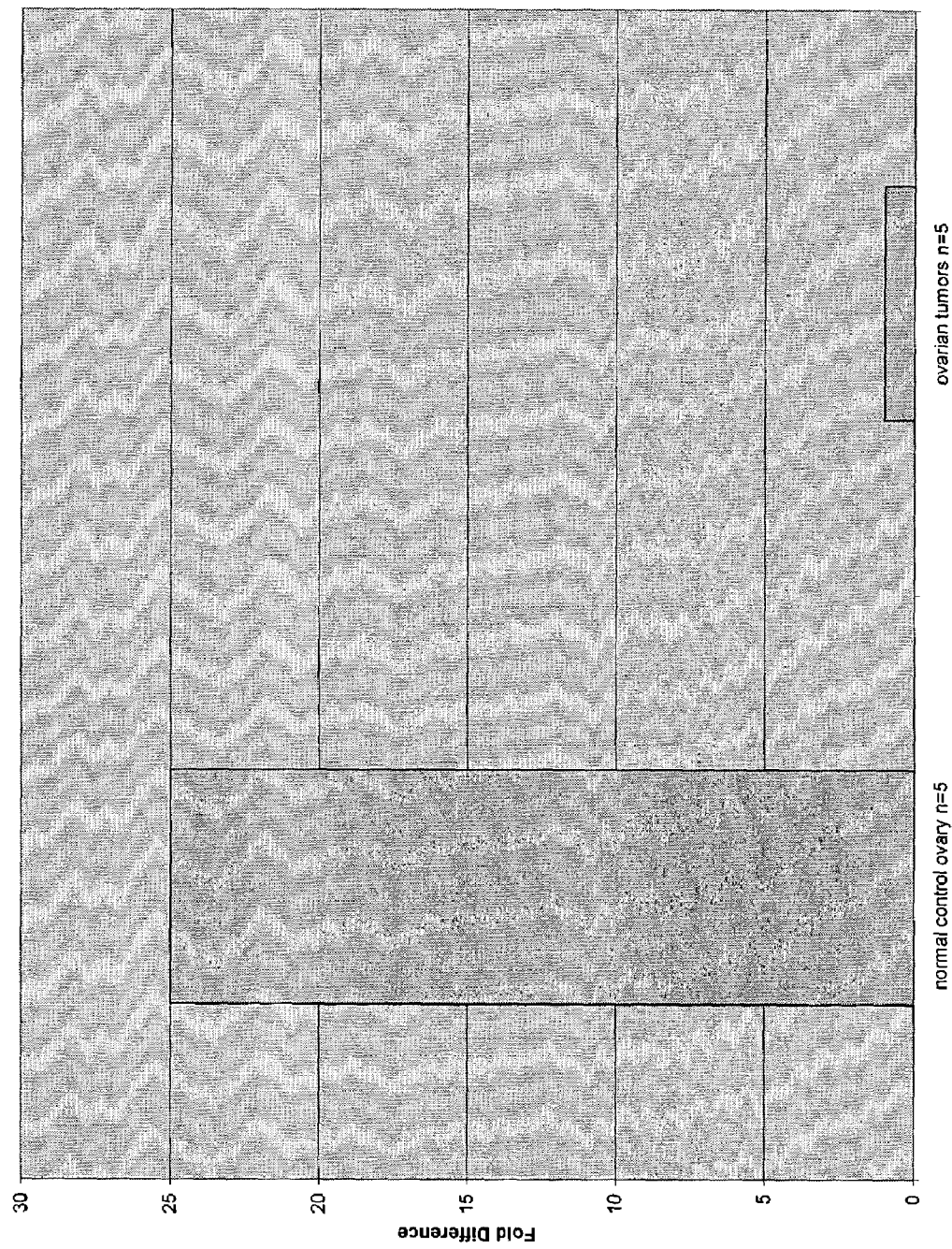
FIG. 8 shows an expanded expression profile of the novel human cell surface protein with immunoglobulin folds, BGS-19, of the present invention. The figure illustrates the relative expression level of BGS-19 amongst various mRNA tissue sources isolated from normal and tumor tissues. As shown, the BGS-19 polypeptide was differentially expressed in ovarian cancer tissue compared to its respective normal tissue. Expression data was obtained by measuring the steady state BGS-19 mRNA levels by quantitative PCR using the PCR primer pair provided as SEQ ID NO:85 and 86, and Taqman probe (SEQ ID NO:87) as described herein.

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The expanded expression profile of the BGS-19 polypeptide is provided in FIGS. 7 and 8, and described elsewhere herein.

Example 8

Method of Creating N- and C-Terminal Deletion Mutants Corresponding to the BGS-19 Polypeptide of the Present Invention As described elsewhere herein, the present invention encompasses the creation of N- and C-terminal deletion mutants, in addition to any combination of N- and C-terminal deletions thereof, corresponding to the BGS-19 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length BGS-19 polypeptide sequence (as described in herein), appropriate primers of about 15–25 nucleotides derived from the desired 5' and 3' positions of SEQ ID NO:1 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the L16 to K385 N-terminal deletion mutant, the following primers could be used to amplify a cDNA fragment corresponding to this deletion mutant:

```
5' Primer 5'-GCAGCA GCGGCCGC CTGAACAAGGATCCCAGTTACAGTC-3'    (SEQ ID NO:82)
                   NotI 3' Primer 5'-GCAGCA GTCGAC CTTTGGAACCATCCCTGACATCTCC-3'     (SEQ ID NO:83)
                   SalI
```

For example, in the case of the M1 to E228 C-terminal deletion mutant, the following primers could be used to amplify a cDNA fragment corresponding to this deletion mutant:

```
5' Primer 5'-GCAGCA GCGGCCGC ATGCTGCTGCTGCCCCTGCTGCTGC-3'   (SEQ ID NO:84)
                   NotI 3' Primer 5'-GCAGCA GTCGAC CTGGGAGCCCAGAGGGTGCTGAGCG-3'    (SEQ ID NO:85)
                   SalI
```

Representative PCR amplification conditions are provided below, although the skilled artisan would appreciate that other conditions may be required for efficient amplification. A 100 ul PCR reaction mixture may be prepared using long of the template DNA (cDNA clone of BGS-19), 200 uM 4 dNTPs, 1 uM primers, 0.25U Taq DNA polymerase (PE), and standard Taq DNA polymerase buffer. Typical PCR cycling condition are as follows:

| 20–25 cycles: | 45 sec, 93 degrees |
|  | 2 min, 50 degrees |
|  | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E.coli cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the BGS-19 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))−25), wherein 'S' is equal to the nucleotide position of the initiating start codon of the BGS-19 gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 9

Method of Enhancing the Biological Activity/ Functional Characteristics of Invention Through Molecular Evolution Although many of the most biologically active proteins known are highly effective for their specified function in an organism, they often possess characteristics that make them undesirable for transgenic, therapeutic, pharmaceutical, and/ or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/ inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered immunoglobulin domain containing protein may be constitutively active upon binding of its cognate ligand. Alternatively, an engineered immunoglobulin domain containing protein may be constitutively active in the absence of ligand binding. In yet another example, an engineered immunoglobulin domain containing protein may be capable of being activated with less than all of the regulatory factors and/or conditions typically required for immunoglobulin domain containing protein activation (e.g., ligand binding, phosphorylation, conformational changes, etc.). Such immunoglobulin domain containing proteins would be useful in screens to identify immunoglobulin domain containing protein modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as descibed by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridation sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with .0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatman) or could be purified using Microcon concentrators (Amicon) of the appropriate molecular weight cuttoff, or could use oligonucleotide purification columns (Qiagen), in addition to other methods known in the art. If using DE81 ion-exchange paper, the 10–50 bp fragments could be eluted from said paper using 1M NaCL, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris·HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C. for 60 s; 94 C. for 30 s, 50–55 C. for 30 s, and 72 C. for 30 s using 30–45 cycles, followed by 72 C. for 5 min using an MJ Research (Cambridge, Mass.) PTC-150 thermocycler. After the assembly reaction is completed, a 1:40 dilution of the resulting primeness product would then be introduced into a PCR mixture (using the same buffer mixture used for the assembly reaction) containing 0.8 um of each primer and subjecting this mixture to 15 cycles of PCR (using 94 C. for 30 s, 50 C. for 30 s, and 72 C. for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailered to the desired level of mutagenesis using the methods described by Zhao, et al. (Nucl Acid Res., 25(6):1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host, particularly if the polynucleotides and polypeptides provide a therapeutic use. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel varient that provided the desired characteristics.

Likewise, the invention encompasses the application of DNA shuffling technology to the evolution of polynucletotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homolog sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. The forgoing are hereby incorporated in their entirety herein for all purposes.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

Incorporation by Reference

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

Equivalents

Those skilled in the art will recognize, or through routine experimentation, will be able to ascertain many equivalents to the particular embodiments of the invention described herein. The claimed invention intends to encompass all such equivalents.

Having herein above disclosed exemplary embodiments of the present invention, those skilled in the art will recognize that this disclosure is only exemplary such that various alternatives, adaptations, and modifications are within the scope of the invention, and are contemplated by the Applicants. Accordingly, the present invention is not limited to the specific embodiments as illustrated above, but is defined by the following claims.

What is claimed is:

1. An isolated nucleic acid molecule comprising a polynucleotide sequence selected from the group consisting of:
   (a) an isolated polynucleotide encoding a polypeptide comprising amino acids 1 to 385 of SEQ ID NO:2;
   (b) an isolated polynucleotide encoding a polypeptide comprising amino acids 2 to 385 of SEQ ID NO:2; and
   (c) an isolated polynucleotide encoding a polypeptide comprising amino acids 16 to 385 of SEQ ID NO:2.

2. The isolated nucleic acid molecule of claim 1, wherein said polynucleotide is (a).

3. The isolated nucleic acid molecule of claim 2, wherein said polynucleotide comprises nucleotides 140 to 1294 of SEQ ID NO:1.

4. The isolated nucleic acid molecule of claim 1, wherein said polynucleotide is (b).

5. The isolated nucleic acid molecule of claim 4, wherein said polynucleotide comprises nucleotides 143 to 1294 of SEQ ID NO:1.

6. The isolated nucleic acid molecule of claim 1, wherein said polynucleotide is (c).

7. The isolated nucleic acid molecule of claim 6, wherein said polynucleotide comprises nucleotides 185 to 1294 of SEQ ID NO:1.

8. A recombinant vector comprising the isolated nucleic acid molecule of claim 1.

9. An isolated recombinant host cell comprising the vector of claim 8.

10. A method of making an isolated polypeptide comprising:
   (a) culturing the isolated recombinant host cell of claim 9 under conditions such that said polypeptide is expressed; and
   (b) recovering said polypeptide.

11. An isolated nucleic acid molecule comprising the cDNA clone contained in plasmid BGS-19 in ATCC Deposit No. PTA-3949.

12. An isolated polynucleotide which represents the complementary sequence of (a), (b), or (c) of claim 1.

* * * * *

UNITED STATES PATENT AND TRADEMARK OFFICE
CERTIFICATE OF CORRECTION

PATENT NO.         : 7,202,056 B2                                                Page 1 of 1
APPLICATION NO. : 10/403938
DATED              : April 10, 2007
INVENTOR(S)        : Liana M. Lee et al.

It is certified that error appears in the above-identified patent and that said Letters Patent is hereby corrected as shown below:

On title page
Item 75 - Inventors
   Jian Chen should be deleted

Signed and Sealed this

Twelfth Day of June, 2007

JON W. DUDAS
*Director of the United States Patent and Trademark Office*

SEQUENCE LISTING

<160> NUMBER OF SEQ ID NOS: 88
<210> SEQ ID NO 1

-continued

```
<211> LENGTH: 1985
<212> TYPE: DNA
<213> ORGANISM: Homo sapiens
<220> FEATURE:
<221> NAME/KEY: CDS
<222> LOCATION: (140)..(1294)

<400> SEQUENCE: 1
cggacgcgtg ggcgaggctc ctcctctgtg gatggtcact gcccctccac caggcttcct      60
gctggaggag tttccttccc agccaggccg gcccagaagc cagatggtcc cggacaggc     120 ccagccccag agcccagag atg ctg ctg ctg ccc ctg ctg ctg ccc gtg ctg     172
                     Met Leu Leu Leu Pro Leu Leu Leu Pro Val Leu
                      1               5                   10 ggg gcg ggg tcc ctg aac aag gat ccc agt tac agt ctt caa gtg cag      220
Gly Ala Gly Ser Leu Asn Lys Asp Pro Ser Tyr Ser Leu Gln Val Gln
            15                  20                  25 agg cag gtg ccg gtg ccg gag ggc ctg tgt gtc atc gtg tct tgc aac      268
Arg Gln Val Pro Val Pro Glu Gly Leu Cys Val Ile Val Ser Cys Asn
 30                  35                  40 ctc tcc tac ccc cgg gat ggc tgg gac gag tct act gct gct tat ggc      316
Leu Ser Tyr Pro Arg Asp Gly Trp Asp Glu Ser Thr Ala Ala Tyr Gly
 45                  50                  55 tac tgg ttc aaa gga cgg acc agc cca aag acg ggt gct cct gtg gcc      364
Tyr Trp Phe Lys Gly Arg Thr Ser Pro Lys Thr Gly Ala Pro Val Ala
 60                  65                  70                  75 act aac aac cag agt cga gag gtg gaa atg agc acc cgg gac cga ttc      412
Thr Asn Asn Gln Ser Arg Glu Val Glu Met Ser Thr Arg Asp Arg Phe
                 80                  85                  90 cag ctc act ggg gat ccc ggc aaa ggg agc tgc tcc ttg gtg atc aga      460
Gln Leu Thr Gly Asp Pro Gly Lys Gly Ser Cys Ser Leu Val Ile Arg
             95                 100                 105 gac gcg cag agg gag gat gag gca tgg tac ttc ttt cgg gtg gag aga      508
Asp Ala Gln Arg Glu Asp Glu Ala Trp Tyr Phe Phe Arg Val Glu Arg
        110                 115                 120 gga agc cgt gtg aga cat agt ttc ctg agc aat gcg ttc ttt cta aaa      556
Gly Ser Arg Val Arg His Ser Phe Leu Ser Asn Ala Phe Phe Leu Lys
    125                 130                 135 gta aca gcc ctg act aag aag cct gat gtc tac atc ccc gag acc ctg      604
Val Thr Ala Leu Thr Lys Lys Pro Asp Val Tyr Ile Pro Glu Thr Leu
140                 145                 150                 155 gag ccc ggg cag ccg gtg acg gtc atc tgt gtg ttt aac tgg gct ttc      652
Glu Pro Gly Gln Pro Val Thr Val Ile Cys Val Phe Asn Trp Ala Phe
                160                 165                 170 aag aaa tgt cca gcc cct tct ttc tcc tgg acg ggg gct gcc ctc tcc      700
Lys Lys Cys Pro Ala Pro Ser Phe Ser Trp Thr Gly Ala Ala Leu Ser
            175                 180                 185 cct aga aga acc aga cca agc acc tcc cag ccc tca gac ccc ggg gtc      748
Pro Arg Arg Thr Arg Pro Ser Thr Ser Gln Pro Ser Asp Pro Gly Val
        190                 195                 200 ctg gag ctg cca ccc att caa atg gag cac gaa gga gag ttc acc tgc      796
Leu Glu Leu Pro Pro Ile Gln Met Glu His Glu Gly Glu Phe Thr Cys
    205                 210                 215 cac gct cag cac cct ctg ggc tcc cag cac gtc tct ctc agc ctc tcc      844
His Ala Gln His Pro Leu Gly Ser Gln His Val Ser Leu Ser Leu Ser
220                 225                 230                 235 gtg cac tgg aag ctg gag cat ggg gga gga ctt ggc ctg ggg gct gcc      892
Val His Trp Lys Leu Glu His Gly Gly Gly Leu Gly Leu Gly Ala Ala
                240                 245                 250 ctg gga gct ggc gtc gct gcc ctg ctc gct ttc tgt tcc tgc ctt gtc      940
Leu Gly Ala Gly Val Ala Ala Leu Leu Ala Phe Cys Ser Cys Leu Val
```

```
                    255                 260                 265
gtc ttc agg gtg aag atc tgc agg aag gaa gct cgc aag agg gca gca         988
Val Phe Arg Val Lys Ile Cys Arg Lys Glu Ala Arg Lys Arg Ala Ala
            270                 275                 280 gct gag cag gac gtg ccc tcc acc ctg gga ccc atc tcc cag ggt cac        1036
Ala Glu Gln Asp Val Pro Ser Thr Leu Gly Pro Ile Ser Gln Gly His
285                 290                 295 cag cat gaa tgc tcg gca ggc agc tcc caa gac cac ccg ccc cca ggt        1084
Gln His Glu Cys Ser Ala Gly Ser Ser Gln Asp His Pro Pro Pro Gly
300                 305                 310                 315 gca gcc acc tac acc ccg ggg aag ggg gaa gag cag gag ctc cac tat        1132
Ala Ala Thr Tyr Thr Pro Gly Lys Gly Glu Glu Gln Glu Leu His Tyr
                320                 325                 330 gcc tcc ctc agc ttc cag ggc ctg agg ctc tgg gag cct gcg gac cag        1180
Ala Ser Leu Ser Phe Gln Gly Leu Arg Leu Trp Glu Pro Ala Asp Gln
                335                 340                 345 gag gcc ccc agc acc acc gag tac tcg gag atc aag atc cac aca gga        1228
Glu Ala Pro Ser Thr Thr Glu Tyr Ser Glu Ile Lys Ile His Thr Gly
            350                 355                 360 cag ccc ctg agg ggc cca ggc ttt ggg ctt caa ttg gag agg gag atg        1276
Gln Pro Leu Arg Gly Pro Gly Phe Gly Leu Gln Leu Glu Arg Glu Met
365                 370                 375 tca ggg atg gtt cca aag tgaagaggtc tccatggcaa caggacacca              1324
Ser Gly Met Val Pro Lys
380                 385 gcaagtgtgt gggagtcgca ctggtgtgac ggccagaact ggactcagat ttcagcccca     1384
tccccaatga agagcttgag tttgaagatt atactttttt tgagacaggg tctgactctg     1444
tcctccaggc cggagtccag tggtgcaatc tcggctcact gtagcctcaa cctgccgggt     1504
tgaagtgagc ctcccatttc agcctcccaa gtagctggga ctacaattgt gagccaccat     1564
gccaggctca ttgttgtatt tttggtagag acggggtttt gccatgtttc cctggctggt     1624
ctcagactcc tgggctcaag caatctgccc gcctctgcct cccagggtgc tgggattgca     1684
gacgtgagcc accacagctg gctgaagatt atactttcaa ttcagagcga gtttgaagat     1744
gacactttga ggcatcgtgt ctatggttca ttactacaga agcttctctg gatgtgtaaa     1804
gcacaggaaa ccaggcagag gaggcacagg gtgctctcca gaacgagaag ccagctcctg     1864
gagttgtttg ctgcaactgc cattccccgt tgatgaccat gctcttcctt cagaagaggg     1924
agagtgagag gaccaagtcc aagtggttcc catttgaaca tttaaaaaaa aaaaaaaaa      1984 g                                                                      1985
```

<210> SEQ ID NO 2
<211> LENGTH: 385
<212> TYPE: PRT
<213> ORGANISM: Homo sapiens

<400> SEQUENCE: 2

```
Met Leu Leu Leu Pro Leu Leu Pro Val Leu Gly Ala Gly Ser Leu
1               5                   10                  15

Asn Lys Asp Pro Ser Tyr Ser Leu Gln Val Gln Arg Gln Val Pro Val
                20                  25                  30

Pro Glu Gly Leu Cys Val Ile Val Ser Cys Asn Leu Ser Tyr Pro Arg
            35                  40                  45

Asp Gly Trp Asp Glu Ser Thr Ala Ala Tyr Gly Tyr Trp Phe Lys Gly
        50                  55                  60
```

```
Arg Thr Ser Pro Lys Thr Gly Ala Pro Val Ala Thr Asn Asn Gln Ser
 65                  70                  75                  80

Arg Glu Val Glu Met Ser Thr Arg Asp Arg Phe Gln Leu Thr Gly Asp
                 85                  90                  95

Pro Gly Lys Gly Ser Cys Ser Leu Val Ile Arg Asp Ala Gln Arg Glu
            100                 105                 110

Asp Glu Ala Trp Tyr Phe Phe Arg Val Glu Arg Gly Ser Arg Val Arg
            115                 120                 125

His Ser Phe Leu Ser Asn Ala Phe Phe Leu Lys Val Thr Ala Leu Thr
130                 135                 140

Lys Lys Pro Asp Val Tyr Ile Pro Glu Thr Leu Glu Pro Gly Gln Pro
145                 150                 155                 160

Val Thr Val Ile Cys Val Phe Asn Trp Ala Phe Lys Lys Cys Pro Ala
                165                 170                 175

Pro Ser Phe Ser Trp Thr Gly Ala Ala Leu Ser Pro Arg Arg Thr Arg
            180                 185                 190

Pro Ser Thr Ser Gln Pro Ser Asp Pro Gly Val Leu Glu Leu Pro Pro
            195                 200                 205

Ile Gln Met Glu His Glu Gly Glu Phe Thr Cys His Ala Gln His Pro
210                 215                 220

Leu Gly Ser Gln His Val Ser Leu Ser Leu Ser Val His Trp Lys Leu
225                 230                 235                 240

Glu His Gly Gly Gly Leu Gly Leu Gly Ala Ala Leu Gly Ala Gly Val
                245                 250                 255

Ala Ala Leu Leu Ala Phe Cys Ser Cys Leu Val Val Phe Arg Val Lys
            260                 265                 270

Ile Cys Arg Lys Glu Ala Arg Lys Arg Ala Ala Ala Glu Gln Asp Val
            275                 280                 285

Pro Ser Thr Leu Gly Pro Ile Ser Gln Gly His Gln His Glu Cys Ser
290                 295                 300

Ala Gly Ser Ser Gln Asp His Pro Pro Gly Ala Ala Thr Tyr Thr
305                 310                 315                 320

Pro Gly Lys Gly Glu Glu Gln Glu Leu His Tyr Ala Ser Leu Ser Phe
                325                 330                 335

Gln Gly Leu Arg Leu Trp Glu Pro Ala Asp Gln Glu Ala Pro Ser Thr
            340                 345                 350

Thr Glu Tyr Ser Glu Ile Lys Ile His Thr Gly Gln Pro Leu Arg Gly
            355                 360                 365

Pro Gly Phe Gly Leu Gln Leu Glu Arg Glu Met Ser Gly Met Val Pro
370                 375                 380

Lys
385

<210> SEQ ID NO 3
<211> LENGTH: 1632
<212> TYPE: DNA
<213> ORGANISM: Homo sapiens
<220> FEATURE:
<221> NAME/KEY: CDS
<222> LOCATION: (1)..(1632)

<400> SEQUENCE: 3 ggg tcc ctg aac aag gat ccc agt tac agt ctt caa gtg cag agg cag      48
Gly Ser Leu Asn Lys Asp Pro Ser Tyr Ser Leu Gln Val Gln Arg Gln
  1               5                  10                  15 gtg ccg gtg ccg gag ggc ctg tgt gtc atc gtg tct tgc aac ctc tcc      96
```

-continued

| | | |
|---|---|---|
| Val Pro Val Pro Glu Gly Leu Cys Val Ile Val Ser Cys Asn Leu Ser<br>20 25 30 | | |
| tac ccc cgg gat ggc tgg gac gag tct act gct gct tat ggc tac tgg<br>Tyr Pro Arg Asp Gly Trp Asp Glu Ser Thr Ala Ala Tyr Gly Tyr Trp<br>35 40 45 | 144 | |
| ttc aaa gga cgg acc agc cca aag acg ggt gct cct gtg gcc act aac<br>Phe Lys Gly Arg Thr Ser Pro Lys Thr Gly Ala Pro Val Ala Thr Asn<br>50 55 60 | 192 | |
| aac cag agt cga gag gtg gaa atg agc acc cgg gac cga ttc cag ctc<br>Asn Gln Ser Arg Glu Val Glu Met Ser Thr Arg Asp Arg Phe Gln Leu<br>65 70 75 80 | 240 | |
| act ggg gat ccc ggc aaa ggg agc tgc tcc ttg gtg atc aga gac gcg<br>Thr Gly Asp Pro Gly Lys Gly Ser Cys Ser Leu Val Ile Arg Asp Ala<br>85 90 95 | 288 | |
| cag agg gag gat gag gca tgg tac ttc ttt cgg gtg gag aga gga agc<br>Gln Arg Glu Asp Glu Ala Trp Tyr Phe Phe Arg Val Glu Arg Gly Ser<br>100 105 110 | 336 | |
| cgt gtg aga cat agt ttc ctg agc aat gcg ttc ttt cta aaa gta aca<br>Arg Val Arg His Ser Phe Leu Ser Asn Ala Phe Phe Leu Lys Val Thr<br>115 120 125 | 384 | |
| gcc ctg act aag aag cct gat gtc tac atc ccc gag acc ctg gag ccc<br>Ala Leu Thr Lys Lys Pro Asp Val Tyr Ile Pro Glu Thr Leu Glu Pro<br>130 135 140 | 432 | |
| ggg cag ccg gtg acg gtc atc tgt gtg ttt aac tgg gct ttc aag aaa<br>Gly Gln Pro Val Thr Val Ile Cys Val Phe Asn Trp Ala Phe Lys Lys<br>145 150 155 160 | 480 | |
| tgt cca gcc cct tct ttc tcc tgg acg ggg gct gcc ctc tcc cct aga<br>Cys Pro Ala Pro Ser Phe Ser Trp Thr Gly Ala Ala Leu Ser Pro Arg<br>165 170 175 | 528 | |
| aga acc aga cca agc acc tcc cac ttc tca gtg ctc agc ttc acg ccc<br>Arg Thr Arg Pro Ser Thr Ser His Phe Ser Val Leu Ser Phe Thr Pro<br>180 185 190 | 576 | |
| agc ccc cag gac cac gac acc gac ctc acc tgc cat gtg gac ttc tcc<br>Ser Pro Gln Asp His Asp Thr Asp Leu Thr Cys His Val Asp Phe Ser<br>195 200 205 | 624 | |
| aga aag ggt gtg agc gca cag agg acc gtc cga ctc cgt gtg gcc tcc<br>Arg Lys Gly Val Ser Ala Gln Arg Thr Val Arg Leu Arg Val Ala Ser<br>210 215 220 | 672 | |
| ctg agc tgc acg tcg att ctg cct ctt cct tcc cta gtc ctg gaa aac<br>Leu Ser Cys Thr Ser Ile Leu Pro Leu Pro Ser Leu Val Leu Glu Asn<br>225 230 235 240 | 720 | |
| ctc ggg aac ggc aca tcc ctc ccg gtc ctg gag ggc caa agc ctg cgc<br>Leu Gly Asn Gly Thr Ser Leu Pro Val Leu Glu Gly Gln Ser Leu Arg<br>245 250 255 | 768 | |
| ctg gtc tgt gtc acc cac agc agc ccc cca gcc agg ctg agc tgg acc<br>Leu Val Cys Val Thr His Ser Ser Pro Pro Ala Arg Leu Ser Trp Thr<br>260 265 270 | 816 | |
| cgg tgg gga cag acc gtg ggc ccc tcc cag ccc tca gac ccc ggg gtc<br>Arg Trp Gly Gln Thr Val Gly Pro Ser Gln Pro Ser Asp Pro Gly Val<br>275 280 285 | 864 | |
| ctg gag ctg cca ccc att caa atg gag cac gaa gga gag ttc acc tgc<br>Leu Glu Leu Pro Pro Ile Gln Met Glu His Glu Gly Glu Phe Thr Cys<br>290 295 300 | 912 | |
| cac gct cag cac cct ctg ggc tcc cag cac gtc tct ctc agc ctc tcc<br>His Ala Gln His Pro Leu Gly Ser Gln His Val Ser Leu Ser Leu Ser<br>305 310 315 320 | 960 | |
| gtg cac tac cct cca cag ctg ctg ggc ccc tcc tgc tcc tgg gag gct<br>Val His Tyr Pro Pro Gln Leu Leu Gly Pro Ser Cys Ser Trp Glu Ala<br>325 330 335 | 1008 | |

```
gag ggt ctg cac tgc agc tgc tcc tcc cag gcc agc ccg gcc ccc tct      1056
Glu Gly Leu His Cys Ser Cys Ser Ser Gln Ala Ser Pro Ala Pro Ser
            340                 345                 350 ctg cgc tgg tgg ctt ggg gag gag ctg ctg gag ggg aac agc agt cag      1104
Leu Arg Trp Trp Leu Gly Glu Glu Leu Leu Glu Gly Asn Ser Ser Gln
        355                 360                 365 ggc tcc ttc gag gtc acc ccc agc tca gcc ggg ccc tgg gcc aac agc      1152
Gly Ser Phe Glu Val Thr Pro Ser Ser Ala Gly Pro Trp Ala Asn Ser
    370                 375                 380 tcc ctg agc ctc cat gga ggg ctc agc tcc ggc ctc agg ctc cgc tgt      1200
Ser Leu Ser Leu His Gly Gly Leu Ser Ser Gly Leu Arg Leu Arg Cys
385                 390                 395                 400 aag gcc tgg aac gtc cac ggg gcc cag agt ggc tct gtc ttc cag ctg      1248
Lys Ala Trp Asn Val His Gly Ala Gln Ser Gly Ser Val Phe Gln Leu
                405                 410                 415 cta cca ggg aag ctg gag cat ggg gga gga ctt ggc ctg ggg gct gcc      1296
Leu Pro Gly Lys Leu Glu His Gly Gly Gly Leu Gly Leu Gly Ala Ala
            420                 425                 430 ctg gga gct ggc gtc gct gcc ctg ctc gct ttc tgt tcc tgc ctt gtc      1344
Leu Gly Ala Gly Val Ala Ala Leu Leu Ala Phe Cys Ser Cys Leu Val
        435                 440                 445 gtc ttc agg aaa tac tca att tcc aga tcc tct tgt gca tcc tcc ttg      1392
Val Phe Arg Lys Tyr Ser Ile Ser Arg Ser Ser Cys Ala Ser Ser Leu
    450                 455                 460 ctc tcg ctt agc ccc cat gac cct aat ttg acc ccc ttt ctc ccc tgc      1440
Leu Ser Leu Ser Pro His Asp Pro Asn Leu Thr Pro Phe Leu Pro Cys
465                 470                 475                 480 att cag ggt cac cag cat gaa tgc tcg gca ggc agc tcc caa gac cac      1488
Ile Gln Gly His Gln His Glu Cys Ser Ala Gly Ser Ser Gln Asp His
                485                 490                 495 ccg ccc cca ggt gca gcc acc tac acc ccg ggg aag ggg gaa gag cag      1536
Pro Pro Pro Gly Ala Ala Thr Tyr Thr Pro Gly Lys Gly Glu Glu Gln
            500                 505                 510 gag ctc cac tat gcc tcc ctc agc ttc cag ggc ctg agg ctc tgg gag      1584
Glu Leu His Tyr Ala Ser Leu Ser Phe Gln Gly Leu Arg Leu Trp Glu
        515                 520                 525 cct gcg gac cag gag gcc ccc agc acc acc gag tac tcg gag atc aag      1632
Pro Ala Asp Gln Glu Ala Pro Ser Thr Thr Glu Tyr Ser Glu Ile Lys
    530                 535                 540
```

<210> SEQ ID NO 4
<211> LENGTH: 544
<212> TYPE: PRT
<213> ORGANISM: Homo sapiens

<400> SEQUENCE: 4

```
Gly Ser Leu Asn Lys Asp Pro Ser Tyr Ser Leu Gln Val Gln Arg Gln
1               5                   10                  15

Val Pro Val Pro Glu Gly Leu Cys Val Ile Val Ser Cys Asn Leu Ser
            20                  25                  30

Tyr Pro Arg Asp Gly Trp Asp Glu Ser Thr Ala Ala Tyr Gly Tyr Trp
        35                  40                  45

Phe Lys Gly Arg Thr Ser Pro Lys Thr Gly Ala Pro Val Ala Thr Asn
    50                  55                  60

Asn Gln Ser Arg Glu Val Glu Met Ser Thr Arg Asp Arg Phe Gln Leu
65                  70                  75                  80

Thr Gly Asp Pro Gly Lys Gly Ser Cys Ser Leu Val Ile Arg Asp Ala
                85                  90                  95

Gln Arg Glu Asp Glu Ala Trp Tyr Phe Phe Arg Val Glu Arg Gly Ser
```

```
                100                 105                 110
Arg Val Arg His Ser Phe Leu Ser Asn Ala Phe Phe Leu Lys Val Thr
            115                 120                 125
Ala Leu Thr Lys Lys Pro Asp Val Tyr Ile Pro Glu Thr Leu Glu Pro
        130                 135                 140
Gly Gln Pro Val Thr Val Ile Cys Val Phe Asn Trp Ala Phe Lys Lys
145                 150                 155                 160
Cys Pro Ala Pro Ser Phe Ser Trp Thr Gly Ala Ala Leu Ser Pro Arg
                165                 170                 175
Arg Thr Arg Pro Ser Thr Ser His Phe Ser Val Leu Ser Phe Thr Pro
            180                 185                 190
Ser Pro Gln Asp His Asp Thr Asp Leu Thr Cys His Val Asp Phe Ser
        195                 200                 205
Arg Lys Gly Val Ser Ala Gln Arg Thr Val Arg Leu Arg Val Ala Ser
210                 215                 220
Leu Ser Cys Thr Ser Ile Leu Pro Leu Pro Ser Leu Val Leu Glu Asn
225                 230                 235                 240
Leu Gly Asn Gly Thr Ser Leu Pro Val Leu Glu Gly Gln Ser Leu Arg
                245                 250                 255
Leu Val Cys Val Thr His Ser Ser Pro Pro Ala Arg Leu Ser Trp Thr
            260                 265                 270
Arg Trp Gly Gln Thr Val Gly Pro Ser Gln Pro Ser Asp Pro Gly Val
        275                 280                 285
Leu Glu Leu Pro Pro Ile Gln Met Glu His Gly Glu Phe Thr Cys
        290                 295                 300
His Ala Gln His Pro Leu Gly Ser Gln His Val Ser Leu Ser Leu Ser
305                 310                 315                 320
Val His Tyr Pro Pro Gln Leu Leu Gly Pro Ser Cys Ser Trp Glu Ala
                325                 330                 335
Glu Gly Leu His Cys Ser Cys Ser Ser Gln Ala Ser Pro Ala Pro Ser
                340                 345                 350
Leu Arg Trp Trp Leu Gly Glu Glu Leu Leu Glu Gly Asn Ser Ser Gln
            355                 360                 365
Gly Ser Phe Glu Val Thr Pro Ser Ser Ala Gly Pro Trp Ala Asn Ser
        370                 375                 380
Ser Leu Ser Leu His Gly Gly Leu Ser Ser Gly Leu Arg Leu Arg Cys
385                 390                 395                 400
Lys Ala Trp Asn Val His Gly Ala Gln Ser Gly Ser Val Phe Gln Leu
                405                 410                 415
Leu Pro Gly Lys Leu Glu His Gly Gly Gly Leu Gly Leu Ala Ala
            420                 425                 430
Leu Gly Ala Gly Val Ala Ala Leu Leu Ala Phe Cys Ser Cys Leu Val
        435                 440                 445
Val Phe Arg Lys Tyr Ser Ile Ser Arg Ser Ser Cys Ala Ser Ser Leu
        450                 455                 460
Leu Ser Leu Ser Pro His Asp Pro Asn Leu Thr Pro Phe Leu Pro Cys
465                 470                 475                 480
Ile Gln Gly His Gln His Glu Cys Ser Ala Gly Ser Ser Gln Asp His
                485                 490                 495
Pro Pro Pro Gly Ala Ala Thr Tyr Thr Pro Gly Lys Gly Glu Glu Gln
            500                 505                 510
Glu Leu His Tyr Ala Ser Leu Ser Phe Gln Gly Leu Arg Leu Trp Glu
            515                 520                 525
```

```
Pro Ala Asp Gln Glu Ala Pro Ser Thr Thr Glu Tyr Ser Glu Ile Lys
    530                 535                 540

<210> SEQ ID NO 5
<211> LENGTH: 364
<212> TYPE: PRT
<213> ORGANISM: Homo sapiens

<400> SEQUENCE: 5

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
50                  55                  60

Ala Ile Ile Ser Gly Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Leu Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Ser Asn Asp Thr His Pro Thr Thr Gly
290                 295                 300

Ser Ala Ser Pro Lys His Gln Lys Asn Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
```

<210> SEQ ID NO 6
<211> LENGTH: 374
<212> TYPE: PRT
<213> ORGANISM: Homo sapiens

<400> SEQUENCE: 6

| | | | | | | | | | | | | | | |
|---|---|---|---|---|---|---|---|---|---|---|---|---|---|---|
| Met | Leu | Leu | Leu | Leu | Leu | Pro | Leu | Leu | Trp | Gly | Arg | Glu | Arg | Val |
| 1 | | | | 5 | | | | | 10 | | | | | 15 |
| Glu | Gly | Gln | Lys | Ser | Asn | Arg | Lys | Asp | Tyr | Ser | Leu | Thr | Met | Gln | Ser |
| | | | 20 | | | | | 25 | | | | | 30 | | |
| Ser | Val | Thr | Val | Gln | Glu | Gly | Met | Cys | Val | His | Val | Arg | Cys | Ser | Phe |
| | | 35 | | | | | 40 | | | | | 45 | | | |
| Ser | Tyr | Pro | Val | Asp | Ser | Gln | Thr | Asp | Ser | Asp | Pro | Val | His | Gly | Tyr |
| | 50 | | | | | 55 | | | | | 60 | | | | |
| Trp | Phe | Arg | Ala | Gly | Asn | Asp | Ile | Ser | Trp | Lys | Ala | Pro | Val | Ala | Thr |
| 65 | | | | | 70 | | | | | 75 | | | | | 80 |
| Asn | Asn | Pro | Ala | Trp | Ala | Val | Gln | Glu | Glu | Thr | Arg | Asp | Arg | Phe | His |
| | | | | 85 | | | | | 90 | | | | | 95 | |
| Leu | Leu | Gly | Asp | Pro | Gln | Thr | Lys | Asn | Cys | Thr | Leu | Ser | Ile | Arg | Asp |
| | | | | 100 | | | | | 105 | | | | | 110 | |
| Ala | Arg | Met | Ser | Asp | Ala | Gly | Arg | Tyr | Phe | Phe | Arg | Met | Glu | Lys | Gly |
| | | 115 | | | | | 120 | | | | | 125 | | | |
| Asn | Ile | Lys | Trp | Asn | Tyr | Lys | Tyr | Asp | Gln | Leu | Ser | Val | Asn | Val | Thr |
| | 130 | | | | | 135 | | | | | 140 | | | | |
| Asp | Pro | Pro | Gln | Asn | Leu | Thr | Val | Thr | Val | Phe | Gln | Gly | Glu | Gly | Thr |
| 145 | | | | | 150 | | | | | 155 | | | | | 160 |
| Ala | Ser | Thr | Ala | Leu | Gly | Asn | Ser | Ser | Leu | Ser | Val | Leu | Glu | Gly |
| | | | | 165 | | | | | 170 | | | | | 175 |
| Gln | Ser | Leu | Arg | Leu | Val | Cys | Ala | Val | Asp | Ser | Asn | Pro | Pro | Ala | Arg |
| | | | 180 | | | | | 185 | | | | | 190 | | |
| Leu | Ser | Trp | Thr | Trp | Arg | Ser | Leu | Thr | Leu | Tyr | Pro | Ser | Gln | Pro | Ser |
| | | | | 195 | | | | | 200 | | | | | 205 | |
| Asn | Pro | Leu | Val | Leu | Glu | Leu | Gln | Val | His | Leu | Gly | Asp | Glu | Gly | Glu |
| | 210 | | | | | 215 | | | | | 220 | | | | |
| Phe | Thr | Cys | Arg | Ala | Gln | Asn | Ser | Leu | Gly | Ser | Gln | His | Val | Ser | Leu |
| 225 | | | | | 230 | | | | | 235 | | | | | 240 |
| Asn | Leu | Ser | Leu | Gln | Gln | Glu | Tyr | Thr | Gly | Lys | Met | Arg | Pro | Val | Ser |
| | | | | 245 | | | | | 250 | | | | | 255 | |
| Gly | Val | Leu | Leu | Gly | Ala | Val | Gly | Gly | Ala | Gly | Ala | Thr | Ala | Leu | Val |
| | | | 260 | | | | | 265 | | | | | 270 | | |
| Phe | Leu | Ser | Phe | Cys | Val | Ile | Phe | Ile | Val | Val | Arg | Ser | Cys | Arg | Lys |
| | | 275 | | | | | 280 | | | | | 285 | | | |
| Lys | Ser | Ala | Arg | Pro | Ala | Ala | Asp | Val | Gly | Asp | Ile | Gly | Met | Lys | Asp |
| | 290 | | | | | 295 | | | | | 300 | | | | |
| Ala | Asn | Thr | Ile | Arg | Gly | Ser | Ala | Ser | Gln | Gly | Asn | Leu | Thr | Glu | Ser |
| 305 | | | | | 310 | | | | | 315 | | | | | 320 |
| Trp | Ala | Asp | Asp | Asn | Pro | Arg | His | His | Gly | Leu | Ala | Ala | His | Ser | Ser |
| | | | | 325 | | | | | 330 | | | | | 335 | |
| Gly | Glu | Glu | Arg | Glu | Ile | Gln | Tyr | Ala | Pro | Leu | Ser | Phe | His | Lys | Gly |
| | | | 340 | | | | | 345 | | | | | 350 | | |
| Glu | Pro | Gln | Asp | Leu | Ser | Gly | Gln | Glu | Ala | Thr | Asn | Asn | Glu | Tyr | Ser |
| | | 355 | | | | | 360 | | | | | 365 | | | |

Glu Ile Lys Ile Pro Lys
        370

<210> SEQ ID NO 7
<211> LENGTH: 697
<212> TYPE: PRT
<213> ORGANISM: Homo sapiens

<400> SEQUENCE: 7

Met Leu Pro Leu Leu Ser Ser Leu Gly Gly Ser Gln Ala
1               5                   10                  15

Met Asp Gly Arg Phe Trp Ile Arg Val Gln Glu Ser Val Met Val Pro
            20                  25                  30

Glu Gly Leu Cys Ile Ser Val Pro Cys Ser Phe Ser Tyr Pro Arg Gln
                35                  40                  45

Asp Trp Thr Gly Ser Thr Pro Ala Tyr Gly Tyr Trp Phe Lys Ala Val
        50                  55                  60

Thr Glu Thr Thr Lys Gly Ala Pro Val Ala Thr Asn His Gln Ser Arg
65                  70                  75                  80

Glu Val Glu Met Ser Thr Arg Gly Arg Phe Gln Leu Thr Gly Asp Pro
                85                  90                  95

Ala Lys Gly Asn Cys Ser Leu Val Ile Arg Asp Ala Gln Met Gln Asp
            100                 105                 110

Glu Ser Gln Tyr Phe Phe Arg Val Glu Arg Gly Ser Tyr Val Arg Tyr
        115                 120                 125

Asn Phe Met Asn Asp Gly Phe Phe Leu Lys Val Thr Ala Leu Thr Gln
    130                 135                 140

Lys Pro Asp Val Tyr Ile Pro Glu Thr Leu Glu Pro Gly Gln Pro Val
145                 150                 155                 160

Thr Val Ile Cys Val Phe Asn Trp Ala Phe Glu Glu Cys Pro Pro Pro
                165                 170                 175

Ser Phe Ser Trp Thr Gly Ala Ala Leu Ser Ser Gln Gly Thr Lys Pro
            180                 185                 190

Thr Thr Ser His Phe Ser Val Leu Ser Phe Thr Pro Arg Pro Gln Asp
        195                 200                 205

His Asn Thr Asp Leu Thr Cys His Val Asp Phe Ser Arg Lys Gly Val
    210                 215                 220

Ser Val Gln Arg Thr Val Arg Leu Arg Val Ala Tyr Ala Pro Arg Asp
225                 230                 235                 240

Leu Val Ile Ser Ile Ser Arg Asp Asn Thr Pro Ala Leu Glu Pro Gln
                245                 250                 255

Pro Gln Gly Asn Val Pro Tyr Leu Glu Ala Gln Lys Gly Gln Phe Leu
            260                 265                 270

Arg Leu Leu Cys Ala Ala Asp Ser Gln Pro Pro Ala Thr Leu Ser Trp
        275                 280                 285

Val Leu Gln Asn Arg Val Leu Ser Ser Ser His Pro Trp Gly Pro Arg
    290                 295                 300

Pro Leu Gly Leu Glu Leu Pro Gly Val Lys Ala Gly Asp Ser Gly Arg
305                 310                 315                 320

Tyr Thr Cys Arg Ala Glu Asn Arg Leu Gly Ser Gln Arg Ala Leu
                325                 330                 335

Asp Leu Ser Val Gln Tyr Pro Pro Glu Asn Leu Arg Val Met Val Ser
            340                 345                 350

Gln Ala Asn Arg Thr Val Leu Glu Asn Leu Gly Asn Gly Thr Ser Leu
        355                 360                 365

-continued

```
Pro Val Leu Glu Gly Gln Ser Leu Cys Leu Val Cys Val Thr His Ser
    370                 375                 380

Ser Pro Pro Ala Arg Leu Ser Trp Thr Gln Arg Gly Gln Val Leu Ser
385                 390                 395                 400

Pro Ser Gln Pro Ser Asp Pro Gly Val Leu Glu Leu Pro Arg Val Gln
                405                 410                 415

Val Glu His Glu Gly Glu Phe Thr Cys His Ala Arg His Pro Leu Gly
                420                 425                 430

Ser Gln His Val Ser Leu Ser Leu Ser Val His Tyr Ser Pro Lys Leu
            435                 440                 445

Leu Gly Pro Ser Cys Ser Trp Glu Ala Glu Gly Leu His Cys Ser Cys
    450                 455                 460

Ser Ser Gln Ala Ser Pro Ala Pro Ser Leu Arg Trp Trp Leu Gly Glu
465                 470                 475                 480

Glu Leu Leu Glu Gly Asn Ser Ser Gln Asp Ser Phe Glu Val Thr Pro
                485                 490                 495

Ser Ser Ala Gly Pro Trp Ala Asn Ser Ser Leu Ser Leu His Gly Gly
            500                 505                 510

Leu Ser Ser Gly Leu Arg Leu Arg Cys Glu Ala Trp Asn Val His Gly
    515                 520                 525

Ala Gln Ser Gly Ser Ile Leu Gln Leu Pro Asp Lys Lys Gly Leu Ile
530                 535                 540

Ser Thr Ala Phe Ser Asn Gly Ala Phe Leu Gly Ile Gly Ile Thr Ala
545                 550                 555                 560

Leu Leu Phe Leu Cys Leu Ala Leu Ile Ile Met Lys Ile Leu Pro Lys
                565                 570                 575

Arg Arg Thr Gln Thr Glu Thr Pro Arg Pro Arg Phe Ser Arg His Ser
            580                 585                 590

Thr Ile Leu Asp Tyr Ile Asn Val Val Pro Thr Ala Gly Pro Leu Ala
    595                 600                 605

Gln Lys Arg Asn Gln Lys Ala Thr Pro Asn Ser Pro Arg Thr Pro Leu
610                 615                 620

Pro Pro Gly Ala Pro Ser Pro Glu Ser Lys Lys Asn Gln Lys Lys Gln
625                 630                 635                 640

Tyr Gln Leu Pro Ser Phe Pro Glu Pro Lys Ser Thr Gln Ala Pro
                645                 650                 655

Glu Ser Gln Glu Ser Gln Glu Glu Leu His Tyr Ala Thr Leu Asn Phe
            660                 665                 670

Pro Gly Val Arg Pro Arg Pro Glu Ala Arg Met Pro Lys Gly Thr Gln
    675                 680                 685

Ala Asp Tyr Ala Glu Val Lys Phe Gln
    690                 695

<210> SEQ ID NO 8
<211> LENGTH: 26
<212> TYPE: PRT
<213> ORGANISM: Homo sapiens

<400> SEQUENCE: 8

Ala Ala Leu Gly Ala Gly Val Ala Ala Leu Leu Ala Phe Cys Ser Cys
1               5                   10                  15

Leu Val Val Phe Arg Val Lys Ile Cys Arg
            20                  25
```

```
<210> SEQ ID NO 9
<211> LENGTH: 100
<212> TYPE: PRT
<213> ORGANISM: Homo sapiens

<400> SEQUENCE: 9

Gly Ser Leu Asn Lys Asp Pro Ser Tyr Ser Leu Gln Val Gln Arg Gln
1               5                   10                  15

Val Pro Val Pro Glu Gly Leu Cys Val Ile Val Ser Cys Asn Leu Ser
            20                  25                  30

Tyr Pro Arg Asp Gly Trp Asp Glu Ser Thr Ala Ala Tyr Gly Tyr Trp
        35                  40                  45

Phe Lys Gly Arg Thr Ser Pro Lys Thr Gly Ala Pro Val Ala Thr Asn
    50                  55                  60

Asn Gln Ser Arg Glu Val Glu Met Ser Thr Arg Asp Arg Phe Gln Leu
65                  70                  75                  80

Thr Gly Asp Pro Gly Lys Gly Ser Cys Ser Leu Val Ile Arg Asp Ala
                85                  90                  95

Gln Arg Glu Asp
            100

<210> SEQ ID NO 10
<211> LENGTH: 102
<212> TYPE: PRT
<213> ORGANISM: Homo sapiens

<400> SEQUENCE: 10

Val Thr Ala Leu Thr Lys Lys Pro Asp Val Tyr Ile Pro Glu Thr Leu
1               5                   10                  15

Glu Pro Gly Gln Pro Val Thr Val Ile Cys Val Phe Asn Trp Ala Phe
            20                  25                  30

Lys Lys Cys Pro Ala Pro Ser Phe Ser Trp Thr Gly Ala Ala Leu Ser
        35                  40                  45

Pro Arg Arg Thr Arg Pro Ser Thr Gln Pro Ser Asp Pro Gly Val
    50                  55                  60

Leu Glu Leu Pro Pro Ile Gln Met Glu His Gly Glu Phe Thr Cys
65                  70                  75                  80

His Ala Gln His Pro Leu Gly Ser Gln His Val Ser Leu Ser Leu Ser
                85                  90                  95

Val His Trp Lys Leu Glu
            100

<210> SEQ ID NO 11
<211> LENGTH: 64
<212> TYPE: PRT
<213> ORGANISM: Homo sapiens

<400> SEQUENCE: 11

Met Leu Leu Leu Pro Leu Leu Leu Pro Val Leu Gly Ala Gly Ser Leu
1               5                   10                  15

Asn Lys Asp Pro Ser Tyr Ser Leu Gln Val Gln Arg Gln Val Pro Val
            20                  25                  30

Pro Glu Gly Leu Cys Val Ile Val Ser Cys Asn Leu Ser Tyr Pro Arg
        35                  40                  45

Asp Gly Trp Asp Glu Ser Thr Ala Ala Tyr Gly Tyr Trp Phe Lys Gly
    50                  55                  60

<210> SEQ ID NO 12
```

```
<211> LENGTH: 66
<212> TYPE: PRT
<213> ORGANISM: Homo sapiens

<400> SEQUENCE: 12

Thr Ser Pro Lys Thr Gly Ala Pro Val Ala Thr Asn Asn Gln Ser Arg
1               5                   10                  15

Glu Val Glu Met Ser Thr Arg Asp Arg Phe Gln Leu Thr Gly Asp Pro
            20                  25                  30

Gly Lys Gly Ser Cys Ser Leu Val Ile Arg Asp Ala Gln Arg Glu Asp
        35                  40                  45

Glu Ala Trp Tyr Phe Phe Arg Val Glu Arg Gly Ser Arg Val Arg His
    50                  55                  60

Ser Phe
65

<210> SEQ ID NO 13
<211> LENGTH: 7
<212> TYPE: PRT
<213> ORGANISM: Homo sapiens

<400> SEQUENCE: 13

Leu Lys Val Thr Ala Leu Thr
1               5

<210> SEQ ID NO 14
<211> LENGTH: 13
<212> TYPE: PRT
<213> ORGANISM: Homo sapiens

<400> SEQUENCE: 14

Lys Pro Asp Val Tyr Ile Pro Glu Thr Leu Glu Pro Gly
1               5                   10

<210> SEQ ID NO 15
<211> LENGTH: 68
<212> TYPE: PRT
<213> ORGANISM: Homo sapiens

<400> SEQUENCE: 15

Arg Val Lys Ile Cys Arg Lys Glu Ala Arg Lys Arg Ala Ala Ala Glu
1               5                   10                  15

Gln Asp Val Pro Ser Thr Leu Gly Pro Ile Ser Gln Gly His Gln His
            20                  25                  30

Glu Cys Ser Ala Gly Ser Ser Gln Asp His Pro Pro Gly Ala Ala
        35                  40                  45

Thr Tyr Thr Pro Gly Lys Gly Glu Glu Gln Leu His Tyr Ala Ser
    50                  55                  60

Leu Ser Phe Gln
65

<210> SEQ ID NO 16
<211> LENGTH: 47
<212> TYPE: PRT
<213> ORGANISM: Homo sapiens

<400> SEQUENCE: 16

Gly Leu Arg Leu Trp Glu Pro Ala Asp Gln Glu Ala Pro Ser Thr Thr
1               5                   10                  15

Glu Tyr Ser Glu Ile Lys Ile His Thr Gly Gln Pro Leu Arg Gly Pro
            20                  25                  30
```

```
Gly Phe Gly Leu Gln Leu Glu Arg Glu Met Ser Gly Met Val Pro
        35                  40                  45
```

<210> SEQ ID NO 17
<211> LENGTH: 58
<212> TYPE: PRT
<213> ORGANISM: Homo sapiens

<400> SEQUENCE: 17

```
Arg Val Lys Ile Cys Arg Lys Glu Ala Arg Lys Arg Ala Ala Ala Glu
1               5                   10                  15

Gln Asp Val Pro Ser Thr Leu Gly Pro Ile Ser Gln Gly His Gln His
            20                  25                  30

Glu Cys Ser Ala Gly Ser Ser Gln Asp His Pro Pro Gly Ala Ala
        35                  40                  45

Thr Tyr Thr Pro Gly Lys Gly Glu Glu Gln
    50                  55
```

<210> SEQ ID NO 18
<211> LENGTH: 14
<212> TYPE: PRT
<213> ORGANISM: Homo sapiens

<400> SEQUENCE: 18

```
Gly Pro Gly Phe Gly Leu Gln Leu Glu Arg Glu Met Ser Gly
1               5                   10
```

<210> SEQ ID NO 19
<211> LENGTH: 13
<212> TYPE: PRT
<213> ORGANISM: Homo sapiens

<400> SEQUENCE: 19

```
His Tyr Ala Ser Leu Ser Phe Gln Gly Leu Arg Leu Trp
1               5                   10
```

<210> SEQ ID NO 20
<211> LENGTH: 43
<212> TYPE: PRT
<213> ORGANISM: Homo sapiens

<400> SEQUENCE: 20

```
Arg Val Lys Ile Cys Arg Lys Glu Ala Arg Lys Arg Ala Ala Ala Glu
1               5                   10                  15

Gln Asp Val Pro Ser Thr Leu Gly Pro Ile Ser Gln Gly His Gln His
            20                  25                  30

Glu Cys Ser Ala Gly Ser Ser Gln Asp His Pro
        35                  40
```

<210> SEQ ID NO 21
<211> LENGTH: 7
<212> TYPE: PRT
<213> ORGANISM: Homo sapiens

<400> SEQUENCE: 21

```
Pro Gly Ala Ala Thr Tyr Thr
1               5
```

<210> SEQ ID NO 22
<211> LENGTH: 11
<212> TYPE: PRT
<213> ORGANISM: Homo sapiens -continued

```
<400> SEQUENCE: 22

Gly Lys Gly Glu Glu Gln Glu Leu His Tyr Ala
1               5                   10

<210> SEQ ID NO 23
<211> LENGTH: 10
<212> TYPE: PRT
<213> ORGANISM: Homo sapiens

<400> SEQUENCE: 23

Leu Leu Leu Pro Leu Leu Leu Pro Val Leu
1               5                   10

<210> SEQ ID NO 24
<211> LENGTH: 12
<212> TYPE: PRT
<213> ORGANISM: Homo sapiens

<400> SEQUENCE: 24

Met Leu Leu Leu Pro Leu Leu Leu Pro Val Leu Gly
1               5                   10

<210> SEQ ID NO 25
<211> LENGTH: 6
<212> TYPE: PRT
<213> ORGANISM: Homo sapiens

<400> SEQUENCE: 25

Val Pro Glu Gly Leu Cys
1               5

<210> SEQ ID NO 26
<211> LENGTH: 8
<212> TYPE: PRT
<213> ORGANISM: Homo sapiens

<400> SEQUENCE: 26

Pro Val Pro Glu Gly Leu Cys Val
1               5

<210> SEQ ID NO 27
<211> LENGTH: 7
<212> TYPE: PRT
<213> ORGANISM: Homo sapiens

<400> SEQUENCE: 27

Ala Tyr Gly Tyr Trp Phe Lys
1               5

<210> SEQ ID NO 28
<211> LENGTH: 9
<212> TYPE: PRT
<213> ORGANISM: Homo sapiens

<400> SEQUENCE: 28

Ala Ala Tyr Gly Tyr Trp Phe Lys Gly
1               5

<210> SEQ ID NO 29
<211> LENGTH: 7
<212> TYPE: PRT
<213> ORGANISM: Homo sapiens

<400> SEQUENCE: 29
```

```
Gly Ala Pro Val Ala Thr Asn
1               5

<210> SEQ ID NO 30
<211> LENGTH: 9
<212> TYPE: PRT
<213> ORGANISM: Homo sapiens

<400> SEQUENCE: 30

Thr Gly Ala Pro Val Ala Thr Asn Asn
1               5

<210> SEQ ID NO 31
<211> LENGTH: 19
<212> TYPE: PRT
<213> ORGANISM: Homo sapiens

<400> SEQUENCE: 31

Gly Ala Pro Val Ala Thr Asn Asn Gln Ser Arg Glu Val Glu Met
1               5                   10                  15

Ser Thr Arg

<210> SEQ ID NO 32
<211> LENGTH: 28
<212> TYPE: PRT
<213> ORGANISM: Homo sapiens

<400> SEQUENCE: 32

Gly Ala Pro Val Ala Thr Asn Asn Gln Ser Arg Glu Val Glu Met
1               5                   10                  15

Ser Thr Arg Asp Arg Phe Gln Leu Thr Gly Asp Pro
            20                  25

<210> SEQ ID NO 33
<211> LENGTH: 10
<212> TYPE: PRT
<213> ORGANISM: Homo sapiens

<400> SEQUENCE: 33

Gln Ser Arg Glu Val Glu Met Ser Thr Arg
1               5                   10

<210> SEQ ID NO 34
<211> LENGTH: 12
<212> TYPE: PRT
<213> ORGANISM: Homo sapiens

<400> SEQUENCE: 34

Asn Gln Ser Arg Glu Val Glu Met Ser Thr Arg Asp
1               5                   10

<210> SEQ ID NO 35
<211> LENGTH: 8
<212> TYPE: PRT
<213> ORGANISM: Homo sapiens

<400> SEQUENCE: 35

Arg Phe Gln Leu Thr Gly Asp Pro
1               5

<210> SEQ ID NO 36
<211> LENGTH: 10
<212> TYPE: PRT
```

```
<213> ORGANISM: Homo sapiens

<400> SEQUENCE: 36

Asp Arg Phe Gln Leu Thr Gly Asp Pro Gly
1               5                   10

<210> SEQ ID NO 37
<211> LENGTH: 12
<212> TYPE: PRT
<213> ORGANISM: Homo sapiens

<400> SEQUENCE: 37

Lys Gly Ser Cys Ser Leu Val Ile Arg Asp Ala Gln
1               5                   10

<210> SEQ ID NO 38
<211> LENGTH: 14
<212> TYPE: PRT
<213> ORGANISM: Homo sapiens

<400> SEQUENCE: 38

Gly Lys Gly Ser Cys Ser Leu Val Ile Arg Asp Ala Gln Arg
1               5                   10

<210> SEQ ID NO 39
<211> LENGTH: 9
<212> TYPE: PRT
<213> ORGANISM: Homo sapiens

<400> SEQUENCE: 39

Tyr Phe Phe Arg Val Glu Arg Gly Ser
1               5

<210> SEQ ID NO 40
<211> LENGTH: 11
<212> TYPE: PRT
<213> ORGANISM: Homo sapiens

<400> SEQUENCE: 40

Trp Tyr Phe Phe Arg Val Glu Arg Gly Ser Arg
1               5                   10

<210> SEQ ID NO 41
<211> LENGTH: 9
<212> TYPE: PRT
<213> ORGANISM: Homo sapiens

<400> SEQUENCE: 41

Phe Phe Leu Lys Val Thr Ala Leu Thr
1               5

<210> SEQ ID NO 42
<211> LENGTH: 11
<212> TYPE: PRT
<213> ORGANISM: Homo sapiens

<400> SEQUENCE: 42

Ala Phe Phe Leu Lys Val Thr Ala Leu Thr Lys
1               5                   10

<210> SEQ ID NO 43
<211> LENGTH: 26
<212> TYPE: PRT
<213> ORGANISM: Homo sapiens
```

```
<400> SEQUENCE: 43

Lys Pro Asp Val Tyr Ile Pro Glu Thr Leu Glu Pro Gly Gln Pro Val
1               5                   10                  15

Thr Val Ile Cys Val Phe Asn Trp Ala Phe
            20                  25

<210> SEQ ID NO 44
<211> LENGTH: 28
<212> TYPE: PRT
<213> ORGANISM: Homo sapiens

<400> SEQUENCE: 44

Lys Lys Pro Asp Val Tyr Ile Pro Glu Thr Leu Glu Pro Gly Gln Pro
1               5                   10                  15

Val Thr Val Ile Cys Val Phe Asn Trp Ala Phe Lys
            20                  25

<210> SEQ ID NO 45
<211> LENGTH: 14
<212> TYPE: PRT
<213> ORGANISM: Homo sapiens

<400> SEQUENCE: 45

Cys Pro Ala Pro Ser Phe Ser Trp Thr Gly Ala Ala Leu Ser
1               5                   10

<210> SEQ ID NO 46
<211> LENGTH: 16
<212> TYPE: PRT
<213> ORGANISM: Homo sapiens

<400> SEQUENCE: 46

Lys Cys Pro Ala Pro Ser Phe Ser Trp Thr Gly Ala Ala Leu Ser Pro
1               5                   10                  15

<210> SEQ ID NO 47
<211> LENGTH: 11
<212> TYPE: PRT
<213> ORGANISM: Homo sapiens

<400> SEQUENCE: 47

Pro Ser Phe Ser Trp Thr Gly Ala Ala Leu Ser
1               5                   10

<210> SEQ ID NO 48
<211> LENGTH: 13
<212> TYPE: PRT
<213> ORGANISM: Homo sapiens

<400> SEQUENCE: 48

Ala Pro Ser Phe Ser Trp Thr Gly Ala Ala Leu Ser Pro
1               5                   10

<210> SEQ ID NO 49
<211> LENGTH: 7
<212> TYPE: PRT
<213> ORGANISM: Homo sapiens

<400> SEQUENCE: 49

Pro Pro Ile Gln Met Glu His
1               5

<210> SEQ ID NO 50
```

<211> LENGTH: 8
<212> TYPE: PRT
<213> ORGANISM: Homo sapiens

<400> SEQUENCE: 50

Pro Pro Ile Gln Met Glu His Glu
1               5

<210> SEQ ID NO 51
<211> LENGTH: 9
<212> TYPE: PRT
<213> ORGANISM: Homo sapiens

<400> SEQUENCE: 51

Leu Pro Pro Ile Gln Met Glu His Glu
1               5

<210> SEQ ID NO 52
<211> LENGTH: 12
<212> TYPE: PRT
<213> ORGANISM: Homo sapiens

<400> SEQUENCE: 52

Gly Ala Ala Leu Gly Ala Gly Val Ala Ala Leu Leu
1               5                   10

<210> SEQ ID NO 53
<211> LENGTH: 13
<212> TYPE: PRT
<213> ORGANISM: Homo sapiens

<400> SEQUENCE: 53

Leu Gly Ala Ala Leu Gly Ala Gly Val Ala Ala Leu Leu
1               5                   10

<210> SEQ ID NO 54
<211> LENGTH: 14
<212> TYPE: PRT
<213> ORGANISM: Homo sapiens

<400> SEQUENCE: 54

Leu Gly Ala Ala Leu Gly Ala Gly Val Ala Ala Leu Leu Ala
1               5                   10

<210> SEQ ID NO 55
<211> LENGTH: 9
<212> TYPE: PRT
<213> ORGANISM: Homo sapiens

<400> SEQUENCE: 55

Glu Leu His Tyr Ala Ser Leu Ser Phe
1               5

<210> SEQ ID NO 56
<211> LENGTH: 11
<212> TYPE: PRT
<213> ORGANISM: Homo sapiens

<400> SEQUENCE: 56

Gln Glu Leu His Tyr Ala Ser Leu Ser Phe Gln
1               5                   10

<210> SEQ ID NO 57
<211> LENGTH: 80
<212> TYPE: DNA

```
<213> ORGANISM: Homo sapiens

<400> SEQUENCE: 57
tgggctggtc cgtcctttga accagtagcc ataagcagca gtagactcgt cccagccatc    60
ccgggggtag gagaggttgc                                                80

<210> SEQ ID NO 58
<211> LENGTH: 20
<212> TYPE: DNA
<213> ORGANISM: Bacteriophage T7

<400> SEQUENCE: 58
taatacgact cactataggg                                                20

<210> SEQ ID NO 59
<211> LENGTH: 18
<212> TYPE: DNA
<213> ORGANISM: Bacteriophage SP6

<400> SEQUENCE: 59
atttaggtga cactatag                                                  18

<210> SEQ ID NO 60
<211> LENGTH: 20
<212> TYPE: DNA
<213> ORGANISM: Homo sapiens

<400> SEQUENCE: 60
catcgtgtct tgcaacctct                                                20

<210> SEQ ID NO 61
<211> LENGTH: 20
<212> TYPE: DNA
<213> ORGANISM: Homo sapiens

<400> SEQUENCE: 61
ctctctccac ccgaaagaag                                                20

<210> SEQ ID NO 62
<211> LENGTH: 14
<212> TYPE: PRT
<213> ORGANISM: Homo sapiens

<400> SEQUENCE: 62

Val Ile Val Ser Cys Asn Leu Ser Tyr Pro Arg Asp Gly Trp
1               5                   10

<210> SEQ ID NO 63
<211> LENGTH: 14
<212> TYPE: PRT
<213> ORGANISM: Homo sapiens

<400> SEQUENCE: 63

Pro Val Ala Thr Asn Asn Gln Ser Arg Glu Val Glu Met Ser
1               5                   10

<210> SEQ ID NO 64
<211> LENGTH: 13
<212> TYPE: PRT
<213> ORGANISM: Homo sapiens

<400> SEQUENCE: 64

Phe Lys Gly Arg Thr Ser Pro Lys Thr Gly Ala Pro Val
```

```
                    1               5                    10

<210> SEQ ID NO 65
<211> LENGTH: 13
<212> TYPE: PRT
<213> ORGANISM: Homo sapiens

<400> SEQUENCE: 65

Arg Glu Val Glu Met Ser Thr Arg Asp Arg Phe Gln Leu
1               5                   10

<210> SEQ ID NO 66
<211> LENGTH: 13
<212> TYPE: PRT
<213> ORGANISM: Homo sapiens

<400> SEQUENCE: 66

Lys Val Thr Ala Leu Thr Lys Lys Pro Asp Val Tyr Ile
1               5                   10

<210> SEQ ID NO 67
<211> LENGTH: 13
<212> TYPE: PRT
<213> ORGANISM: Homo sapiens

<400> SEQUENCE: 67

Thr Gly Ala Ala Leu Ser Pro Arg Arg Thr Arg Pro Ser
1               5                   10

<210> SEQ ID NO 68
<211> LENGTH: 17
<212> TYPE: PRT
<213> ORGANISM: Homo sapiens

<400> SEQUENCE: 68

Ile Arg Asp Ala Gln Arg Glu Asp Glu Ala Trp Tyr Phe Phe Arg Val
1               5                   10                  15

Glu

<210> SEQ ID NO 69
<211> LENGTH: 14
<212> TYPE: PRT
<213> ORGANISM: Homo sapiens

<400> SEQUENCE: 69

Arg Glu Val Glu Met Ser Thr Arg Asp Arg Phe Gln Leu Thr
1               5                   10

<210> SEQ ID NO 70
<211> LENGTH: 14
<212> TYPE: PRT
<213> ORGANISM: Homo sapiens

<400> SEQUENCE: 70

Glu Cys Ser Ala Gly Ser Ser Gln Asp His Pro Pro Pro Gly
1               5                   10

<210> SEQ ID NO 71
<211> LENGTH: 14
<212> TYPE: PRT
<213> ORGANISM: Homo sapiens

<400> SEQUENCE: 71

Asp Gln Glu Ala Pro Ser Thr Thr Glu Tyr Ser Glu Ile Lys
```

<210> SEQ ID NO 72
<211> LENGTH: 16
<212> TYPE: PRT
<213> ORGANISM: Homo sapiens

<400> SEQUENCE: 72

Thr Ser Pro Lys Thr Gly Ala Pro Val Ala Thr Asn Asn Gln Ser Arg
1               5                   10                  15

<210> SEQ ID NO 73
<211> LENGTH: 16
<212> TYPE: PRT
<213> ORGANISM: Homo sapiens

<400> SEQUENCE: 73

Glu Thr Leu Glu Pro Gly Gln Pro Val Thr Val Ile Cys Val Phe Asn
1               5                   10                  15

<210> SEQ ID NO 74
<211> LENGTH: 16
<212> TYPE: PRT
<213> ORGANISM: Homo sapiens

<400> SEQUENCE: 74

Trp Lys Leu Glu His Gly Gly Gly Leu Gly Leu Gly Ala Ala Leu Gly
1               5                   10                  15

<210> SEQ ID NO 75
<211> LENGTH: 16
<212> TYPE: PRT
<213> ORGANISM: Homo sapiens

<400> SEQUENCE: 75

Leu Glu His Gly Gly Gly Leu Gly Leu Gly Ala Ala Leu Gly Ala Gly
1               5                   10                  15

<210> SEQ ID NO 76
<211> LENGTH: 16
<212> TYPE: PRT
<213> ORGANISM: Homo sapiens

<400> SEQUENCE: 76

His Gly Gly Gly Leu Gly Leu Gly Ala Ala Leu Gly Ala Gly Val Ala
1               5                   10                  15

<210> SEQ ID NO 77
<211> LENGTH: 16
<212> TYPE: PRT
<213> ORGANISM: Homo sapiens

<400> SEQUENCE: 77

Gly Gly Leu Gly Leu Gly Ala Ala Leu Gly Ala Gly Val Ala Ala Leu
1               5                   10                  15

<210> SEQ ID NO 78
<211> LENGTH: 16
<212> TYPE: PRT
<213> ORGANISM: Homo sapiens

<400> SEQUENCE: 78

Leu Gly Ala Ala Leu Gly Ala Gly Val Ala Ala Leu Leu Ala Phe Cys
1               5                   10                  15

```
<210> SEQ ID NO 79
<211> LENGTH: 17
<212> TYPE: PRT
<213> ORGANISM: Homo sapiens

<400> SEQUENCE: 79

Glu His Glu Gly Glu Phe Thr Cys His Ala Gln His Pro Leu Gly Ser
1               5                  10                  15
Gln

<210> SEQ ID NO 80
<211> LENGTH: 20
<212> TYPE: DNA
<213> ORGANISM: Homo sapiens

<400> SEQUENCE: 80
aagaaccaga ccaagcacct                                              20

<210> SEQ ID NO 81
<211> LENGTH: 20
<212> TYPE: DNA
<213> ORGANISM: Homo sapiens

<400> SEQUENCE: 81
ccctttctgg agaagtccac                                              20

<210> SEQ ID NO 82
<211> LENGTH: 39
<212> TYPE: DNA
<213> ORGANISM: Homo sapiens

<400> SEQUENCE: 82
gcagcagcgg ccgcctgaac aaggatccca gttacagtc                         39

<210> SEQ ID NO 83
<211> LENGTH: 37
<212> TYPE: DNA
<213> ORGANISM: Homo sapiens

<400> SEQUENCE: 83
gcagcagtcg acctttggaa ccatccctga catctcc                           37

<210> SEQ ID NO 84
<211> LENGTH: 39
<212> TYPE: DNA
<213> ORGANISM: Homo sapiens

<400> SEQUENCE: 84
gcagcagcgg ccgcatgctg ctgctgcccc tgctgctgc                         39

<210> SEQ ID NO 85
<211> LENGTH: 37
<212> TYPE: DNA
<213> ORGANISM: Homo sapiens

<400> SEQUENCE: 85
gcagcagtcg acctgggagc ccagagggtg ctgagcg                           37

<210> SEQ ID NO 86
<211> LENGTH: 21
<212> TYPE: DNA
<213> ORGANISM: Homo sapiens
```

-continued

```
<400> SEQUENCE: 86
cagggatggt tccaaagtga a                                              21

<210> SEQ ID NO 87
<211> LENGTH: 20
<212> TYPE: DNA
<213> ORGANISM: Homo sapiens

<400> SEQUENCE: 87
gtgcgactcc cacacacttg                                                20

<210> SEQ ID NO 88
<211> LENGTH: 25
<212> TYPE: DNA
<213> ORGANISM: Homo sapiens

<400> SEQUENCE: 88
aggtctccat ggcaacagga cacca                                          25
```